US011104891B2

(12) United States Patent
Dong et al.

(10) Patent No.: US 11,104,891 B2
(45) Date of Patent: Aug. 31, 2021

(54) ENGINEERED BOTULINUM NEUROTOXINS

(71) Applicants: Children's Medical Center Corporation, Boston, MA (US); Paul Stenmark, Stockholm (SE)

(72) Inventors: Min Dong, Weatogue, CT (US); Sicai Zhang, Boston, MA (US); Paul Stenmark, Stockholm (SE)

(73) Assignee: Children's Medical Center Corporation, Boston, MA (US)

(*) Notice: Subject to any disclaimer, the term of this patent is extended or adjusted under 35 U.S.C. 154(b) by 99 days.

(21) Appl. No.: 16/308,146

(22) PCT Filed: Jun. 8, 2017

(86) PCT No.: PCT/US2017/036628

§ 371 (c)(1),
(2) Date: Dec. 7, 2018

(87) PCT Pub. No.: WO2017/214447

PCT Pub. Date: Dec. 14, 2017

(65) Prior Publication Data

US 2019/0300869 A1 Oct. 3, 2019

Related U.S. Application Data

(60) Provisional application No. 62/347,579, filed on Jun. 8, 2016.

(51) Int. Cl.
*C07K 14/33* (2006.01)
*C12N 9/52* (2006.01)
*A61K 38/48* (2006.01)
*A61K 38/00* (2006.01)

(52) U.S. Cl.
CPC ............ *C12N 9/52* (2013.01); *A61K 38/4893* (2013.01); *C07K 14/33* (2013.01); *C12Y 304/24069* (2013.01); *A61K 38/00* (2013.01); *C07K 2319/00* (2013.01)

(58) Field of Classification Search
None
See application file for complete search history.

(56) References Cited

U.S. PATENT DOCUMENTS

2019/0127427 A1* 5/2019 Liu ........................ A61P 25/04

FOREIGN PATENT DOCUMENTS

WO WO 2013/180799 A1 12/2013
WO WO 2016/149404 A1 9/2016

OTHER PUBLICATIONS

Rummel et al. 2007 (Identification of the protein receptor binding site of botulinum neurotoxins B and G proves the double-receptor concept; Proc. Nat. Acad. Sci. 104(1):359-364) (Year: 2007).*
U.S. Appl. No. 16/651,720, filed Mar. 27, 2020, Dong et al.
EP 17733667.4, Mar. 30, 2020, European Exam Report.
PCT/US2017/036628, Oct. 2, 2017, International Search Report and Written Opinion.
PCT/US2017/036628, Dec. 20, 2018, International Preliminary Report on Patentability.
[No Author Listed] UniProt Database. Neurotoxin B8. Retrieved from EBI Accession No. UNIPROT: 16Z869. Oct. 3, 2012. 5 pgs.
[No Author Listed] UniProt Database. A5816_002916_Botulinum-like toxin eBoNT/J.*Enterococcus* sp. (strain 3G-1_DIV0629). Retrieved from EBI Accession No. UniProtKB:A0A242DI27. Oct. 3, 2012. 5 pgs.
Berntsson et al., Crystal structures of botulinum neurotoxin DC in complex with its protein receptors synaptotagmin I and II. Cell Structure. Sep. 3, 2013: 21(9) 1602-1611.
Earl et al., *Enterococcus* sp. 3G1_DIV0629 hypothetical protein. Coding ID: OTO22244.1. ENA Database. Submitted on May 8, 2017. Retrieved on Jan. 21, 2019 from https://www.ebi.ac.uk/ena/data/view/OTO22244.
Pirazzini et al., Botulinum Neurotoxins: Biology, Pharmacology, and Toxicology. Pharmacol Rev. Apr. 2017;69(2):200-235.
Zhang et al., Identification of a Botulinum Neurotoxin-like Toxin in a Commensal Strain of *Enterococcus faecium*. Cell Host Microbe. Feb. 14, 2018;23(2):169-176.e6.

* cited by examiner

*Primary Examiner* — Mary Maille Lyons
(74) *Attorney, Agent, or Firm* — Wolf, Greenfield & Sacks, P.C.

(57) ABSTRACT

Disclosed herein are modified *Clostridial Botulinum* neurotoxin (BoNT) polypeptides with a modified receptor binding domain of *Clostridial Botulinum* serotype B, comprising one or more substitution mutations at positions corresponding 1248 or 1249 in serotype B, strain 1. Specific substitution mutations include I1248F, I1248Y, I1248H, I1248W, V1249W, V1249F, V1249Y, V1249H, I1248W/V1249F, I1248W/V1249Y, I1248W/V1249H, I1248F/V1249Y, I1248F/V1249H, I1248Y/V1249H, I1248F/V1249W, I1248Y/V1249W, I1248H/V1249W, I1248Y/V1249F, I1248H/V1249F, or I1248H/V1249Y. Other substitution mutations are also disclosed. Isolated modified receptor binding domains, chimeric molecules, pharmaceutical compositions, and methods of using the same are also disclosed.

26 Claims, 6 Drawing Sheets

Specification includes a Sequence Listing.

| Toxins | Protein Receptors |
|---|---|
| BoNT/B, G, D-C | Synaptotagmin I and II (Syt I/II) |
| BoNT/A, E, D, F | SV2A, B, and C |

WT
I1248W
I1248W/V1249W
BoNT/B-Hc
Synapsin
Overlay

FIG. 5

SEQUENCE LISTING

```
<160> NUMBER OF SEQ ID NOS: 66

<210> SEQ ID NO 1
<211> LENGTH: 1291
<212> TYPE: PRT
<213> ORGANISM: Clostridial Botulinum

<400> SEQUENCE: 1

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80
```

-continued

```
Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
```

-continued

```
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925
```

```
Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                1015                1020

Ser Asn  Thr Asp Ile Lys Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Arg Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
    1115                1120                1125

Gln Asn  Ser Lys Tyr Ile Asn  Tyr Arg Asp Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Leu Asn  Gln Glu Trp Arg Val  Tyr Thr Tyr Lys Tyr  Phe Lys Lys
    1175                1180                1185

Glu Glu  Glu Lys Leu Phe Leu  Ala Pro Ile Ser Asp  Ser Asp Glu
    1190                1195                1200

Phe Tyr  Asn Thr Ile Gln Ile  Lys Glu Tyr Asp Glu  Gln Pro Thr
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Arg Phe Tyr Glu  Ser Gly Ile
    1235                1240                1245

Val Phe  Glu Glu Tyr Lys Asp  Tyr Phe Cys Ile Ser  Lys Trp Tyr
    1250                1255                1260

Leu Lys  Glu Val Lys Arg Lys  Pro Tyr Asn Leu Lys  Leu Gly Cys
    1265                1270                1275

Asn Trp  Gln Phe Ile Pro Lys  Asp Glu Gly Trp Thr  Glu
    1280                1285                1290
```

<210> SEQ ID NO 2
<211> LENGTH: 1291
<212> TYPE: PRT
<213> ORGANISM: Clostridial Botulinum

<400> SEQUENCE: 2

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415
```

```
Asn Lys Gln Ala Tyr Glu Glu Ile Ser Lys Glu His Leu Ala Val Tyr
            420                 425                 430

Lys Ile Gln Met Cys Lys Ser Val Arg Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asp Thr Gln Ser Asn
465                 470                 475                 480

Tyr Ile Glu Asn Arg Ser Ser Ile Asp Glu Leu Ile Leu Asp Thr Asn
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asp Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Val
        755                 760                 765

Asp Asn Ile Asn Asn Phe Ile Asn Glu Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys His Leu
            820                 825                 830
```

-continued

```
Lys Thr Ile Ile Pro Phe Asp Leu Ser Met Tyr Thr Asn Asn Thr Ile
        835                 840                 845

Leu Ile Glu Ile Phe Asn Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Asn Val Glu Val Tyr Asp Gly Val Glu Leu Asn Asp Lys
                885                 890                 895

Asn Gln Phe Lys Leu Thr Ser Ser Thr Asn Ser Glu Ile Arg Val Thr
            900                 905                 910

Gln Asn Gln Asn Ile Ile Phe Asn Ser Met Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Ile Lys Asn Asn Ser
945                 950                 955                 960

Gly Trp Lys Ile Ser Ile Arg Gly Asn Arg Ile Ile Trp Thr Leu Thr
                965                 970                 975

Asp Ile Asn Gly Lys Thr Lys Ser Val Phe Phe Glu Tyr Ser Ile Arg
            980                 985                 990

Glu Asp Ile Ser Asp Tyr Ile Asn  Arg Trp Phe Phe Val  Thr Ile Thr
        995                 1000                1005

Asn Asn  Ser Asp Asn Ala Lys  Ile Tyr Ile Asn Gly  Lys Leu Glu
    1010                1015                1020

Ser Asn  Ile Asp Ile Lys Asp  Ile Gly Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Lys Glu Ile Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Ser Val Gly Glu  Ile Leu Thr Arg Ser  Lys Tyr Asn
    1115                1120                1125

Gln Asn  Ser Asn Tyr Ile Asn  Tyr Arg Asn Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Ser Asn  Arg Glu Trp Arg Val  Tyr Ala Tyr Lys Asp  Phe Lys Glu
    1175                1180                1185

Glu Glu  Lys Lys Leu Phe Leu  Ala Asn Ile Tyr Asp  Ser Asn Glu
    1190                1195                1200

Phe Tyr  Lys Thr Ile Gln Ile  Lys Glu Tyr Asp Glu  Gln Pro Thr
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Arg Phe Tyr Glu  Ser Gly Ile
```

```
    1235                1240                1245

Val Leu  Lys Asp Tyr Lys Asn  Tyr Phe Cys Ile Ser  Lys Trp Tyr
    1250                1255                1260

Leu Lys  Glu Val Lys Arg Lys  Pro Tyr Asn Pro Asn  Leu Gly Cys
    1265                1270                1275

Asn Trp  Gln Phe Ile Pro Lys  Asp Glu Gly Trp Ile  Glu
    1280                1285                1290


<210> SEQ ID NO 3
<211> LENGTH: 1291
<212> TYPE: PRT
<213> ORGANISM: Clostridial Botulinum

<400> SEQUENCE: 3

Met Pro Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Arg Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320
```

```
Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Arg Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asp Thr Gln Ser Asn
465                 470                 475                 480

Tyr Ile Glu Asn Arg Ser Ser Ile Asp Glu Leu Ile Leu Asp Thr Asn
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asp Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Lys Ser Asn Ile Asn Ile Asp
```

```
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Glu Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys His Leu
            820                 825                 830

Lys Thr Ile Ile Pro Phe Asp Leu Ser Met Tyr Thr Asn Asn Thr Ile
        835                 840                 845

Leu Ile Glu Ile Phe Asn Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Lys Val Glu Val Tyr Asn Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asp Ile Ile Phe Asn Ser Met Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Ile Lys Asn Asn Ser
945                 950                 955                 960

Gly Trp Lys Ile Ser Ile Arg Gly Asn Lys Ile Ile Trp Thr Leu Thr
                965                 970                 975

Asp Ile Asn Gly Lys Thr Lys Ser Val Phe Phe Glu Tyr Ser Ile Arg
            980                 985                 990

Lys Asp Val Ser Glu Tyr Ile Asn  Arg Trp Phe Phe Val  Thr Ile Thr
        995                 1000                1005

Asn Asn  Ser Asp Asn Ala Lys  Ile Tyr Ile Asn Gly  Lys Leu Glu
    1010                1015                1020

Ser Asn  Ile Asp Ile Lys Asp  Ile Gly Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Lys Glu Ile Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Ser Val Gly Glu  Ile Leu Thr Arg Ser  Lys Tyr Asn
    1115                1120                1125

Gln Asn  Ser Asn Tyr Ile Asn  Tyr Arg Asn Leu Tyr  Ile Gly Glu
    1130                1135                1140

Lys Phe  Ile Ile Arg Arg Lys  Ser Asn Ser Gln Ser  Ile Asn Asp
    1145                1150                1155
```

```
Asp Ile  Val Arg Lys Glu Asp  Tyr Ile Tyr Leu Asp  Phe Phe Asn
    1160                 1165                 1170

Leu Asn  Gln Glu Trp Arg Val  Tyr Ala Tyr Lys Asp  Phe Lys Lys
    1175                 1180                 1185

Lys Glu  Glu Lys Leu Phe Leu  Ala Asn Ile Tyr Asp  Ser Asn Glu
    1190                 1195                 1200

Phe Tyr  Asn Thr Ile Gln Ile  Lys Glu Tyr Asp Glu  Gln Pro Thr
    1205                 1210                 1215

Tyr Ser  Cys Gln Leu Leu Phe  Lys Lys Asp Glu Glu  Ser Thr Asp
    1220                 1225                 1230

Glu Ile  Gly Leu Ile Gly Ile  His Arg Phe Tyr Glu  Ser Gly Ile
    1235                 1240                 1245

Val Phe  Lys Asp Tyr Lys Asp  Tyr Phe Cys Ile Ser  Lys Trp Tyr
    1250                 1255                 1260

Leu Lys  Glu Val Lys Arg Lys  Pro Tyr Asn Pro Asn  Leu Gly Cys
    1265                 1270                 1275

Asn Trp  Gln Phe Ile Pro Lys  Asp Glu Gly Trp Ile  Glu
    1280                 1285                 1290


<210> SEQ ID NO 4
<211> LENGTH: 1291
<212> TYPE: PRT
<213> ORGANISM: Clostridial Botulinum

<400> SEQUENCE: 4

Met Pro Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Gln Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
```

```
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
            340                 345                 350

Met Phe Gly Phe Thr Glu Ile Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Val Pro Gly Ile Cys Ile Asp
        435                 440                 445

Val Asp Asn Glu Asn Leu Phe Phe Ile Ala Asp Lys Asn Ser Phe Ser
    450                 455                 460

Asp Asp Leu Ser Lys Asn Glu Arg Val Glu Tyr Asn Thr Gln Asn Asn
465                 470                 475                 480

Tyr Ile Gly Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Val Phe Thr Asp Glu Asn Thr Ile Phe Gln Tyr Leu Tyr Ser Gln
    530                 535                 540

Thr Phe Pro Leu Asn Ile Arg Asp Ile Ser Leu Thr Ser Ser Phe Asp
545                 550                 555                 560

Asp Ala Leu Leu Val Ser Ser Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asp Glu Thr Ala Lys Gly Asn Phe Glu
625                 630                 635                 640

Ser Ala Phe Glu Ile Ala Gly Ser Ser Ile Leu Leu Glu Phe Ile Pro
                645                 650                 655
```

```
Glu Leu Leu Ile Pro Val Val Gly Val Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Val Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Glu Glu Lys Ser Asn Ile Asn Ile Asn
            740                 745                 750

Phe Asn Asp Ile Asn Ser Lys Leu Asn Asp Gly Ile Asn Gln Ala Met
        755                 760                 765

Asp Asn Ile Asn Asp Phe Ile Asn Glu Cys Ser Val Ser Tyr Leu Met
    770                 775                 780

Lys Lys Met Ile Pro Leu Ala Val Lys Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Val Glu Asp Glu Lys Ser Lys Val Asp Lys Tyr Leu
            820                 825                 830

Lys Thr Ile Ile Pro Phe Asp Leu Ser Thr Tyr Thr Asn Asn Glu Ile
        835                 840                 845

Leu Ile Lys Ile Phe Asn Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asp Ser Lys Ile Arg Val Thr
            900                 905                 910

Gln Asn Gln Asn Ile Ile Phe Asn Ser Met Phe Leu Asp Phe Ser Val
        915                 920                 925

Ser Phe Trp Ile Arg Ile Pro Lys Tyr Arg Asn Asp Asp Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asp Asn Ala Lys  Ile Tyr Ile Asn Gly  Thr Leu Glu
    1010                1015                1020

Ser Asn  Met Asp Ile Lys Asp  Ile Gly Glu Val Ile  Val Asn Gly
    1025                1030                1035

Glu Ile  Thr Phe Lys Leu Asp  Gly Asp Val Asp Arg  Thr Gln Phe
    1040                1045                1050

Ile Trp  Met Lys Tyr Phe Ser  Ile Phe Asn Thr Gln  Leu Asn Gln
    1055                1060                1065
```

```
Ser Asn  Ile Lys Glu Ile Tyr  Lys Ile Gln Ser Tyr  Ser Glu Tyr
    1070                 1075                 1080

Leu Lys  Asp Phe Trp Gly Asn  Pro Leu Met Tyr Asn  Lys Glu Tyr
    1085                 1090                 1095

Tyr Met  Phe Asn Ala Gly Asn  Lys Asn Ser Tyr Ile  Lys Leu Val
    1100                 1105                 1110

Lys Asp  Ser Ser Val Gly Glu  Ile Leu Ile Arg Ser  Lys Tyr Asn
    1115                 1120                 1125

Gln Asn  Ser Asn Tyr Ile Asn  Tyr Arg Asn Leu Tyr  Ile Gly Glu
    1130                 1135                 1140

Lys Phe  Ile Ile Arg Arg Lys  Ser Asn Ser Gln Ser  Ile Asn Asp
    1145                 1150                 1155

Asp Ile  Val Arg Lys Glu Asp  Tyr Ile His Leu Asp  Phe Val Asn
    1160                 1165                 1170

Ser Asn  Glu Glu Trp Arg Val  Tyr Ala Tyr Lys Asn  Phe Lys Glu
    1175                 1180                 1185

Gln Glu  Gln Lys Leu Phe Leu  Ser Ile Ile Tyr Asp  Ser Asn Glu
    1190                 1195                 1200

Phe Tyr  Lys Thr Ile Gln Ile  Lys Glu Tyr Asp Glu  Gln Pro Thr
    1205                 1210                 1215

Tyr Ser  Cys Gln Leu Leu Phe  Lys Lys Asp Glu Glu  Ser Thr Asp
    1220                 1225                 1230

Asp Ile  Gly Leu Ile Gly Ile  His Arg Phe Tyr Glu  Ser Gly Val
    1235                 1240                 1245

Leu Arg  Lys Lys Tyr Lys Asp  Tyr Phe Cys Ile Ser  Lys Trp Tyr
    1250                 1255                 1260

Leu Lys  Glu Val Lys Arg Lys  Pro Tyr Lys Ser Asn  Leu Gly Cys
    1265                 1270                 1275

Asn Trp  Gln Phe Ile Pro Lys  Asp Glu Gly Trp Thr  Glu
    1280                 1285                 1290


<210> SEQ ID NO 5
<211> LENGTH: 1291
<212> TYPE: PRT
<213> ORGANISM: Clostridial Botulinum

<400> SEQUENCE: 5

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Met Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140
```

```
Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Ala Tyr Asn Thr Gln Asn Asn
465                 470                 475                 480

Tyr Ile Glu Asn Asp Phe Ser Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Tyr Val Pro Val Tyr Lys Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560
```

-continued

```
Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Glu Thr Ile Asn Ser Ala Leu Thr Lys
        675                 680                 685

Arg Asp Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Arg Ser Asn Ile Asn Ile Asp
            740                 745                 750

Phe Asn Asp Val Asn Ser Lys Leu Asn Glu Gly Ile Asn Gln Ala Ile
        755                 760                 765

Asp Asn Ile Asn Asn Phe Ile Asn Glu Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Arg Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys Tyr Leu
            820                 825                 830

Lys Thr Ser Ile Pro Phe Asp Leu Ser Thr Tyr Thr Asn Asn Thr Ile
        835                 840                 845

Leu Ile Glu Ile Phe Asn Lys Tyr Asn Ser Asp Ile Leu Asn Asn Ile
    850                 855                 860

Ile Leu Asn Leu Arg Tyr Arg Asp Asn Lys Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asn Ser Lys Ile Arg Val Ile
            900                 905                 910

Gln Asn Gln Asn Ile Ile Phe Asn Ser Met Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
```

-continued

```
            980                 985                 990

Glu Asp Ile Ser Glu Tyr Ile Asn  Arg Trp Phe Phe Val  Thr Ile Thr
        995                 1000                1005

Asn Asn  Ser Asp Asn Ala Lys  Ile Tyr Ile Asn Gly  Lys Leu Glu
    1010                 1015                1020

Ser His  Ile Asp Ile Arg Asp  Ile Arg Glu Val Ile  Ala Asn Asp
    1025                 1030                1035

Glu Ile  Ile Phe Lys Leu Asp  Gly Asn Ile Asp Arg  Thr Gln Phe
    1040                 1045                1050

Ile Trp  Met Lys Tyr Phe Ser  Ile Phe Asn Thr Glu  Leu Ser Gln
    1055                 1060                1065

Ser Asn  Ile Glu Glu Ile Tyr  Lys Ile Gln Ser Tyr  Ser Glu Tyr
    1070                 1075                1080

Leu Lys  Asp Phe Trp Gly Asn  Pro Leu Met Tyr Asn  Lys Glu Tyr
    1085                 1090                1095

Tyr Met  Phe Asn Ala Gly Asn  Lys Asn Ser Tyr Ile  Lys Leu Lys
    1100                 1105                1110

Lys Asp  Ser Ser Val Gly Glu  Ile Leu Thr Arg Ser  Lys Tyr Asn
    1115                 1120                1125

Gln Asn  Ser Lys Tyr Ile Asn  Tyr Arg Asp Leu Tyr  Ile Gly Glu
    1130                 1135                1140

Lys Phe  Ile Ile Arg Arg Lys  Ser Asn Ser Gln Ser  Ile Asn Asp
    1145                 1150                1155

Asp Ile  Val Arg Lys Glu Asp  Tyr Ile Tyr Leu Asp  Phe Phe Asn
    1160                 1165                1170

Leu Asn  Gln Glu Trp Arg Val  Tyr Met Tyr Lys Tyr  Phe Lys Lys
    1175                 1180                1185

Glu Glu  Glu Lys Leu Phe Leu  Ala Pro Ile Ser Asp  Ser Asp Glu
    1190                 1195                1200

Phe Tyr  Asn Thr Ile Gln Ile  Lys Glu Tyr Asp Glu  Gln Pro Thr
    1205                 1210                1215

Tyr Ser  Cys Gln Leu Leu Phe  Lys Lys Asp Glu Glu  Ser Thr Asp
    1220                 1225                1230

Glu Ile  Gly Leu Ile Gly Ile  His Arg Phe Tyr Glu  Ser Gly Ile
    1235                 1240                1245

Val Phe  Lys Glu Tyr Lys Asp  Tyr Phe Cys Ile Ser  Lys Trp Tyr
    1250                 1255                1260

Leu Lys  Glu Val Lys Arg Lys  Pro Tyr Asn Ser Lys  Leu Gly Cys
    1265                 1270                1275

Asn Trp  Gln Phe Ile Pro Lys  Asp Glu Gly Trp Thr  Glu
    1280                 1285                1290


<210> SEQ ID NO 6
<211> LENGTH: 1291
<212> TYPE: PRT
<213> ORGANISM: Clostridial Botulinum

<400> SEQUENCE: 6

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45
```

```
Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Arg Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asp Thr Gln Ser Asn
```

```
465                 470                 475                 480

Tyr Ile Glu Asn Arg Ser Ser Ile Asp Glu Leu Ile Leu Asp Thr Asn
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Phe Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Asn Thr Met Asp Lys Leu Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asp Glu Lys Trp Arg Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Glu Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys His Leu
            820                 825                 830

Lys Thr Ile Ile Pro Phe Asp Leu Ser Met Tyr Thr Asn Asn Thr Ile
        835                 840                 845

Leu Ile Glu Ile Phe Lys Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Asn Val Glu Val Tyr Asp Gly Val Glu Leu Asn Asp Lys
                885                 890                 895
```

```
Asn Gln Phe Lys Leu Thr Ser Ser Thr Asn Ser Glu Ile Arg Val Thr
            900                 905                 910

Gln Asn Gln Asn Ile Ile Phe Asn Ser Met Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Ile Lys Asn Asn Ser
945                 950                 955                 960

Gly Trp Lys Ile Ser Ile Arg Gly Asn Arg Ile Ile Trp Thr Leu Thr
                965                 970                 975

Asp Ile Asn Gly Lys Thr Lys Ser Val Phe Phe Glu Tyr Ser Ile Arg
            980                 985                 990

Glu Asp Ile Ser Asp Tyr Ile Asn  Arg Trp Phe Phe Val  Thr Ile Thr
        995                 1000                1005

Asn Asn  Ser Asp Asn Ala Lys  Ile Tyr Ile Asn Gly  Lys Leu Glu
    1010                1015                1020

Ser Asn  Ile Asp Ile Lys Asp  Ile Gly Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Lys Glu Ile Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
    1115                1120                1125

Gln Asn  Ser Asn Tyr Ile Asn  Tyr Arg Asn Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Leu Asn  Gln Glu Trp Arg Val  Tyr Ala Leu Lys Asn  Phe Lys Lys
    1175                1180                1185

Lys Glu  Glu Lys Leu Phe Leu  Ala Pro Ile Ser Asp  Ser Asp Glu
    1190                1195                1200

Phe Tyr  Asn Thr Ile Gln Ile  Lys Glu Tyr Asp Glu  Gln Pro Thr
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Arg Phe Tyr Glu  Ser Gly Ile
    1235                1240                1245

Val Phe  Lys Asp Tyr Lys Tyr  Tyr Phe Cys Ile Ser  Lys Trp Tyr
    1250                1255                1260

Leu Lys  Glu Val Lys Arg Lys  Pro Tyr Asn Pro Asn  Leu Gly Cys
    1265                1270                1275

Asn Trp  Gln Phe Ile Pro Lys  Asp Glu Gly Trp Ile  Glu
    1280                1285                1290
```

<210> SEQ ID NO 7
<211> LENGTH: 1291
<212> TYPE: PRT
<213> ORGANISM: Clostridial Botulinum

<400> SEQUENCE: 7

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380
```

```
Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Lys Asn Ile
465                 470                 475                 480

Tyr Ile Glu Asn Tyr Phe Ser Ile Asn Glu Leu Ile Leu Asp Thr Asp
                485                 490                 495

Leu Ile Ser Gly Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Ile Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Val Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Lys Leu Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Glu Cys Ser Val Ser Tyr Leu Met
    770                 775                 780

Lys Lys Met Ile Pro Leu Ala Ile Glu Lys Leu Leu Asp Phe Asp Asn
785                 790                 795                 800
```

```
Ala Leu Lys Lys Asn Leu Leu Asn Tyr Ile Asp Glu Asn Lys Leu Tyr
            805                 810                 815

Leu Ile Gly Ser Val Glu Glu Glu Lys Ser Lys Val Asp Lys Phe Phe
            820                 825                 830

Lys Thr Ile Ile Pro Phe Asp Leu Ser Met Tyr Thr Asn Asn Thr Ile
        835                 840                 845

Leu Ile Glu Met Val Asn Lys Tyr Asn Ser Glu Ile Leu Asn Asn Ile
    850                 855                 860

Ile Leu Asn Leu Arg Tyr Arg Asp Asn Asn Leu Ile Asp Ser Ser Gly
865                 870                 875                 880

Tyr Gly Ala Lys Val Glu Val Tyr Asn Gly Val Glu Leu Asn Asp Lys
            885                 890                 895

Asn Gln Phe Lys Leu Thr Ser Ser Ala Asn Ser Lys Ile Lys Val Thr
            900                 905                 910

Gln Asn Gln Asn Ile Thr Phe Asn Ser Met Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Thr
            965                 970                 975

Asp Ile Asn Gly Lys Thr Lys Ser Val Phe Phe Glu Tyr Ser Ile Arg
            980                 985                 990

Glu Asp Ile Ser Asp Tyr Ile Asn  Arg Trp Phe Phe Val  Thr Ile Thr
        995                 1000                1005

Asn Asn  Leu Asp Asn Ala Lys  Ile Tyr Ile Asn Gly  Lys Leu Glu
    1010                1015                1020

Ser Asn  Ile Asp Ile Arg Asp  Ile Arg Glu Val Ile  Val Asn Gly
    1025                1030                1035

Glu Ile  Ile Phe Lys Leu Asp  Gly Glu Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Val Lys Glu Ile Tyr  Lys Ile Gln Ser Tyr  Ser Lys Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Val
    1100                1105                1110

Lys Asp  Ser Ser Val Gly Glu  Ile Leu Thr Arg Ser  Lys Tyr Asn
    1115                1120                1125

Gln Asn  Ser Asn Tyr Ile Asn  Tyr Arg Asn Leu Tyr  Ile Gly Glu
    1130                1135                1140

Lys Phe  Ile Ile Arg Arg Lys  Ser Ser Ser Gln Ser  Ile Ser Asp
    1145                1150                1155

Asp Ile  Val Arg Lys Glu Asp  Tyr Ile Tyr Leu Asp  Phe Phe Asn
    1160                1165                1170

Ser Asn  Arg Glu Trp Arg Val  Tyr Ala Tyr Lys Asn  Phe Lys Gly
    1175                1180                1185

Gln Glu  Glu Lys Leu Phe Leu  Ala Asn Ile Tyr Asp  Ser Asn Glu
    1190                1195                1200

Phe Tyr  Lys Thr Ile Gln Ile  Lys Glu Tyr Asp Glu  Gln Pro Thr
```

```
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Asn Phe Tyr Glu  Ser Gly Ile
    1235                1240                1245

Leu Phe  Lys Asp Tyr Lys Asp  Tyr Phe Cys Ile Ser  Lys Trp Tyr
    1250                1255                1260

Leu Lys  Glu Val Lys Lys Lys  Pro Tyr Ser Ser Asn  Leu Gly Cys
    1265                1270                1275

Asn Trp  Gln Phe Ile Pro Lys  Asp Glu Gly Trp Thr  Glu
    1280                1285                1290


<210> SEQ ID NO 8
<211> LENGTH: 1292
<212> TYPE: PRT
<213> ORGANISM: Clostridial Botulinum

<400> SEQUENCE: 8

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Gly Glu Glu Arg Lys Glu Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Gly Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285
```

```
Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asp Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Arg Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Ser Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ser Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asp Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
```

-continued

```
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Lys Ser Asn Ile Ser Ile Asp
            740                 745                 750

Phe Asn Asp Ile Asn Ser Lys Leu Asn Glu Gly Ile Asn Gln Ala Ile
        755                 760                 765

Asp Asn Ile Asn Asp Phe Ile Asn Glu Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys His Leu
            820                 825                 830

Lys Thr Ile Met Thr Phe Asp Leu Ser Met Tyr Thr Asn Asn Thr Ile
        835                 840                 845

Leu Ile Lys Met Val Asn Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Asn Val Glu Val Tyr Asp Gly Val Glu Leu Asn Asp Lys
                885                 890                 895

Asn Gln Phe Lys Leu Thr Ser Ser Thr Asn Ser Glu Ile Arg Val Thr
            900                 905                 910

Gln Asn Gln Asn Ile Ile Val Asn Ser Met Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Ile Lys Ser Val Phe Phe Glu Tyr Ser Ile Arg
            980                 985                 990

Lys Asp Val Ser Glu Tyr Ile Asn  Arg Trp Phe Phe Val  Thr Ile Thr
        995                 1000                1005

Asn Asn  Leu Asp Asn Ala Lys  Ile Tyr Ile Asn Gly  Lys Leu Glu
    1010                1015                1020

Ser Asn  Met Asp Ile Arg Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Ile Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Ser  Lys Asn Ser Tyr Ile  Lys Leu Lys
    1100                1105                1110

Lys Asp  Ser Ser Val Gly Glu  Ile Leu Thr Arg Ser  Lys Tyr Asn
    1115                1120                1125
```

```
Gln Asn  Ser Gln Tyr Ile Asn  Tyr Arg Asp Leu Tyr  Ile Gly Glu
    1130                 1135                 1140

Lys Phe  Ile Ile Lys Arg Lys  Ser Asn Ser Gln Ser  Ile Asn Asp
    1145                 1150                 1155

Asp Ile  Val Arg Lys Glu Asp  Tyr Ile Tyr Leu Asp  Phe Phe Asn
    1160                 1165                 1170

Leu Asn  Gln Glu Trp Arg Val  Tyr Ala Tyr Lys Asp  Phe Lys Gly
    1175                 1180                 1185

Gln Lys  Glu Gln Lys Leu Phe  Leu Ala Asn Ile His  Asp Ser Asn
    1190                 1195                 1200

Glu Phe  Tyr Lys Thr Ile Gln  Ile Lys Glu Tyr Asp  Glu Gln Pro
    1205                 1210                 1215

Thr Tyr  Ser Cys Gln Leu Leu  Phe Lys Lys Asp Glu  Glu Ser Thr
    1220                 1225                 1230

Asp Glu  Ile Gly Leu Ile Gly  Ile His Arg Phe Tyr  Glu Ser Gly
    1235                 1240                 1245

Phe Val  Phe Gln Glu Tyr Lys  Tyr Tyr Phe Cys Ile  Ser Lys Trp
    1250                 1255                 1260

Tyr Leu  Lys Glu Val Lys Lys  Lys Pro Tyr Asn Pro  Asp Leu Gly
    1265                 1270                 1275

Cys Asn  Trp Gln Phe Ile Pro  Lys Asp Glu Gly Trp  Thr Glu
    1280                 1285                 1290


<210> SEQ ID NO 9
<211> LENGTH: 432
<212> TYPE: PRT
<213> ORGANISM: Clostridial Botulinum

<400> SEQUENCE: 9

Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
```

```
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Thr Tyr Lys Tyr Phe Lys Lys Glu Glu Glu Lys Leu Phe Leu
                325                 330                 335

Ala Pro Ile Ser Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Ile Val Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430


<210> SEQ ID NO 10
<211> LENGTH: 432
<212> TYPE: PRT
<213> ORGANISM: Clostridial Botulinum

<400> SEQUENCE: 10

Ile Leu Asn Asn Ile Ile Leu Asn Leu Arg Tyr Arg Asp Asn Asn Leu
1               5                   10                  15

Ile Asp Leu Ser Gly Tyr Gly Ala Asn Val Glu Val Tyr Asp Gly Val
            20                  25                  30

Glu Leu Asn Asp Lys Asn Gln Phe Lys Leu Thr Ser Ser Thr Asn Ser
        35                  40                  45

Glu Ile Arg Val Thr Gln Asn Gln Asn Ile Ile Phe Asn Ser Met Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Ile Lys Asn Asn Ser Gly Trp Lys Ile Ser Ile Arg Gly Asn Arg Ile
            100                 105                 110

Ile Trp Thr Leu Thr Asp Ile Asn Gly Lys Thr Lys Ser Val Phe Phe
        115                 120                 125

Glu Tyr Ser Ile Arg Glu Asp Ile Ser Asp Tyr Ile Asn Arg Trp Phe
    130                 135                 140
```

```
Phe Val Thr Ile Thr Asn Asn Ser Asp Asn Ala Lys Ile Tyr Ile Asn
145                 150                 155                 160

Gly Lys Leu Glu Ser Asn Ile Asp Ile Lys Asp Ile Gly Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Lys Glu Ile Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Ser Val Gly Glu Ile Leu Thr Arg Ser Lys Tyr Asn Gln Asn Ser
            260                 265                 270

Asn Tyr Ile Asn Tyr Arg Asn Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Ser Asn Arg Glu Trp Arg
305                 310                 315                 320

Val Tyr Ala Tyr Lys Asp Phe Lys Glu Glu Glu Lys Lys Leu Phe Leu
                325                 330                 335

Ala Asn Ile Tyr Asp Ser Asn Glu Phe Tyr Lys Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Ile Val Leu Lys Asp Tyr Lys Asn Tyr Phe Cys Ile
385                 390                 395                 400

Ser Lys Trp Tyr Leu Lys Glu Val Lys Arg Lys Pro Tyr Asn Pro Asn
                405                 410                 415

Leu Gly Cys Asn Trp Gln Phe Ile Pro Lys Asp Glu Gly Trp Ile Glu
            420                 425                 430


<210> SEQ ID NO 11
<211> LENGTH: 432
<212> TYPE: PRT
<213> ORGANISM: Clostridial Botulinum

<400> SEQUENCE: 11

Ile Leu Asn Asn Ile Ile Leu Asn Leu Arg Tyr Arg Asp Asn Asn Leu
1               5                   10                  15

Ile Asp Leu Ser Gly Tyr Gly Ala Lys Val Glu Val Tyr Asn Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asp Ile Ile Phe Asn Ser Met Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95
```

```
Ile Lys Asn Asn Ser Gly Trp Lys Ile Ser Ile Arg Gly Asn Lys Ile
            100                 105                 110

Ile Trp Thr Leu Thr Asp Ile Asn Gly Lys Thr Lys Ser Val Phe Phe
        115                 120                 125

Glu Tyr Ser Ile Arg Lys Asp Val Ser Glu Tyr Ile Asn Arg Trp Phe
    130                 135                 140

Phe Val Thr Ile Thr Asn Asn Ser Asp Asn Ala Lys Ile Tyr Ile Asn
145                 150                 155                 160

Gly Lys Leu Glu Ser Asn Ile Asp Ile Lys Asp Ile Gly Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Lys Glu Ile Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Ser Val Gly Glu Ile Leu Thr Arg Ser Lys Tyr Asn Gln Asn Ser
            260                 265                 270

Asn Tyr Ile Asn Tyr Arg Asn Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Ala Tyr Lys Asp Phe Lys Lys Lys Glu Glu Lys Leu Phe Leu
                325                 330                 335

Ala Asn Ile Tyr Asp Ser Asn Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Ile Val Phe Lys Asp Tyr Lys Asp Tyr Phe Cys Ile
385                 390                 395                 400

Ser Lys Trp Tyr Leu Lys Glu Val Lys Arg Lys Pro Tyr Asn Pro Asn
                405                 410                 415

Leu Gly Cys Asn Trp Gln Phe Ile Pro Lys Asp Glu Gly Trp Ile Glu
            420                 425                 430


<210> SEQ ID NO 12
<211> LENGTH: 432
<212> TYPE: PRT
<213> ORGANISM: Clostridial Botulinum

<400> SEQUENCE: 12

Ile Leu Asn Asn Ile Ile Leu Asn Leu Arg Tyr Arg Asp Asn Asn Leu
1               5                   10                  15

Ile Asp Leu Ser Gly Tyr Gly Ala Lys Val Glu Val Tyr Asp Gly Val
            20                  25                  30

Lys Leu Asn Asp Lys Asn Gln Phe Lys Leu Thr Ser Ser Ala Asp Ser
```

```
        35                  40                  45

Lys Ile Arg Val Thr Gln Asn Gln Asn Ile Ile Phe Asn Ser Met Phe
    50                  55                  60

Leu Asp Phe Ser Val Ser Phe Trp Ile Arg Ile Pro Lys Tyr Arg Asn
65                  70                  75                  80

Asp Asp Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asp Asn Ala Lys Ile Tyr Ile Asn
145                 150                 155                 160

Gly Thr Leu Glu Ser Asn Met Asp Ile Lys Asp Ile Gly Glu Val Ile
                165                 170                 175

Val Asn Gly Glu Ile Thr Phe Lys Leu Asp Gly Asp Val Asp Arg Thr
            180                 185                 190

Gln Phe Ile Trp Met Lys Tyr Phe Ser Ile Phe Asn Thr Gln Leu Asn
        195                 200                 205

Gln Ser Asn Ile Lys Glu Ile Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Val Lys Asp
                245                 250                 255

Ser Ser Val Gly Glu Ile Leu Ile Arg Ser Lys Tyr Asn Gln Asn Ser
            260                 265                 270

Asn Tyr Ile Asn Tyr Arg Asn Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile His Leu Asp Phe Val Asn Ser Asn Glu Glu Trp Arg
305                 310                 315                 320

Val Tyr Ala Tyr Lys Asn Phe Lys Glu Gln Glu Gln Lys Leu Phe Leu
                325                 330                 335

Ser Ile Ile Tyr Asp Ser Asn Glu Phe Tyr Lys Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Asp Ile Gly Leu Ile Gly Ile His Arg Phe
    370                 375                 380

Tyr Glu Ser Gly Val Leu Arg Lys Lys Tyr Lys Asp Tyr Phe Cys Ile
385                 390                 395                 400

Ser Lys Trp Tyr Leu Lys Glu Val Lys Arg Lys Pro Tyr Lys Ser Asn
                405                 410                 415

Leu Gly Cys Asn Trp Gln Phe Ile Pro Lys Asp Glu Gly Trp Thr Glu
            420                 425                 430
```

<210> SEQ ID NO 13
<211> LENGTH: 432
<212> TYPE: PRT
<213> ORGANISM: Clostridial Botulinum

<400> SEQUENCE: 13

```
Ile Leu Asn Asn Ile Ile Leu Asn Leu Arg Tyr Arg Asp Asn Lys Leu
1               5                   10                  15

Ile Asp Leu Ser Gly Tyr Gly Ala Lys Val Glu Val Tyr Asp Gly Val
            20                  25                  30

Lys Leu Asn Asp Lys Asn Gln Phe Lys Leu Thr Ser Ser Ala Asn Ser
        35                  40                  45

Lys Ile Arg Val Ile Gln Asn Gln Asn Ile Ile Phe Asn Ser Met Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Met Ile
            100                 105                 110

Ile Trp Thr Leu Ile Asp Ile Asn Gly Lys Ile Lys Ser Val Phe Phe
        115                 120                 125

Glu Tyr Ser Ile Lys Glu Asp Ile Ser Glu Tyr Ile Asn Arg Trp Phe
    130                 135                 140

Phe Val Thr Ile Thr Asn Asn Ser Asp Asn Ala Lys Ile Tyr Ile Asn
145                 150                 155                 160

Gly Lys Leu Glu Ser His Ile Asp Ile Arg Asp Ile Arg Glu Val Ile
                165                 170                 175

Ala Asn Asp Glu Ile Ile Phe Lys Leu Asp Gly Asn Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Ile Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Ser Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Met Tyr Lys Tyr Phe Lys Lys Glu Glu Glu Lys Leu Phe Leu
                325                 330                 335

Ala Pro Ile Ser Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Ile Val Phe Lys Glu Tyr Lys Asp Tyr Phe Cys Ile
385                 390                 395                 400

Ser Lys Trp Tyr Leu Lys Glu Val Lys Arg Lys Pro Tyr Asn Ser Lys
```

```
                405                 410                 415

Leu Gly Cys Asn Trp Gln Phe Ile Pro Lys Asp Glu Gly Trp Thr Glu
            420                 425                 430


<210> SEQ ID NO 14
<211> LENGTH: 432
<212> TYPE: PRT
<213> ORGANISM: Clostridial Botulinum

<400> SEQUENCE: 14

Ile Leu Asn Asn Ile Ile Leu Asn Leu Arg Tyr Arg Asp Asn Asn Leu
1               5                   10                  15

Ile Asp Leu Ser Gly Tyr Gly Ala Asn Val Glu Val Tyr Asp Gly Val
            20                  25                  30

Glu Leu Asn Asp Lys Asn Gln Phe Lys Leu Thr Ser Ser Thr Asn Ser
        35                  40                  45

Glu Ile Arg Val Thr Gln Asn Gln Asn Ile Ile Phe Asn Ser Met Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Ile Lys Asn Asn Ser Gly Trp Lys Ile Ser Ile Arg Gly Asn Arg Ile
            100                 105                 110

Ile Trp Thr Leu Thr Asp Ile Asn Gly Lys Thr Lys Ser Val Phe Phe
        115                 120                 125

Glu Tyr Ser Ile Arg Glu Asp Ile Ser Asp Tyr Ile Asn Arg Trp Phe
    130                 135                 140

Phe Val Thr Ile Thr Asn Asn Ser Asp Asn Ala Lys Ile Tyr Ile Asn
145                 150                 155                 160

Gly Lys Leu Glu Ser Asn Ile Asp Ile Lys Asp Ile Gly Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Lys Glu Ile Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Asn Tyr Ile Asn Tyr Arg Asn Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Ala Leu Lys Asn Phe Lys Lys Lys Glu Glu Lys Leu Phe Leu
                325                 330                 335

Ala Pro Ile Ser Asp Ser Asp Glu Phe Tyr Asn Thr Ile Gln Ile Lys
            340                 345                 350
```

```
Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Ile Val Phe Lys Asp Tyr Lys Tyr Tyr Phe Cys Ile
385                 390                 395                 400

Ser Lys Trp Tyr Leu Lys Glu Val Lys Arg Lys Pro Tyr Asn Pro Asn
                405                 410                 415

Leu Gly Cys Asn Trp Gln Phe Ile Pro Lys Asp Glu Gly Trp Ile Glu
            420                 425                 430


<210> SEQ ID NO 15
<211> LENGTH: 432
<212> TYPE: PRT
<213> ORGANISM: Clostridial Botulinum

<400> SEQUENCE: 15

Ile Leu Asn Asn Ile Ile Leu Asn Leu Arg Tyr Arg Asp Asn Asn Leu
1               5                   10                  15

Ile Asp Ser Ser Gly Tyr Gly Ala Lys Val Glu Val Tyr Asn Gly Val
            20                  25                  30

Glu Leu Asn Asp Lys Asn Gln Phe Lys Leu Thr Ser Ser Ala Asn Ser
        35                  40                  45

Lys Ile Lys Val Thr Gln Asn Gln Asn Ile Thr Phe Asn Ser Met Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Thr Asp Ile Asn Gly Lys Thr Lys Ser Val Phe Phe
        115                 120                 125

Glu Tyr Ser Ile Arg Glu Asp Ile Ser Asp Tyr Ile Asn Arg Trp Phe
    130                 135                 140

Phe Val Thr Ile Thr Asn Asn Leu Asp Asn Ala Lys Ile Tyr Ile Asn
145                 150                 155                 160

Gly Lys Leu Glu Ser Asn Ile Asp Ile Arg Asp Ile Arg Glu Val Ile
                165                 170                 175

Val Asn Gly Glu Ile Ile Phe Lys Leu Asp Gly Glu Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Val Lys Glu Ile Tyr Lys Ile Gln Ser Tyr Ser Lys Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Val Lys Asp
                245                 250                 255

Ser Ser Val Gly Glu Ile Leu Thr Arg Ser Lys Tyr Asn Gln Asn Ser
            260                 265                 270

Asn Tyr Ile Asn Tyr Arg Asn Leu Tyr Ile Gly Glu Lys Phe Ile Ile
        275                 280                 285

Arg Arg Lys Ser Ser Ser Gln Ser Ile Ser Asp Asp Ile Val Arg Lys
    290                 295                 300
```

```
Glu Asp Tyr Ile Tyr Leu Asp Phe Phe Asn Ser Asn Arg Glu Trp Arg
305                 310                 315                 320

Val Tyr Ala Tyr Lys Asn Phe Lys Gly Gln Glu Glu Lys Leu Phe Leu
                325                 330                 335

Ala Asn Ile Tyr Asp Ser Asn Glu Phe Tyr Lys Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Asn Phe
    370                 375                 380

Tyr Glu Ser Gly Ile Leu Phe Lys Asp Tyr Lys Asp Tyr Phe Cys Ile
385                 390                 395                 400

Ser Lys Trp Tyr Leu Lys Glu Val Lys Lys Lys Pro Tyr Ser Ser Asn
                405                 410                 415

Leu Gly Cys Asn Trp Gln Phe Ile Pro Lys Asp Glu Gly Trp Thr Glu
            420                 425                 430


<210> SEQ ID NO 16
<211> LENGTH: 433
<212> TYPE: PRT
<213> ORGANISM: Clostridial Botulinum

<400> SEQUENCE: 16

Ile Leu Asn Asn Ile Ile Leu Asn Leu Arg Tyr Arg Asp Asn Asn Leu
1               5                   10                  15

Ile Asp Leu Ser Gly Tyr Gly Ala Asn Val Glu Val Tyr Asp Gly Val
            20                  25                  30

Glu Leu Asn Asp Lys Asn Gln Phe Lys Leu Thr Ser Ser Thr Asn Ser
        35                  40                  45

Glu Ile Arg Val Thr Gln Asn Gln Asn Ile Ile Val Asn Ser Met Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Ile Lys Ser Val Phe Phe
        115                 120                 125

Glu Tyr Ser Ile Arg Lys Asp Val Ser Glu Tyr Ile Asn Arg Trp Phe
    130                 135                 140

Phe Val Thr Ile Thr Asn Asn Leu Asp Asn Ala Lys Ile Tyr Ile Asn
145                 150                 155                 160

Gly Lys Leu Glu Ser Asn Met Asp Ile Arg Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Ile Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Ser Lys Asn Ser Tyr Ile Lys Leu Lys Lys Asp
```

```
                245                 250                 255

Ser Ser Val Gly Glu Ile Leu Thr Arg Ser Lys Tyr Asn Gln Asn Ser
            260                 265                 270

Gln Tyr Ile Asn Tyr Arg Asp Leu Tyr Ile Gly Glu Lys Phe Ile Ile
        275                 280                 285

Lys Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Ala Tyr Lys Asp Phe Lys Gly Gln Lys Glu Gln Lys Leu Phe
                325                 330                 335

Leu Ala Asn Ile His Asp Ser Asn Glu Phe Tyr Lys Thr Ile Gln Ile
            340                 345                 350

Lys Glu Tyr Asp Glu Gln Pro Thr Tyr Ser Cys Gln Leu Leu Phe Lys
        355                 360                 365

Lys Asp Glu Glu Ser Thr Asp Glu Ile Gly Leu Ile Gly Ile His Arg
    370                 375                 380

Phe Tyr Glu Ser Gly Phe Val Phe Gln Glu Tyr Lys Tyr Tyr Phe Cys
385                 390                 395                 400

Ile Ser Lys Trp Tyr Leu Lys Glu Val Lys Lys Lys Pro Tyr Asn Pro
                405                 410                 415

Asp Leu Gly Cys Asn Trp Gln Phe Ile Pro Lys Asp Glu Gly Trp Thr
            420                 425                 430

Glu


<210> SEQ ID NO 17
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 17

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175
```

```
Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590
```

```
Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
```

```
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095

Asp Phe  Trp Gly Asn Pro Leu  Met Tyr Asn Lys Glu  Tyr Tyr Met
    1100                1105                1110

Phe Asn  Ala Gly Asn Lys Asn  Ser Tyr Ile Lys Leu  Lys Lys Asp
    1115                1120                1125

Ser Pro  Val Gly Glu Ile Leu  Thr Arg Ser Lys Tyr  Asn Gln Asn
    1130                1135                1140

Ser Lys  Tyr Ile Asn Tyr Arg  Asp Leu Tyr Ile Gly  Glu Lys Phe
    1145                1150                1155

Ile Ile  Arg Arg Lys Ser Asn  Ser Gln Ser Ile Asn  Asp Asp Ile
    1160                1165                1170

Val Arg  Lys Glu Asp Tyr Ile  Tyr Leu Asp Phe Phe  Asn Leu Asn
    1175                1180                1185

Gln Glu  Trp Arg Val Tyr Thr  Tyr Lys Tyr Phe Lys  Lys Glu Glu
    1190                1195                1200

Glu Lys  Leu Phe Leu Ala Pro  Ile Ser Asp Ser Asp  Glu Phe Tyr
    1205                1210                1215

Asn Thr  Ile Gln Ile Lys Glu  Tyr Asp Glu Gln Pro  Thr Tyr Ser
    1220                1225                1230

Cys Gln  Leu Leu Phe Lys Lys  Asp Glu Glu Ser Thr  Asp Glu Ile
    1235                1240                1245

Gly Leu  Ile Gly Ile His Arg  Phe Tyr Glu Ser Gly  Ile Val Phe
    1250                1255                1260

Glu Glu  Tyr Lys Asp Tyr Phe  Cys Ile Ser Lys Trp  Tyr Leu Lys
    1265                1270                1275

Glu Val  Lys Arg Lys Pro Tyr  Asn Leu Lys Leu Gly  Cys Asn Trp
    1280                1285                1290

Gln Phe  Ile Pro Lys Asp Glu  Gly Trp Thr Glu
    1295                1300


<210> SEQ ID NO 18
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 18

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
```

```
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Val Ala Ser Thr Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Asn Phe Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
                405                 410                 415

Lys Asn Phe Thr Gly Leu Phe Glu Phe Tyr Lys Leu Leu Cys Val Arg
            420                 425                 430

Gly Ile Ile Pro Phe Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480
```

```
Ile Thr Ala Asp Thr Asn Ile Glu Ala Ala Glu Glu Asn Ile Ser Leu
                485                 490                 495

Asp Leu Ile Gln Gln Tyr Tyr Leu Thr Phe Asp Phe Asp Asn Glu Pro
            500                 505                 510

Glu Asn Ile Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Asp Ser Arg Ile Ile Leu Thr Asn Ser Ala Glu Glu Ala Leu
                565                 570                 575

Leu Lys Pro Asn Val Ala Tyr Thr Phe Phe Ser Ser Lys Tyr Val Lys
            580                 585                 590

Lys Ile Asn Lys Ala Val Glu Ala Phe Met Phe Leu Asn Trp Ala Glu
        595                 600                 605

Glu Leu Val Tyr Asp Phe Thr Asp Glu Thr Asn Glu Val Thr Thr Met
    610                 615                 620

Asp Lys Ile Ala Asp Ile Thr Ile Ile Val Pro Tyr Ile Gly Pro Ala
625                 630                 635                 640

Leu Asn Ile Gly Asn Met Leu Ser Lys Gly Glu Phe Val Glu Ala Ile
                645                 650                 655

Ile Phe Thr Gly Val Val Ala Met Leu Glu Phe Ile Pro Glu Tyr Ala
            660                 665                 670

Leu Pro Val Phe Gly Thr Phe Ala Ile Val Ser Tyr Ile Ala Asn Lys
        675                 680                 685

Val Leu Thr Val Gln Thr Ile Asn Asn Ala Leu Ser Lys Arg Asn Glu
    690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Val Leu
            820                 825                 830

Gln Val Asp Arg Leu Lys Asp Glu Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895
```

```
Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                 1005

Ser Glu  Tyr Ile Asn Arg Trp  Phe Phe Val Thr Ile  Thr Asn Asn
    1010                 1015                 1020

Leu Asn  Asn Ala Lys Ile Tyr  Ile Asn Gly Lys Leu  Glu Ser Asn
    1025                 1030                 1035

Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Glu Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Ile Val Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
```

```
    1295                1300


<210> SEQ ID NO 19
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 19

Met Pro Phe Val Asn Lys Pro Phe Asn Tyr Arg Asp Pro Gly Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Glu Gly Val Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Ile Lys Leu Phe Asp
                85                  90                  95

Arg Ile Tyr Ser Thr Gly Leu Gly Arg Met Leu Leu Ser Phe Ile Val
            100                 105                 110

Lys Gly Ile Pro Phe Trp Gly Gly Ser Thr Ile Asp Thr Glu Leu Lys
        115                 120                 125

Val Ile Asp Thr Asn Cys Ile Asn Val Ile Glu Pro Gly Gly Ser Tyr
    130                 135                 140

Arg Ser Glu Glu Leu Asn Leu Val Ile Thr Gly Pro Ser Ala Asp Ile
145                 150                 155                 160

Ile Gln Phe Glu Cys Lys Ser Phe Gly His Asp Val Phe Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Thr Phe Ala Thr Asp Pro Ala Val Thr Leu Ala His Glu
    210                 215                 220

Leu Ile His Ala Ala His Arg Leu Tyr Gly Ile Ala Ile Asn Pro Asn
225                 230                 235                 240

Arg Val Leu Lys Val Lys Thr Asn Ala Tyr Tyr Glu Met Ser Gly Leu
                245                 250                 255

Glu Val Ser Phe Glu Glu Leu Arg Thr Phe Gly Gly Asn Asp Thr Asn
            260                 265                 270

Phe Ile Asp Ser Leu Trp Gln Lys Lys Phe Ser Arg Asp Ala Tyr Asp
        275                 280                 285

Asn Leu Gln Asn Ile Ala Arg Ile Leu Asn Glu Ala Lys Thr Ile Val
    290                 295                 300

Gly Thr Thr Thr Pro Leu Gln Tyr Met Lys Asn Ile Phe Ile Arg Lys
305                 310                 315                 320

Tyr Phe Leu Ser Glu Asp Ala Ser Gly Lys Ile Ser Val Asn Lys Ala
                325                 330                 335

Ala Phe Lys Glu Phe Tyr Arg Val Leu Thr Arg Gly Phe Thr Glu Leu
            340                 345                 350

Glu Phe Val Asn Pro Phe Lys Val Ile Asn Arg Lys Thr Tyr Leu Asn
```

```
        355                 360                 365

Phe Asp Lys Ala Val Phe Arg Ile Asn Ile Val Pro Asp Glu Asn Tyr
    370                 375                 380

Thr Ile Asn Glu Gly Phe Asn Leu Glu Gly Ala Asn Ser Asn Gly Gln
385                 390                 395                 400

Asn Thr Glu Ile Asn Ser Arg Asn Phe Thr Arg Leu Lys Asn Phe Thr
                405                 410                 415

Gly Leu Phe Glu Phe Tyr Lys Leu Leu Cys Val Arg Gly Ile Ile Pro
            420                 425                 430

Phe Lys Thr Lys Ser Leu Asp Glu Gly Tyr Asn Lys Ala Leu Asn Tyr
        435                 440                 445

Leu Cys Ile Lys Val Asn Asn Trp Asp Leu Phe Phe Ser Pro Ser Glu
    450                 455                 460

Asp Asn Phe Thr Asn Asp Leu Asp Lys Val Glu Glu Ile Thr Ala Asp
465                 470                 475                 480

Thr Asn Ile Glu Ala Ala Glu Glu Asn Ile Ser Ser Asp Leu Ile Gln
                485                 490                 495

Gln Tyr Tyr Leu Thr Phe Asp Phe Asp Asn Glu Pro Glu Asn Ile Ser
            500                 505                 510

Ile Glu Asn Leu Ser Ser Asp Ile Ile Gly Gln Leu Glu Pro Met Pro
        515                 520                 525

Asn Ile Glu Arg Phe Pro Asn Gly Lys Lys Tyr Glu Leu Asp Lys Tyr
    530                 535                 540

Thr Met Phe His Tyr Leu Arg Ala Gln Glu Phe Glu His Gly Asp Ser
545                 550                 555                 560

Arg Ile Ile Leu Thr Asn Ser Ala Glu Glu Ala Leu Leu Lys Pro Asn
                565                 570                 575

Val Ala Tyr Thr Phe Phe Ser Ser Lys Tyr Val Lys Lys Ile Asn Lys
            580                 585                 590

Ala Val Glu Ala Val Ile Phe Leu Ser Trp Ala Glu Glu Leu Val Tyr
        595                 600                 605

Asp Phe Thr Asp Glu Thr Asn Glu Val Thr Thr Met Asp Lys Ile Ala
    610                 615                 620

Asp Ile Thr Ile Ile Val Pro Tyr Ile Gly Pro Ala Leu Asn Ile Gly
625                 630                 635                 640

Asn Met Val Ser Lys Gly Glu Phe Val Glu Ala Ile Leu Phe Thr Gly
                645                 650                 655

Val Val Ala Leu Leu Glu Phe Ile Pro Glu Tyr Ser Leu Pro Val Phe
            660                 665                 670

Gly Thr Phe Ala Ile Val Ser Tyr Ile Ala Asn Lys Val Leu Thr Val
        675                 680                 685

Gln Thr Ile Asn Asn Ala Leu Ser Lys Arg Asn Glu Lys Trp Asp Glu
    690                 695                 700

Val Tyr Lys Tyr Thr Val Thr Asn Trp Leu Ala Lys Val Asn Thr Gln
705                 710                 715                 720

Ile Asp Leu Ile Arg Glu Lys Met Lys Lys Ala Leu Glu Asn Gln Ala
                725                 730                 735

Glu Ala Thr Arg Ala Ile Ile Asn Tyr Gln Tyr Asn Gln Tyr Thr Glu
            740                 745                 750

Glu Glu Lys Asn Asn Ile Asn Phe Asn Ile Asp Asp Leu Ser Ser Lys
        755                 760                 765

Leu Asn Arg Ser Ile Asn Arg Ala Met Ile Asn Ile Asn Lys Phe Leu
    770                 775                 780
```

```
Asp Gln Cys Ser Val Ser Tyr Leu Met Asn Ser Met Ile Pro Tyr Ala
785                 790                 795                 800

Val Lys Arg Leu Lys Asp Phe Asp Ala Ser Val Arg Asp Val Leu Leu
                805                 810                 815

Lys Tyr Ile Tyr Asp Asn Arg Gly Thr Leu Ile Leu Gln Val Asp Arg
            820                 825                 830

Leu Lys Asp Glu Val Asn Asn Thr Leu Ser Ala Asp Ile Pro Phe Gln
        835                 840                 845

Leu Ser Lys Tyr Val Asn Asp Lys Lys Leu Leu Ser Thr Phe Thr Glu
    850                 855                 860

Tyr Ile Lys Asn Ile Val Asn Thr Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095

Asp Phe  Trp Gly Asn Pro Leu  Met Tyr Asn Lys Glu  Tyr Tyr Met
    1100                1105                1110

Phe Asn  Ala Gly Asn Lys Asn  Ser Tyr Ile Lys Leu  Lys Lys Asp
    1115                1120                1125

Ser Pro  Val Gly Glu Ile Leu  Thr Arg Ser Lys Tyr  Asn Gln Asn
    1130                1135                1140

Ser Lys  Tyr Ile Asn Tyr Arg  Asp Leu Tyr Ile Gly  Glu Lys Phe
    1145                1150                1155

Ile Ile  Arg Arg Lys Ser Asn  Ser Gln Ser Ile Asn  Asp Asp Ile
    1160                1165                1170

Val Arg  Lys Glu Asp Tyr Ile  Tyr Leu Asp Phe Phe  Asn Leu Asn
    1175                1180                1185
```

```
Gln Glu  Trp Arg Val Tyr Thr  Tyr Lys Tyr Phe Lys  Lys Glu Glu
    1190                 1195                 1200

Glu Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Ile Val Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300
```

```
<210> SEQ ID NO 20
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 20

Met Pro Leu Val Asn Gln Gln Ile Asn Tyr Tyr Asp Pro Val Asn Gly
1               5                   10                  15

Val Asp Ile Ala Tyr Ile Lys Ile Pro Asn Ala Gly Lys Met Gln Pro
            20                  25                  30

Val Lys Ala Phe Lys Ile His Asn Lys Val Trp Val Ile Pro Glu Arg
        35                  40                  45

Asp Ile Phe Thr Asn Pro Glu Glu Val Asp Leu Asn Pro Pro Pro Glu
    50                  55                  60

Ala Lys Gln Val Pro Ile Ser Tyr Tyr Asp Ser Ala Tyr Leu Ser Thr
65                  70                  75                  80

Asp Asn Glu Lys Asp Asn Tyr Leu Lys Gly Val Ile Lys Leu Phe Glu
                85                  90                  95

Arg Ile Tyr Ser Thr Asp Leu Gly Arg Met Leu Leu Ile Ser Ile Val
            100                 105                 110

Arg Gly Ile Pro Phe Trp Gly Gly Gly Lys Ile Asp Thr Glu Leu Lys
        115                 120                 125

Val Ile Asp Thr Asn Cys Ile Asn Ile Ile Gln Leu Asp Asp Ser Tyr
    130                 135                 140

Arg Ser Glu Glu Leu Asn Leu Ala Ile Ile Gly Pro Ser Ala Asn Ile
145                 150                 155                 160

Ile Glu Ser Gln Cys Ser Ser Phe Arg Asp Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Val Gly Phe Glu Glu Ser Leu Glu Val Asp Thr Asn Pro Leu Leu
        195                 200                 205

Gly Ala Gly Lys Phe Ala Gln Asp Pro Ala Val Ala Leu Ala His Glu
    210                 215                 220

Leu Ile His Ala Glu His Arg Leu Tyr Gly Ile Ala Ile Asn Thr Asn
225                 230                 235                 240
```

```
Arg Val Phe Lys Val Asn Thr Asn Ala Tyr Tyr Glu Met Ala Gly Leu
                245                 250                 255

Glu Val Ser Leu Glu Glu Leu Ile Thr Phe Gly Gly Asn Asp Ala Lys
            260                 265                 270

Phe Ile Asp Ser Leu Gln Lys Lys Glu Phe Ser Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Ala Thr Gly Lys Phe Leu Val Asp Arg Leu
                325                 330                 335

Lys Phe Asp Glu Leu Tyr Lys Leu Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Asp Val Asn Tyr
    370                 375                 380

Thr Ile His Asp Gly Phe Asn Leu Arg Asn Thr Asn Leu Ala Ala Asn
385                 390                 395                 400

Phe Asn Gly Gln Asn Ile Glu Ile Asn Asn Lys Asn Phe Asp Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Glu Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Asn Phe Asn Phe Asp Asn Glu Pro
            500                 505                 510

Glu Asn Thr Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asn Lys Tyr Thr Met Phe His Tyr Leu Arg Ala Gln Glu Phe Lys
545                 550                 555                 560

His Ser Asn Ser Arg Ile Ile Leu Thr Asn Ser Ala Lys Glu Ala Leu
                565                 570                 575

Leu Lys Pro Asn Ile Val Tyr Thr Phe Phe Ser Ser Lys Tyr Ile Lys
            580                 585                 590

Ala Ile Asn Lys Ala Val Glu Ala Val Thr Phe Val Asn Trp Ile Glu
        595                 600                 605

Asn Leu Val Tyr Asp Phe Thr Asp Glu Thr Asn Glu Val Ser Thr Met
    610                 615                 620

Asp Lys Ile Ala Asp Ile Thr Ile Val Ile Pro Tyr Ile Gly Pro Ala
625                 630                 635                 640

Leu Asn Ile Gly Asn Met Ile Tyr Lys Gly Glu Phe Val Glu Ala Ile
                645                 650                 655

Ile Phe Ser Gly Ala Val Ile Leu Leu Glu Ile Val Pro Glu Ile Ala
```

```
            660                 665                 670

Leu Pro Val Leu Gly Thr Phe Ala Leu Val Ser Tyr Val Ser Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Ile
705                 710                 715                 720

Val Asn Thr Gln Ile Asn Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Ile Gly
            820                 825                 830

Gln Val Asn Arg Leu Lys Asp Lys Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080
```

```
Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Glu Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Ile Val Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300


<210> SEQ ID NO 21
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 21

Met Leu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Glu Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125
```

```
Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Glu His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Glu Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540
```

-continued

```
Leu Asp Lys Tyr Thr Met Phe His Tyr Leu Arg Ala Gln Glu Phe Glu
545                 550                 555                 560

His Gly Lys Ser Arg Ile Val Leu Thr Asn Ser Val Asn Glu Ala Leu
                565                 570                 575

Leu Asn Pro Ser Ser Val Tyr Thr Phe Phe Ser Ser Asp Tyr Val Arg
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Gly Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Gly Asp
        755                 760                 765

Leu Ser Ser Lys Leu Asn Asp Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
```

```
                965                  970                  975

Ile Ser Ile Arg Gly Asn Arg Ile Ile Trp Thr Leu Ile Asp Ile Asn
            980                  985                  990

Gly Lys Thr Lys Ser Val Phe Phe  Glu Tyr Asn Ile Arg  Glu Asp Ile
        995                  1000                 1005

Ser Glu  Tyr Ile Asn Arg Trp  Phe Phe Val Thr Ile  Thr Asn Asn
    1010                 1015                 1020

Leu Asn  Asn Ala Lys Ile Tyr  Ile Asn Gly Lys Leu  Glu Ser Asn
    1025                 1030                 1035

Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Glu Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Ile Val Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300


<210> SEQ ID NO 22
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 22

Met Pro Phe Val Asn Lys Gln Phe Asn Tyr Lys Asp Pro Val Asn Gly
```

```
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Ala Lys Leu
                405                 410                 415

Lys Asn Phe Thr Gly Leu Phe Glu Phe Tyr Lys Leu Leu Cys Val Arg
            420                 425                 430
```

```
Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Ser Ala Gln Glu Phe Glu
545                 550                 555                 560

His Gly Lys Ser Arg Ile Asp Leu Thr Asn Ser Val Asn Glu Ala Leu
                565                 570                 575

Leu Asn Pro Ser His Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Ile Val Ser Tyr Ile Ala Asn Lys
        675                 680                 685

Val Leu Thr Val Gln Thr Ile Asn Asn Ala Leu Ser Lys Arg Asn Glu
    690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845
```

```
Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095

Asp Phe  Trp Gly Asn Pro Leu  Met Tyr Asn Lys Glu  Tyr Tyr Met
    1100                1105                1110

Phe Asn  Ala Gly Asn Lys Asn  Ser Tyr Ile Lys Leu  Lys Lys Asp
    1115                1120                1125

Ser Pro  Val Gly Glu Ile Leu  Thr Arg Ser Lys Tyr  Asn Gln Asn
    1130                1135                1140

Ser Lys  Tyr Ile Asn Tyr Arg  Asp Leu Tyr Ile Gly  Glu Lys Phe
    1145                1150                1155

Ile Ile  Arg Arg Lys Ser Asn  Ser Gln Ser Ile Asn  Asp Asp Ile
    1160                1165                1170

Val Arg  Lys Glu Asp Tyr Ile  Tyr Leu Asp Phe Phe  Asn Leu Asn
    1175                1180                1185

Gln Glu  Trp Arg Val Tyr Thr  Tyr Lys Tyr Phe Lys  Lys Glu Glu
    1190                1195                1200

Glu Lys  Leu Phe Leu Ala Pro  Ile Ser Asp Ser Asp  Glu Phe Tyr
    1205                1210                1215

Asn Thr  Ile Gln Ile Lys Glu  Tyr Asp Glu Gln Pro  Thr Tyr Ser
    1220                1225                1230

Cys Gln  Leu Leu Phe Lys Lys  Asp Glu Glu Ser Thr  Asp Glu Ile
    1235                1240                1245

Gly Leu  Ile Gly Ile His Arg  Phe Tyr Glu Ser Gly  Ile Val Phe
```

```
    1250                1255                1260

Glu Glu  Tyr Lys Asp Tyr Phe  Cys Ile Ser Lys Trp  Tyr Leu Lys
    1265                1270                1275

Glu Val  Lys Arg Lys Pro Tyr  Asn Leu Lys Leu Gly  Cys Asn Trp
    1280                1285                1290

Gln Phe  Ile Pro Lys Asp Glu  Gly Trp Thr Glu
    1295                1300


<210> SEQ ID NO 23
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 23

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Ile Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Asn Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Ile Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Glu Val Ala Ser Ile Leu Asn Lys Ala Lys Ser Ile Ile
    290                 295                 300

Gly Thr Thr Ala Ser Leu Gln Tyr Met Lys Asn Val Phe Lys Glu Lys
```

```
305                 310                 315                 320

Tyr Leu Leu Ser Glu Asp Thr Ser Gly Lys Phe Ser Val Asp Lys Leu
                325                 330                 335

Arg Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Met Asn Ile Val Pro Glu Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Ser
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

Tyr Gly Asn Ser Arg Ile Val Leu Ile Asn Ser Val Asn Glu Ala Leu
                565                 570                 575

Leu Asn Pro Ser Ser Val Tyr Thr Phe Phe Ser Ser Asp Tyr Val Lys
            580                 585                 590

Lys Ala Asn Glu Ala Thr Glu Ala Ala Met Phe Leu Gly Trp Val Glu
        595                 600                 605

Gln Leu Val Tyr Asp Phe Thr Asp Glu Thr Ser Glu Val Ser Thr Met
    610                 615                 620

Asp Lys Ile Ala Asp Ile Thr Ile Ile Val Pro Tyr Ile Gly Pro Ala
625                 630                 635                 640

Leu Asn Ile Gly Asn Met Val Tyr Lys Lys Lys Phe Glu Glu Ala Leu
                645                 650                 655

Ile Phe Ser Gly Ala Val Ile Leu Leu Glu Phe Val Pro Glu Ile Val
            660                 665                 670

Leu Pro Ile Leu Gly Thr Phe Ala Leu Val Ser Tyr Thr Ser Asn Lys
        675                 680                 685

Val Leu Thr Val Arg Thr Ile Asp Asn Ala Leu Ser Lys Arg Asn Glu
    690                 695                 700

Lys Trp Glu Glu Val Tyr Lys Tyr Ile Val Thr Asn Trp Leu Ala Lys
705                 710                 715                 720

Val Asn Thr Gln Ile Asn Leu Ile Arg Lys Lys Met Lys Glu Ala Leu
                725                 730                 735
```

```
Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Gly Asp
        755                 760                 765

Leu Ser Ser Lys Leu Asn Asp Ser Ile Asn Lys Ala Met Ile Asn Ile
    770                 775                 780

Asn Lys Phe Leu Asp Gln Cys Ser Val Ser Tyr Leu Met Asn Ser Met
785                 790                 795                 800

Ile Pro Gln Gly Val Lys Gln Leu Lys Asp Phe Asp Thr Ser Leu Arg
                805                 810                 815

Asp Ser Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Ala Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095

Asp Phe  Trp Gly Asn Pro Leu  Met Tyr Asn Lys Glu  Tyr Tyr Met
    1100                1105                1110

Phe Asn  Ala Gly Asn Lys Asn  Ser Tyr Ile Lys Leu  Lys Lys Asp
    1115                1120                1125

Ser Pro  Val Gly Glu Ile Leu  Thr Arg Ser Lys Tyr  Asn Gln Asn
    1130                1135                1140
```

```
Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Glu Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Ile Val Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300


<210> SEQ ID NO 24
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 24

Met Pro Phe Val Asn Lys Gln Phe Asn Tyr Lys Asp Thr Val Asn Gly
1               5                   10                  15

Ile Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Lys Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190
```

-continued

```
Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asn Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Asp Glu Asn Tyr
    370                 375                 380

Thr Ile Lys Asp Gly Phe Asn Leu Lys Asn Thr Asn Leu Ala Ala Asn
385                 390                 395                 400

Phe Asn Gly Gln Asn Thr Glu Ile Asn Ser Arg Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Pro Phe Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asp Phe Asp Asn Glu Pro
            500                 505                 510

Glu Asn Ile Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Ser Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
```

```
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Val Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Thr Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Glu Val Leu Leu Lys Tyr Ile Tyr Asp Asn Arg Gly Thr Leu Ile Leu
            820                 825                 830

Gln Val Asp Arg Leu Lys Asp Lys Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035
```

```
Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Glu Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Ile Val Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300
```

```
<210> SEQ ID NO 25
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 25

Glu Ser Gly Ile Val Phe Glu Glu
1               5


<210> SEQ ID NO 26
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 26

Glu Ser Gly Ile Val Leu Lys Asp
```

1 5

<210> SEQ ID NO 27
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 27

Glu Ser Gly Ile Val Phe Lys Asp
1 5

<210> SEQ ID NO 28
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 28

Glu Ser Gly Val Leu Arg Lys Lys
1 5

<210> SEQ ID NO 29
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 29

Glu Ser Gly Ile Val Phe Lys Glu
1 5

<210> SEQ ID NO 30
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 30

Glu Ser Gly Ile Val Phe Lys Asp
1 5

<210> SEQ ID NO 31
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 31

Glu Ser Gly Ile Leu Phe Lys Asp
1 5

<210> SEQ ID NO 32
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 32

Glu Ser Gly Phe Val Phe Gln Glu
1 5

<210> SEQ ID NO 33
<211> LENGTH: 1291
<212> TYPE: PRT
<213> ORGANISM: Artificial Sequence
<220> FEATURE:
<223> OTHER INFORMATION: Synthetic Polypeptide

<400> SEQUENCE: 33

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365
```

```
Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780
```

```
Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                1015                1020

Ser Asn  Thr Asp Ile Lys Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Arg Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
    1115                1120                1125

Gln Asn  Ser Lys Tyr Ile Asn  Tyr Arg Asp Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Leu Asn  Gln Glu Trp Arg Val  Tyr Thr Tyr Lys Tyr  Phe Lys Lys
    1175                1180                1185

Glu Glu  Glu Lys Leu Phe Leu  Ala Pro Ile Ser Asp  Ser Asp Glu
```

```
    1190                1195                1200

Phe Tyr  Asn Thr Ile Gln Ile  Lys Glu Tyr Asp Glu  Gln Pro Thr
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Arg Phe Tyr Glu  Ser Gly Trp
    1235                1240                1245

Trp Phe  Glu Glu Tyr Lys Asp  Tyr Phe Cys Ile Ser  Lys Trp Tyr
    1250                1255                1260

Leu Lys  Glu Val Lys Arg Lys  Pro Tyr Asn Leu Lys  Leu Gly Cys
    1265                1270                1275

Asn Trp  Gln Phe Ile Pro Lys  Asp Glu Gly Trp Thr  Glu
    1280                1285                1290


<210> SEQ ID NO 34
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 34

Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
```

```
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Thr Tyr Lys Tyr Phe Lys Lys Glu Glu Glu Lys Leu Phe Leu
                325                 330                 335

Ala Pro Ile Ser Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Trp Trp Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430


<210> SEQ ID NO 35
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 35

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
```

```
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620
```

```
Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035
```

```
Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Glu Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Trp Trp Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300


<210> SEQ ID NO 36
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 36

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80
```

```
Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Val Ala Ser Thr Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Asn Phe Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
                405                 410                 415

Lys Asn Phe Thr Gly Leu Phe Glu Phe Tyr Lys Leu Leu Cys Val Arg
            420                 425                 430

Gly Ile Ile Pro Phe Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480

Ile Thr Ala Asp Thr Asn Ile Glu Ala Ala Glu Glu Asn Ile Ser Leu
                485                 490                 495

Asp Leu Ile Gln Gln Tyr Tyr Leu Thr Phe Asp Phe Asp Asn Glu Pro
```

```
            500                 505                 510

Glu Asn Ile Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Asp Ser Arg Ile Ile Leu Thr Asn Ser Ala Glu Glu Ala Leu
                565                 570                 575

Leu Lys Pro Asn Val Ala Tyr Thr Phe Phe Ser Ser Lys Tyr Val Lys
            580                 585                 590

Lys Ile Asn Lys Ala Val Glu Ala Phe Met Phe Leu Asn Trp Ala Glu
        595                 600                 605

Glu Leu Val Tyr Asp Phe Thr Asp Glu Thr Asn Glu Val Thr Thr Met
    610                 615                 620

Asp Lys Ile Ala Asp Ile Thr Ile Ile Val Pro Tyr Ile Gly Pro Ala
625                 630                 635                 640

Leu Asn Ile Gly Asn Met Leu Ser Lys Gly Glu Phe Val Glu Ala Ile
                645                 650                 655

Ile Phe Thr Gly Val Val Ala Met Leu Glu Phe Ile Pro Glu Tyr Ala
            660                 665                 670

Leu Pro Val Phe Gly Thr Phe Ala Ile Val Ser Tyr Ile Ala Asn Lys
        675                 680                 685

Val Leu Thr Val Gln Thr Ile Asn Asn Ala Leu Ser Lys Arg Asn Glu
    690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Val Leu
            820                 825                 830

Gln Val Asp Arg Leu Lys Asp Glu Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925
```

```
Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                 1015                 1020

Leu Asn  Asn Ala Lys Ile Tyr  Ile Asn Gly Lys Leu  Glu Ser Asn
    1025                 1030                 1035

Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Glu Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Trp Trp Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300
```

<210> SEQ ID NO 37
<211> LENGTH: 8

<212> TYPE: PRT
<213> ORGANISM: Artificial Sequence
<220> FEATURE:
<223> OTHER INFORMATION: Synthetic Polypeptide

<400> SEQUENCE: 37

```
Glu Ser Gly Trp Trp Phe Glu Glu
1               5
```

<210> SEQ ID NO 38
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 38

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320
```

```
Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735
```

```
Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn
865                 870


<210> SEQ ID NO 39
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 39

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220
```

```
Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Val Ala Ser Thr Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Asn Phe Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
                405                 410                 415

Lys Asn Phe Thr Gly Leu Phe Glu Phe Tyr Lys Leu Leu Cys Val Arg
            420                 425                 430

Gly Ile Ile Pro Phe Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480

Ile Thr Ala Asp Thr Asn Ile Glu Ala Ala Glu Glu Asn Ile Ser Leu
                485                 490                 495

Asp Leu Ile Gln Gln Tyr Tyr Leu Thr Phe Asp Phe Asp Asn Glu Pro
            500                 505                 510

Glu Asn Ile Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Asp Ser Arg Ile Ile Leu Thr Asn Ser Ala Glu Glu Ala Leu
                565                 570                 575

Leu Lys Pro Asn Val Ala Tyr Thr Phe Phe Ser Ser Lys Tyr Val Lys
            580                 585                 590

Lys Ile Asn Lys Ala Val Glu Ala Phe Met Phe Leu Asn Trp Ala Glu
        595                 600                 605

Glu Leu Val Tyr Asp Phe Thr Asp Glu Thr Asn Glu Val Thr Thr Met
    610                 615                 620

Asp Lys Ile Ala Asp Ile Thr Ile Ile Val Pro Tyr Ile Gly Pro Ala
625                 630                 635                 640

Leu Asn Ile Gly Asn Met Leu Ser Lys Gly Glu Phe Val Glu Ala Ile
```

```
                645                 650                 655

Ile Phe Thr Gly Val Val Ala Met Leu Glu Phe Ile Pro Glu Tyr Ala
            660                 665                 670

Leu Pro Val Phe Gly Thr Phe Ala Ile Val Ser Tyr Ile Ala Asn Lys
        675                 680                 685

Val Leu Thr Val Gln Thr Ile Asn Asn Ala Leu Ser Lys Arg Asn Glu
    690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Val Leu
            820                 825                 830

Gln Val Asp Arg Leu Lys Asp Glu Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn
865                 870


<210> SEQ ID NO 40
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 40

Met Pro Phe Val Asn Lys Pro Phe Asn Tyr Arg Asp Pro Gly Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Glu Gly Val Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Ile Lys Leu Phe Asp
                85                  90                  95

Arg Ile Tyr Ser Thr Gly Leu Gly Arg Met Leu Leu Ser Phe Ile Val
            100                 105                 110

Lys Gly Ile Pro Phe Trp Gly Gly Ser Thr Ile Asp Thr Glu Leu Lys
        115                 120                 125

Val Ile Asp Thr Asn Cys Ile Asn Val Ile Glu Pro Gly Gly Ser Tyr
```

-continued

```
        130                 135                 140

Arg Ser Glu Glu Leu Asn Leu Val Ile Thr Gly Pro Ser Ala Asp Ile
145                 150                 155                 160

Ile Gln Phe Glu Cys Lys Ser Phe Gly His Asp Val Phe Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Thr Phe Ala Thr Asp Pro Ala Val Thr Leu Ala His Glu
    210                 215                 220

Leu Ile His Ala Ala His Arg Leu Tyr Gly Ile Ala Ile Asn Pro Asn
225                 230                 235                 240

Arg Val Leu Lys Val Lys Thr Asn Ala Tyr Tyr Glu Met Ser Gly Leu
                245                 250                 255

Glu Val Ser Phe Glu Glu Leu Arg Thr Phe Gly Gly Asn Asp Thr Asn
            260                 265                 270

Phe Ile Asp Ser Leu Trp Gln Lys Lys Phe Ser Arg Asp Ala Tyr Asp
        275                 280                 285

Asn Leu Gln Asn Ile Ala Arg Ile Leu Asn Glu Ala Lys Thr Ile Val
    290                 295                 300

Gly Thr Thr Thr Pro Leu Gln Tyr Met Lys Asn Ile Phe Ile Arg Lys
305                 310                 315                 320

Tyr Phe Leu Ser Glu Asp Ala Ser Gly Lys Ile Ser Val Asn Lys Ala
                325                 330                 335

Ala Phe Lys Glu Phe Tyr Arg Val Leu Thr Arg Gly Phe Thr Glu Leu
            340                 345                 350

Glu Phe Val Asn Pro Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380

Thr Ile Asn Glu Gly Phe Asn Leu Glu Gly Ala Asn Ser Asn Gly Gln
385                 390                 395                 400

Asn Thr Glu Ile Asn Ser Arg Asn Phe Thr Arg Leu Lys Asn Phe Thr
                405                 410                 415

Gly Leu Phe Glu Phe Tyr Lys Leu Leu Cys Val Arg Gly Ile Ile Pro
            420                 425                 430

Phe Lys Thr Lys Ser Leu Asp Glu Gly Tyr Asn Lys Ala Leu Asn Tyr
        435                 440                 445

Leu Cys Ile Lys Val Asn Asn Trp Asp Leu Phe Phe Ser Pro Ser Glu
    450                 455                 460

Asp Asn Phe Thr Asn Asp Leu Asp Lys Val Glu Glu Ile Thr Ala Asp
465                 470                 475                 480

Thr Asn Ile Glu Ala Ala Glu Glu Asn Ile Ser Ser Asp Leu Ile Gln
                485                 490                 495

Gln Tyr Tyr Leu Thr Phe Asp Phe Asp Asn Glu Pro Glu Asn Ile Ser
            500                 505                 510

Ile Glu Asn Leu Ser Ser Asp Ile Ile Gly Gln Leu Glu Pro Met Pro
        515                 520                 525

Asn Ile Glu Arg Phe Pro Asn Gly Lys Lys Tyr Glu Leu Asp Lys Tyr
    530                 535                 540

Thr Met Phe His Tyr Leu Arg Ala Gln Glu Phe Glu His Gly Asp Ser
545                 550                 555                 560
```

```
Arg Ile Ile Leu Thr Asn Ser Ala Glu Glu Ala Leu Leu Lys Pro Asn
                565                 570                 575

Val Ala Tyr Thr Phe Phe Ser Ser Lys Tyr Val Lys Lys Ile Asn Lys
            580                 585                 590

Ala Val Glu Ala Val Ile Phe Leu Ser Trp Ala Glu Glu Leu Val Tyr
        595                 600                 605

Asp Phe Thr Asp Glu Thr Asn Glu Val Thr Thr Met Asp Lys Ile Ala
    610                 615                 620

Asp Ile Thr Ile Ile Val Pro Tyr Ile Gly Pro Ala Leu Asn Ile Gly
625                 630                 635                 640

Asn Met Val Ser Lys Gly Glu Phe Val Glu Ala Ile Leu Phe Thr Gly
                645                 650                 655

Val Val Ala Leu Leu Glu Phe Ile Pro Glu Tyr Ser Leu Pro Val Phe
            660                 665                 670

Gly Thr Phe Ala Ile Val Ser Tyr Ile Ala Asn Lys Val Leu Thr Val
        675                 680                 685

Gln Thr Ile Asn Asn Ala Leu Ser Lys Arg Asn Glu Lys Trp Asp Glu
    690                 695                 700

Val Tyr Lys Tyr Thr Val Thr Asn Trp Leu Ala Lys Val Asn Thr Gln
705                 710                 715                 720

Ile Asp Leu Ile Arg Glu Lys Met Lys Lys Ala Leu Glu Asn Gln Ala
                725                 730                 735

Glu Ala Thr Arg Ala Ile Ile Asn Tyr Gln Tyr Asn Gln Tyr Thr Glu
            740                 745                 750

Glu Glu Lys Asn Asn Ile Asn Phe Asn Ile Asp Asp Leu Ser Ser Lys
        755                 760                 765

Leu Asn Arg Ser Ile Asn Arg Ala Met Ile Asn Ile Asn Lys Phe Leu
    770                 775                 780

Asp Gln Cys Ser Val Ser Tyr Leu Met Asn Ser Met Ile Pro Tyr Ala
785                 790                 795                 800

Val Lys Arg Leu Lys Asp Phe Asp Ala Ser Val Arg Asp Val Leu Leu
                805                 810                 815

Lys Tyr Ile Tyr Asp Asn Arg Gly Thr Leu Ile Leu Gln Val Asp Arg
            820                 825                 830

Leu Lys Asp Glu Val Asn Asn Thr Leu Ser Ala Asp Ile Pro Phe Gln
        835                 840                 845

Leu Ser Lys Tyr Val Asn Asp Lys Lys Leu Leu Ser Thr Phe Thr Glu
    850                 855                 860

Tyr Ile Lys Asn Ile Val Asn Thr
865                 870
```

<210> SEQ ID NO 41
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 41

```
Met Pro Leu Val Asn Gln Gln Ile Asn Tyr Tyr Asp Pro Val Asn Gly
1               5                   10                  15

Val Asp Ile Ala Tyr Ile Lys Ile Pro Asn Ala Gly Lys Met Gln Pro
            20                  25                  30

Val Lys Ala Phe Lys Ile His Asn Lys Val Trp Val Ile Pro Glu Arg
        35                  40                  45
```

```
Asp Ile Phe Thr Asn Pro Glu Glu Val Asp Leu Asn Pro Pro Pro Glu
    50                  55                  60

Ala Lys Gln Val Pro Ile Ser Tyr Tyr Asp Ser Ala Tyr Leu Ser Thr
65                  70                  75                  80

Asp Asn Glu Lys Asp Asn Tyr Leu Lys Gly Val Ile Lys Leu Phe Glu
                85                  90                  95

Arg Ile Tyr Ser Thr Asp Leu Gly Arg Met Leu Leu Ile Ser Ile Val
            100                 105                 110

Arg Gly Ile Pro Phe Trp Gly Gly Gly Lys Ile Asp Thr Glu Leu Lys
        115                 120                 125

Val Ile Asp Thr Asn Cys Ile Asn Ile Ile Gln Leu Asp Asp Ser Tyr
    130                 135                 140

Arg Ser Glu Glu Leu Asn Leu Ala Ile Ile Gly Pro Ser Ala Asn Ile
145                 150                 155                 160

Ile Glu Ser Gln Cys Ser Ser Phe Arg Asp Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Val Gly Phe Glu Glu Ser Leu Glu Val Asp Thr Asn Pro Leu Leu
        195                 200                 205

Gly Ala Gly Lys Phe Ala Gln Asp Pro Ala Val Ala Leu Ala His Glu
    210                 215                 220

Leu Ile His Ala Glu His Arg Leu Tyr Gly Ile Ala Ile Asn Thr Asn
225                 230                 235                 240

Arg Val Phe Lys Val Asn Thr Asn Ala Tyr Tyr Glu Met Ala Gly Leu
                245                 250                 255

Glu Val Ser Leu Glu Glu Leu Ile Thr Phe Gly Gly Asn Asp Ala Lys
            260                 265                 270

Phe Ile Asp Ser Leu Gln Lys Lys Glu Phe Ser Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Ala Thr Gly Lys Phe Leu Val Asp Arg Leu
                325                 330                 335

Lys Phe Asp Glu Leu Tyr Lys Leu Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Asp Val Asn Tyr
    370                 375                 380

Thr Ile His Asp Gly Phe Asn Leu Arg Asn Thr Asn Leu Ala Ala Asn
385                 390                 395                 400

Phe Asn Gly Gln Asn Ile Glu Ile Asn Asn Lys Asn Phe Asp Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Glu Leu Cys Ile Lys Val Asn Asn Trp Asp Leu Phe Phe
    450                 455                 460
```

```
Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Asn Phe Asn Phe Asp Asn Glu Pro
            500                 505                 510

Glu Asn Thr Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asn Lys Tyr Thr Met Phe His Tyr Leu Arg Ala Gln Glu Phe Lys
545                 550                 555                 560

His Ser Asn Ser Arg Ile Ile Leu Thr Asn Ser Ala Lys Glu Ala Leu
                565                 570                 575

Leu Lys Pro Asn Ile Val Tyr Thr Phe Phe Ser Ser Lys Tyr Ile Lys
            580                 585                 590

Ala Ile Asn Lys Ala Val Glu Ala Val Thr Phe Val Asn Trp Ile Glu
        595                 600                 605

Asn Leu Val Tyr Asp Phe Thr Asp Glu Thr Asn Glu Val Ser Thr Met
    610                 615                 620

Asp Lys Ile Ala Asp Ile Thr Ile Val Ile Pro Tyr Ile Gly Pro Ala
625                 630                 635                 640

Leu Asn Ile Gly Asn Met Ile Tyr Lys Gly Glu Phe Val Glu Ala Ile
                645                 650                 655

Ile Phe Ser Gly Ala Val Ile Leu Leu Glu Ile Val Pro Glu Ile Ala
            660                 665                 670

Leu Pro Val Leu Gly Thr Phe Ala Leu Val Ser Tyr Val Ser Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Ile
705                 710                 715                 720

Val Asn Thr Gln Ile Asn Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Ile Gly
            820                 825                 830

Gln Val Asn Arg Leu Lys Asp Lys Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn
865                 870
```

```
<210> SEQ ID NO 42
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 42

Met Leu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Glu Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Glu His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Glu Val Asn Tyr
```

```
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Val Leu Thr Asn Ser Val Asn Glu Ala Leu
                565                 570                 575

Leu Asn Pro Ser Ser Val Tyr Thr Phe Phe Ser Ser Asp Tyr Val Arg
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Gly Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Gly Asp
        755                 760                 765

Leu Ser Ser Lys Leu Asn Asp Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800
```

```
Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn
865                 870


<210> SEQ ID NO 43
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 43

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285
```

```
Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Ala Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Ser Ala Gln Glu Phe Glu
545                 550                 555                 560

His Gly Lys Ser Arg Ile Asp Leu Thr Asn Ser Val Asn Glu Ala Leu
                565                 570                 575

Leu Asn Pro Ser His Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Ile Val Ser Tyr Ile Ala Asn Lys
        675                 680                 685

Val Leu Thr Val Gln Thr Ile Asn Asn Ala Leu Ser Lys Arg Asn Glu
    690                 695                 700
```

```
Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn
865                 870
```

<210> SEQ ID NO 44
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 44

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Ile Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Asn Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190
```

```
Thr Phe Gly Phe Glu Glu Ser Leu Glu Val Asp Thr Asn Pro Leu Leu
        195                 200                 205

Gly Ala Gly Lys Phe Ala Ile Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Glu Val Ala Ser Ile Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Arg Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Met Asn Ile Val Pro Glu Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Ser
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

Tyr Gly Asn Ser Arg Ile Val Leu Ile Asn Ser Val Asn Glu Ala Leu
                565                 570                 575

Leu Asn Pro Ser Ser Val Tyr Thr Phe Phe Ser Ser Asp Tyr Val Lys
            580                 585                 590

Lys Ala Asn Glu Ala Thr Glu Ala Ala Met Phe Leu Gly Trp Val Glu
        595                 600                 605

Gln Leu Val Tyr Asp Phe Thr Asp Glu Thr Ser Glu Val Ser Thr Met
```

```
    610                 615                 620

Asp Lys Ile Ala Asp Ile Thr Ile Ile Val Pro Tyr Ile Gly Pro Ala
625                 630                 635                 640

Leu Asn Ile Gly Asn Met Val Tyr Lys Lys Lys Phe Glu Glu Ala Leu
                645                 650                 655

Ile Phe Ser Gly Ala Val Ile Leu Leu Glu Phe Val Pro Glu Ile Val
            660                 665                 670

Leu Pro Ile Leu Gly Thr Phe Ala Leu Val Ser Tyr Thr Ser Asn Lys
        675                 680                 685

Val Leu Thr Val Arg Thr Ile Asp Asn Ala Leu Ser Lys Arg Asn Glu
    690                 695                 700

Lys Trp Glu Glu Val Tyr Lys Tyr Ile Val Thr Asn Trp Leu Ala Lys
705                 710                 715                 720

Val Asn Thr Gln Ile Asn Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Gly Asp
        755                 760                 765

Leu Ser Ser Lys Leu Asn Asp Ser Ile Asn Lys Ala Met Ile Asn Ile
    770                 775                 780

Asn Lys Phe Leu Asp Gln Cys Ser Val Ser Tyr Leu Met Asn Ser Met
785                 790                 795                 800

Ile Pro Gln Gly Val Lys Gln Leu Lys Asp Phe Asp Thr Ser Leu Arg
                805                 810                 815

Asp Ser Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Ala Asp Asn Gln Arg Leu Leu Ser
    850                 855                 860

Thr Phe Thr Glu Tyr Ile Lys Asn
865                 870


<210> SEQ ID NO 45
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 45

Met Pro Phe Val Asn Lys Gln Phe Asn Tyr Lys Asp Thr Val Asn Gly
1               5                   10                  15

Ile Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Lys Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
```

```
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asn Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Asp Glu Asn Tyr
    370                 375                 380

Thr Ile Lys Asp Gly Phe Asn Leu Lys Asn Thr Asn Leu Ala Ala Asn
385                 390                 395                 400

Phe Asn Gly Gln Asn Thr Glu Ile Asn Ser Arg Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Pro Phe Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asp Phe Asp Asn Glu Pro
            500                 505                 510

Glu Asn Ile Ser Ile Glu Asn Leu Ser Ser Asp Ile Ile Gly Gln Leu
        515                 520                 525
```

```
Glu Pro Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Ser Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Val Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Thr Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Glu Val Leu Leu Lys Tyr Ile Tyr Asp Asn Arg Gly Thr Leu Ile Leu
            820                 825                 830

Gln Val Asp Arg Leu Lys Asp Lys Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn
865                 870


<210> SEQ ID NO 46
<211> LENGTH: 1291
<212> TYPE: PRT
<213> ORGANISM: Artificial Sequence
<220> FEATURE:
<223> OTHER INFORMATION: Synthetic Polypeptide

<400> SEQUENCE: 46

Met Pro Val Thr Ile Asn Asn Phe Asn Tyr Asn Asp Pro Ile Asp Asn
1               5                   10                  15
```

```
Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430
```

```
Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
```

```
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                 1015                 1020

Ser Asn  Thr Asp Ile Lys Asp  Ile Arg Glu Val Ile  Ala Asn Gly
    1025                 1030                 1035

Glu Ile  Ile Phe Lys Leu Asp  Gly Asp Ile Asp Arg  Thr Gln Phe
    1040                 1045                 1050

Ile Trp  Met Lys Tyr Phe Ser  Ile Phe Asn Thr Glu  Leu Ser Gln
    1055                 1060                 1065

Ser Asn  Ile Glu Glu Arg Tyr  Lys Ile Gln Ser Tyr  Ser Glu Tyr
    1070                 1075                 1080

Leu Lys  Asp Phe Trp Gly Asn  Pro Leu Met Tyr Asn  Lys Glu Tyr
    1085                 1090                 1095

Tyr Met  Phe Asn Ala Gly Asn  Lys Asn Ser Tyr Ile  Lys Leu Lys
    1100                 1105                 1110

Lys Asp  Ser Pro Val Gly Glu  Ile Leu Thr Arg Ser  Lys Tyr Asn
    1115                 1120                 1125

Gln Asn  Ser Lys Tyr Ile Asn  Tyr Arg Asp Leu Tyr  Ile Gly Glu
    1130                 1135                 1140

Lys Phe  Ile Ile Arg Arg Lys  Ser Asn Ser Gln Ser  Ile Asn Asp
    1145                 1150                 1155

Asp Ile  Val Arg Lys Glu Asp  Tyr Ile Tyr Leu Asp  Phe Phe Asn
    1160                 1165                 1170

Leu Asn  Gln Glu Trp Arg Val  Tyr Thr Tyr Lys Tyr  Phe Lys Lys
    1175                 1180                 1185

Glu Glu  Met Lys Leu Phe Leu  Ala Pro Ile Tyr Asp  Ser Asp Glu
    1190                 1195                 1200

Phe Tyr  Asn Thr Ile Gln Ile  Lys Glu Tyr Asp Glu  Gln Pro Thr
    1205                 1210                 1215

Tyr Ser  Cys Gln Leu Leu Phe  Lys Lys Asp Glu Glu  Ser Thr Asp
    1220                 1225                 1230

Glu Ile  Gly Leu Ile Gly Ile  His Arg Phe Tyr Glu  Ser Gly Trp
    1235                 1240                 1245

Trp Phe  Glu Glu Tyr Lys Asp  Tyr Phe Cys Ile Ser  Lys Trp Tyr
    1250                 1255                 1260
```

```
Leu Lys  Glu Val Lys Arg Lys  Pro Tyr Asn Leu Lys  Leu Gly Cys
    1265                1270                1275

Asn Trp  Gln Phe Ile Pro Lys  Asp Glu Gly Trp Thr  Glu
    1280                1285                1290


<210> SEQ ID NO 47
<211> LENGTH: 1291
<212> TYPE: PRT
<213> ORGANISM: Artificial Sequence
<220> FEATURE:
<223> OTHER INFORMATION: Synthetic Polypeptide

<400> SEQUENCE: 47

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335
```

```
Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750
```

```
Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                1015                1020

Ser Asn  Thr Asp Ile Lys Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Arg Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
    1115                1120                1125

Gln Asn  Ser Lys Tyr Ile Asn  Tyr Arg Asp Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
```

```
    1160                1165                1170

Leu Asn  Gln Glu Trp Arg Val  Tyr Thr Tyr Lys Tyr  Phe Lys Lys
    1175                1180                1185

Glu Glu  Met Lys Leu Phe Leu  Ala Pro Ile Trp Asp  Ser Asp Glu
    1190                1195                1200

Phe Tyr  Asn Thr Ile Gln Ile  Lys Glu Tyr Asp Glu  Gln Pro Thr
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Arg Phe Tyr Glu  Ser Gly Trp
    1235                1240                1245

Trp Phe  Glu Glu Tyr Lys Asp  Tyr Phe Cys Ile Ser  Lys Trp Tyr
    1250                1255                1260

Leu Lys  Glu Val Lys Arg Lys  Pro Tyr Asn Leu Lys  Leu Gly Cys
    1265                1270                1275

Asn Trp  Gln Phe Ile Pro Lys  Asp Glu Gly Trp Thr  Glu
    1280                1285                1290


<210> SEQ ID NO 48
<211> LENGTH: 1291
<212> TYPE: PRT
<213> ORGANISM: Artificial Sequence
<220> FEATURE:
<223> OTHER INFORMATION: Synthetic Polypeptide

<400> SEQUENCE: 48

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
```

```
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655
```

```
Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                 1015                 1020

Ser Asn  Thr Asp Ile Lys Asp  Ile Arg Glu Val Ile  Ala Asn Gly
    1025                 1030                 1035

Glu Ile  Ile Phe Lys Leu Asp  Gly Asp Ile Asp Arg  Thr Gln Phe
    1040                 1045                 1050

Ile Trp  Met Lys Tyr Phe Ser  Ile Phe Asn Thr Glu  Leu Ser Gln
    1055                 1060                 1065
```

```
Ser Asn  Ile Glu Glu Arg Tyr  Lys Ile Gln Ser Tyr  Ser Glu Tyr
    1070                 1075                 1080

Leu Lys  Asp Phe Trp Gly Asn  Pro Leu Met Tyr Asn  Lys Glu Tyr
    1085                 1090                 1095

Tyr Met  Phe Asn Ala Gly Asn  Lys Asn Ser Tyr Ile  Lys Leu Lys
    1100                 1105                 1110

Lys Asp  Ser Pro Val Gly Glu  Ile Leu Thr Arg Ser  Lys Tyr Asn
    1115                 1120                 1125

Gln Asn  Ser Lys Tyr Ile Asn  Tyr Arg Asp Leu Tyr  Ile Gly Glu
    1130                 1135                 1140

Lys Phe  Ile Ile Arg Arg Lys  Ser Asn Ser Gln Ser  Ile Asn Asp
    1145                 1150                 1155

Asp Ile  Val Arg Lys Glu Asp  Tyr Ile Tyr Leu Asp  Phe Phe Asn
    1160                 1165                 1170

Leu Asn  Gln Glu Gln Arg Val  Tyr Thr Tyr Lys Tyr  Phe Lys Lys
    1175                 1180                 1185

Glu Glu  Met Lys Leu Phe Leu  Ala Pro Ile Ser Asp  Ser Asp Glu
    1190                 1195                 1200

Phe Tyr  Asn Thr Ile Gln Ile  Lys Glu Tyr Asp Glu  Gln Pro Thr
    1205                 1210                 1215

Tyr Ser  Cys Gln Leu Leu Phe  Lys Lys Asp Glu Glu  Ser Thr Asp
    1220                 1225                 1230

Glu Ile  Gly Leu Ile Gly Ile  His Arg Phe Tyr Glu  Ser Gly Trp
    1235                 1240                 1245

Trp Phe  Glu Glu Tyr Lys Asp  Tyr Phe Cys Ile Ser  Lys Trp Tyr
    1250                 1255                 1260

Leu Lys  Glu Val Lys Arg Lys  Pro Tyr Asn Leu Lys  Leu Gly Cys
    1265                 1270                 1275

Asn Trp  Gln Phe Ile Pro Lys  Asp Glu Gly Trp Thr  Glu
    1280                 1285                 1290


<210> SEQ ID NO 49
<211> LENGTH: 1291
<212> TYPE: PRT
<213> ORGANISM: Artificial Sequence
<220> FEATURE:
<223> OTHER INFORMATION: Synthetic Polypeptide

<400> SEQUENCE: 49

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125
```

```
Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
```

```
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975
```

```
Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                 1005

Asn Asn  Leu Asn Asn Ala Lys  Ile Tyr Ile Asn Gly  Lys Leu Glu
    1010                 1015                 1020

Ser Asn  Thr Asp Ile Lys Asp  Ile Arg Glu Val Ile  Ala Asn Gly
    1025                 1030                 1035

Glu Ile  Ile Phe Lys Leu Asp  Gly Asp Ile Asp Arg  Thr Gln Phe
    1040                 1045                 1050

Ile Trp  Met Lys Tyr Phe Ser  Ile Phe Asn Thr Glu  Leu Ser Gln
    1055                 1060                 1065

Ser Asn  Ile Glu Glu Arg Tyr  Lys Ile Gln Ser Tyr  Ser Glu Tyr
    1070                 1075                 1080

Leu Lys  Asp Phe Trp Gly Asn  Pro Leu Met Tyr Asn  Lys Glu Tyr
    1085                 1090                 1095

Tyr Met  Phe Asn Ala Gly Asn  Lys Asn Ser Tyr Ile  Lys Leu Lys
    1100                 1105                 1110

Lys Asp  Ser Pro Val Gly Glu  Ile Leu Thr Arg Ser  Lys Tyr Asn
    1115                 1120                 1125

Gln Asn  Ser Lys Tyr Ile Asn  Tyr Arg Asp Leu Tyr  Ile Gly Glu
    1130                 1135                 1140

Lys Phe  Ile Ile Arg Arg Lys  Ser Asn Ser Gln Ser  Ile Asn Asp
    1145                 1150                 1155

Asp Ile  Val Arg Lys Glu Asp  Tyr Ile Tyr Leu Asp  Phe Phe Asn
    1160                 1165                 1170

Leu Asn  Gln Glu Trp Arg Val  Tyr Thr Tyr Lys Tyr  Phe Lys Lys
    1175                 1180                 1185

Glu Glu  Val Lys Leu Phe Leu  Ala Pro Ile Tyr Asp  Ser Asp Glu
    1190                 1195                 1200

Phe Tyr  Asn Thr Ile Gln Ile  Lys Glu Tyr Asp Glu  Gln Pro Thr
    1205                 1210                 1215

Tyr Ser  Cys Gln Leu Leu Phe  Lys Lys Asp Glu Glu  Ser Thr Asp
    1220                 1225                 1230

Glu Ile  Gly Leu Ile Gly Ile  His Arg Phe Tyr Glu  Ser Gly Trp
    1235                 1240                 1245

Trp Phe  Glu Glu Tyr Lys Asp  Tyr Phe Cys Ile Ser  Lys Trp Tyr
    1250                 1255                 1260

Leu Lys  Glu Val Lys Arg Lys  Pro Tyr Asn Leu Lys  Leu Gly Cys
    1265                 1270                 1275

Asn Trp  Gln Phe Ile Pro Lys  Asp Glu Gly Trp Thr  Glu
    1280                 1285                 1290


<210> SEQ ID NO 50
<211> LENGTH: 1291
<212> TYPE: PRT
<213> ORGANISM: Artificial Sequence
<220> FEATURE:
<223> OTHER INFORMATION: Synthetic Polypeptide

<400> SEQUENCE: 50

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30
```

```
Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445
```

```
Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
```

```
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                1015                1020

Ser Asn  Thr Asp Ile Lys Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Arg Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
    1115                1120                1125

Gln Asn  Ser Lys Tyr Ile Asn  Tyr Arg Asp Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Leu Asn  Gln Glu Trp Arg Val  Tyr Thr Tyr Lys Tyr  Phe Lys Lys
    1175                1180                1185

Glu Glu  Val Lys Leu Phe Leu  Ala Pro Ile Trp Asp  Ser Asp Glu
    1190                1195                1200

Phe Tyr  Asn Thr Ile Gln Ile  Lys Glu Tyr Asp Glu  Gln Pro Thr
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Arg Phe Tyr Glu  Ser Gly Trp
    1235                1240                1245

Trp Phe  Glu Glu Tyr Lys Asp  Tyr Phe Cys Ile Ser  Lys Trp Tyr
    1250                1255                1260

Leu Lys  Glu Val Lys Arg Lys  Pro Tyr Asn Leu Lys  Leu Gly Cys
    1265                1270                1275
```

```
Asn Trp  Gln Phe Ile Pro Lys  Asp Glu Gly Trp Thr  Glu
    1280                 1285                 1290


<210> SEQ ID NO 51
<211> LENGTH: 1291
<212> TYPE: PRT
<213> ORGANISM: Artificial Sequence
<220> FEATURE:
<223> OTHER INFORMATION: Synthetic Polypeptide

<400> SEQUENCE: 51

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350
```

```
Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765
```

-continued

```
Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                1015                1020

Ser Asn  Thr Asp Ile Lys Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Arg Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
    1115                1120                1125

Gln Asn  Ser Lys Tyr Ile Asn  Tyr Arg Asp Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Leu Asn  Gln Glu Gln Arg Val  Tyr Thr Tyr Lys Tyr  Phe Lys Lys
```

```
    1175                1180                1185

Glu Glu  Val Lys Leu Phe Leu  Ala Pro Ile Ser Asp  Ser Asp Glu
    1190                1195                1200

Phe Tyr  Asn Thr Ile Gln Ile  Lys Glu Tyr Asp Glu  Gln Pro Thr
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Arg Phe Tyr Glu  Ser Gly Trp
    1235                1240                1245

Trp Phe  Glu Glu Tyr Lys Asp  Tyr Phe Cys Ile Ser  Lys Trp Tyr
    1250                1255                1260

Leu Lys  Glu Val Lys Arg Lys  Pro Tyr Asn Leu Lys  Leu Gly Cys
    1265                1270                1275

Asn Trp  Gln Phe Ile Pro Lys  Asp Glu Gly Trp Thr  Glu
    1280                1285                1290


<210> SEQ ID NO 52
<211> LENGTH: 1291
<212> TYPE: PRT
<213> ORGANISM: Artificial Sequence
<220> FEATURE:
<223> OTHER INFORMATION: Synthetic Polypeptide

<400> SEQUENCE: 52

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
```

-continued

```
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670
```

```
Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                 1005

Asn Asn  Leu Asn Asn Ala Lys  Ile Tyr Ile Asn Gly  Lys Leu Glu
    1010                 1015                 1020

Ser Asn  Thr Asp Ile Lys Asp  Ile Arg Glu Val Ile  Ala Asn Gly
    1025                 1030                 1035

Glu Ile  Ile Phe Lys Leu Asp  Gly Asp Ile Asp Arg  Thr Gln Phe
    1040                 1045                 1050

Ile Trp  Met Lys Tyr Phe Ser  Ile Phe Asn Thr Glu  Leu Ser Gln
    1055                 1060                 1065

Ser Asn  Ile Glu Glu Arg Tyr  Lys Ile Gln Ser Tyr  Ser Glu Tyr
    1070                 1075                 1080
```

```
Leu Lys  Asp Phe Trp Gly Asn  Pro Leu Met Tyr Asn  Lys Glu Tyr
    1085                 1090                 1095

Tyr Met  Phe Asn Ala Gly Asn  Lys Asn Ser Tyr Ile  Lys Leu Lys
    1100                 1105                 1110

Lys Asp  Ser Pro Val Gly Glu  Ile Leu Thr Arg Ser  Lys Tyr Asn
    1115                 1120                 1125

Gln Asn  Ser Lys Tyr Ile Asn  Tyr Arg Asp Leu Tyr  Ile Gly Glu
    1130                 1135                 1140

Lys Phe  Ile Ile Arg Arg Lys  Ser Asn Ser Gln Ser  Ile Asn Asp
    1145                 1150                 1155

Asp Ile  Val Arg Lys Glu Asp  Tyr Ile Tyr Leu Asp  Phe Phe Asn
    1160                 1165                 1170

Leu Asn  Gln Glu Trp Arg Val  Tyr Thr Tyr Lys Tyr  Phe Lys Lys
    1175                 1180                 1185

Glu Glu  Gln Lys Leu Phe Leu  Ala Pro Ile Tyr Asp  Ser Asp Glu
    1190                 1195                 1200

Phe Tyr  Asn Thr Ile Gln Ile  Lys Glu Tyr Asp Glu  Gln Pro Thr
    1205                 1210                 1215

Tyr Ser  Cys Gln Leu Leu Phe  Lys Lys Asp Glu Glu  Ser Thr Asp
    1220                 1225                 1230

Glu Ile  Gly Leu Ile Gly Ile  His Arg Phe Tyr Glu  Ser Gly Trp
    1235                 1240                 1245

Trp Phe  Glu Glu Tyr Lys Asp  Tyr Phe Cys Ile Ser  Lys Trp Tyr
    1250                 1255                 1260

Leu Lys  Glu Val Lys Arg Lys  Pro Tyr Asn Leu Lys  Leu Gly Cys
    1265                 1270                 1275

Asn Trp  Gln Phe Ile Pro Lys  Asp Glu Gly Trp Thr  Glu
    1280                 1285                 1290


<210> SEQ ID NO 53
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 53

Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140
```

```
Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Thr Tyr Lys Tyr Phe Lys Lys Glu Glu Met Lys Leu Phe Leu
                325                 330                 335

Ala Pro Ile Tyr Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Trp Trp Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430
```

<210> SEQ ID NO 54
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 54

```
Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80
```

```
Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Thr Tyr Lys Tyr Phe Lys Lys Glu Glu Met Lys Leu Phe Leu
                325                 330                 335

Ala Pro Ile Trp Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Trp Trp Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430


<210> SEQ ID NO 55
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 55

Ile Leu Asn Asn Ile Ile Leu Asn Leu Arg Tyr Lys Asp Asn Asn Leu
1               5                   10                  15
```

```
Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Gln Arg
305                 310                 315                 320

Val Tyr Thr Tyr Lys Tyr Phe Lys Lys Glu Glu Met Lys Leu Phe Leu
                325                 330                 335

Ala Pro Ile Ser Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Trp Trp Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430
```

```
<210> SEQ ID NO 56
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 56

Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Gln Arg
305                 310                 315                 320

Val Tyr Thr Tyr Lys Tyr Phe Lys Lys Glu Glu Val Lys Leu Phe Leu
                325                 330                 335

Ala Pro Ile Ser Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
```

```
    370                 375                 380

Tyr Glu Ser Gly Trp Trp Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430


<210> SEQ ID NO 57
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 57

Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
```

```
305                 310                 315                 320

Val Tyr Thr Tyr Lys Tyr Phe Lys Lys Glu Glu Val Lys Leu Phe Leu
                325                 330                 335

Ala Pro Ile Tyr Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Trp Trp Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430
```

<210> SEQ ID NO 58
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 58

```
Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
```

```
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Thr Tyr Lys Tyr Phe Lys Lys Glu Glu Val Lys Leu Phe Leu
                325                 330                 335

Ala Pro Ile Trp Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Trp Trp Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430


<210> SEQ ID NO 59
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 59

Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
            20                  25                  30

Glu Leu Asn Asp Lys Asn Gln Phe Lys Leu Thr Ser Ser Ala Asn Ser
        35                  40                  45

Lys Ile Arg Val Thr Gln Asn Gln Asn Ile Ile Phe Asn Ser Val Phe
    50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
            100                 105                 110

Ile Trp Thr Leu Ile Asp Ile Asn Gly Lys Thr Lys Ser Val Phe Phe
        115                 120                 125

Glu Tyr Asn Ile Arg Glu Asp Ile Ser Glu Tyr Ile Asn Arg Trp Phe
    130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
```

```
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285

Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Thr Tyr Lys Tyr Phe Lys Lys Glu Glu Gln Lys Leu Phe Leu
                325                 330                 335

Ala Pro Ile Tyr Asp Ser Asp Glu Phe Tyr Asn Thr Ile Gln Ile Lys
            340                 345                 350

Glu Tyr Asp Glu Gln Pro Thr Tyr Ser Cys Gln Leu Leu Phe Lys Lys
        355                 360                 365

Asp Glu Glu Ser Thr Asp Glu Ile Gly Leu Ile Gly Ile His Arg Phe
    370                 375                 380

Tyr Glu Ser Gly Trp Trp Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
            420                 425                 430


<210> SEQ ID NO 60
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 60

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
```

```
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540
```

```
Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960
```

```
Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                 1005

Ser Glu  Tyr Ile Asn Arg Trp  Phe Phe Val Thr Ile  Thr Asn Asn
    1010                 1015                 1020

Leu Asn  Asn Ala Lys Ile Tyr  Ile Asn Gly Lys Leu  Glu Ser Asn
    1025                 1030                 1035

Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Met Lys  Leu Phe Leu Ala Pro  Ile Tyr Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Trp Trp Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300
```

<210> SEQ ID NO 61
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 61

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
```

```
        420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845
```

```
Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095

Asp Phe  Trp Gly Asn Pro Leu  Met Tyr Asn Lys Glu  Tyr Tyr Met
    1100                1105                1110

Phe Asn  Ala Gly Asn Lys Asn  Ser Tyr Ile Lys Leu  Lys Lys Asp
    1115                1120                1125

Ser Pro  Val Gly Glu Ile Leu  Thr Arg Ser Lys Tyr  Asn Gln Asn
    1130                1135                1140

Ser Lys  Tyr Ile Asn Tyr Arg  Asp Leu Tyr Ile Gly  Glu Lys Phe
    1145                1150                1155

Ile Ile  Arg Arg Lys Ser Asn  Ser Gln Ser Ile Asn  Asp Asp Ile
    1160                1165                1170

Val Arg  Lys Glu Asp Tyr Ile  Tyr Leu Asp Phe Phe  Asn Leu Asn
    1175                1180                1185

Gln Glu  Trp Arg Val Tyr Thr  Tyr Lys Tyr Phe Lys  Lys Glu Glu
    1190                1195                1200

Met Lys  Leu Phe Leu Ala Pro  Ile Trp Asp Ser Asp  Glu Phe Tyr
    1205                1210                1215

Asn Thr  Ile Gln Ile Lys Glu  Tyr Asp Glu Gln Pro  Thr Tyr Ser
    1220                1225                1230

Cys Gln  Leu Leu Phe Lys Lys  Asp Glu Glu Ser Thr  Asp Glu Ile
    1235                1240                1245
```

```
Gly Leu  Ile Gly Ile His Arg  Phe Tyr Glu Ser Gly  Trp Trp Phe
    1250                1255                1260

Glu Glu  Tyr Lys Asp Tyr Phe  Cys Ile Ser Lys Trp  Tyr Leu Lys
    1265                1270                1275

Glu Val  Lys Arg Lys Pro Tyr  Asn Leu Lys Leu Gly  Cys Asn Trp
    1280                1285                1290

Gln Phe  Ile Pro Lys Asp Glu  Gly Trp Thr Glu
    1295                1300


<210> SEQ ID NO 62
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 62

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300
```

```
Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
```

```
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095

Asp Phe  Trp Gly Asn Pro Leu  Met Tyr Asn Lys Glu  Tyr Tyr Met
    1100                1105                1110

Phe Asn  Ala Gly Asn Lys Asn  Ser Tyr Ile Lys Leu  Lys Lys Asp
    1115                1120                1125

Ser Pro  Val Gly Glu Ile Leu  Thr Arg Ser Lys Tyr  Asn Gln Asn
    1130                1135                1140
```

```
Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Gln Arg Val Tyr Thr  Tyr Lys Tyr Phe Lys  Lys Glu Glu
    1190                 1195                 1200

Met Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Trp Trp Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300


<210> SEQ ID NO 63
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 63

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190
```

```
Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605
```

```
Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                 1005

Ser Glu  Tyr Ile Asn Arg Trp  Phe Phe Val Thr Ile  Thr Asn Asn
    1010                 1015                 1020

Leu Asn  Asn Ala Lys Ile Tyr  Ile Asn Gly Lys Leu  Glu Ser Asn
```

```
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095

Asp Phe  Trp Gly Asn Pro Leu  Met Tyr Asn Lys Glu  Tyr Tyr Met
    1100                1105                1110

Phe Asn  Ala Gly Asn Lys Asn  Ser Tyr Ile Lys Leu  Lys Lys Asp
    1115                1120                1125

Ser Pro  Val Gly Glu Ile Leu  Thr Arg Ser Lys Tyr  Asn Gln Asn
    1130                1135                1140

Ser Lys  Tyr Ile Asn Tyr Arg  Asp Leu Tyr Ile Gly  Glu Lys Phe
    1145                1150                1155

Ile Ile  Arg Arg Lys Ser Asn  Ser Gln Ser Ile Asn  Asp Asp Ile
    1160                1165                1170

Val Arg  Lys Glu Asp Tyr Ile  Tyr Leu Asp Phe Phe  Asn Leu Asn
    1175                1180                1185

Gln Glu  Trp Arg Val Tyr Thr  Tyr Lys Tyr Phe Lys  Lys Glu Glu
    1190                1195                1200

Val Lys  Leu Phe Leu Ala Pro  Ile Tyr Asp Ser Asp  Glu Phe Tyr
    1205                1210                1215

Asn Thr  Ile Gln Ile Lys Glu  Tyr Asp Glu Gln Pro  Thr Tyr Ser
    1220                1225                1230

Cys Gln  Leu Leu Phe Lys Lys  Asp Glu Glu Ser Thr  Asp Glu Ile
    1235                1240                1245

Gly Leu  Ile Gly Ile His Arg  Phe Tyr Glu Ser Gly  Trp Trp Phe
    1250                1255                1260

Glu Glu  Tyr Lys Asp Tyr Phe  Cys Ile Ser Lys Trp  Tyr Leu Lys
    1265                1270                1275

Glu Val  Lys Arg Lys Pro Tyr  Asn Leu Lys Leu Gly  Cys Asn Trp
    1280                1285                1290

Gln Phe  Ile Pro Lys Asp Glu  Gly Trp Thr Glu
    1295                1300


<210> SEQ ID NO 64
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 64

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
```

```
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495
```

```
Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910
```

```
Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                 1005

Ser Glu  Tyr Ile Asn Arg Trp  Phe Phe Val Thr Ile  Thr Asn Asn
    1010                 1015                 1020

Leu Asn  Asn Ala Lys Ile Tyr  Ile Asn Gly Lys Leu  Glu Ser Asn
    1025                 1030                 1035

Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Val Lys  Leu Phe Leu Ala Pro  Ile Trp Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Trp Trp Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300
```

<210> SEQ ID NO 65
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 65

Met Pro Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Glu Val Leu Asn Leu Thr
165 170 175

Arg Asn Gly Tyr Gly Ser Thr Gln Tyr Ile Arg Phe Ser Pro Asp Phe
180 185 190

Thr Phe Gly Phe Glu Glu Ser Leu Glu Val Asp Thr Asn Pro Leu Leu
195 200 205

Gly Ala Gly Lys Phe Ala Thr Asp Pro Ala Val Thr Leu Ala His Glu
210 215 220

Leu Ile His Ala Gly His Arg Leu Tyr Gly Ile Ala Ile Asn Pro Asn
225 230 235 240

Arg Val Phe Lys Val Asn Thr Asn Ala Tyr Tyr Glu Met Ser Gly Leu
245 250 255

Glu Val Ser Phe Glu Glu Leu Arg Thr Phe Gly Gly His Asp Ala Lys
260 265 270

Phe Ile Asp Ser Leu Gln Glu Asn Glu Phe Arg Leu Tyr Tyr Tyr Asn
275 280 285

Lys Phe Lys Asp Ile Ala Ser Thr Leu Asn Lys Ala Lys Ser Ile Val
290 295 300

Gly Thr Thr Ala Ser Leu Gln Tyr Met Lys Asn Val Phe Lys Glu Lys
305 310 315 320

Tyr Leu Leu Ser Glu Asp Thr Ser Gly Lys Phe Ser Val Asp Lys Leu
325 330 335

Lys Phe Asp Lys Leu Tyr Lys Met Leu Thr Glu Ile Tyr Thr Glu Asp
340 345 350

Asn Phe Val Lys Phe Phe Lys Val Leu Asn Arg Lys Thr Tyr Leu Asn
355 360 365

Phe Asp Lys Ala Val Phe Lys Ile Asn Ile Val Pro Lys Val Asn Tyr

```
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800
```

```
Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                 1005

Ser Glu  Tyr Ile Asn Arg Trp  Phe Phe Val Thr Ile  Thr Asn Asn
    1010                 1015                 1020

Leu Asn  Asn Ala Lys Ile Tyr  Ile Asn Gly Lys Leu  Glu Ser Asn
    1025                 1030                 1035

Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Gln Arg Val Tyr Thr  Tyr Lys Tyr Phe Lys  Lys Glu Glu
    1190                 1195                 1200
```

```
Val Lys  Leu Phe Leu Ala Pro  Ile Ser Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Trp Trp Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300


<210> SEQ ID NO 66
<211> LENGTH: 1304
<212> TYPE: PRT
<213> ORGANISM: Artificial Sequence
<220> FEATURE:
<223> OTHER INFORMATION: Synthetic Polypeptide

<400> SEQUENCE: 66

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255
```

```
Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
```

```
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095
```

```
Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Gln Lys  Leu Phe Leu Ala Pro  Ile Tyr Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Trp Trp Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300
```

ENGINEERED BOTULINUM NEUROTOXINS

RELATED APPLICATIONS

This application is a national stage filing under 35 U.S.C. § 371 of international application number PCT/US2017/036628, filed Jun. 8, 2017, which claims the benefit under 35 U.S.C. § 119(e) of U.S. provisional application No. 62/347,579, filed Jun. 8, 2016, each of which is incorporated by reference herein in its entirety.

BACKGROUND

In recent years, *Clostridial Botulinum* neurotoxin (BoNT) have been widely used to treat a growing list of medical conditions: local injections of minute amount of toxins can attenuate neuronal activity in targeted regions, which can be beneficial in many medical conditions as well as for cosmetic purposes[2-4]. To date, BoNT serotype A (BoNT/A) and BoNT serotype B (BoNT/B) are the only two BoNTs that are currently FDA-approved for use in humans[2-4]. As the application of BoNTs grows, limitations and adverse effects have been reported. The major limitation is the generation of neutralizing antibodies in patients, which renders future treatment ineffective. Termination of BoNT usage often leaves patients with no other effective ways to treat/relieve their disorders. Adverse effects associated with BoNT use range from transient non-serious events such as ptosis and diplopia to life-threatening events even death[6,7]. The limitations and adverse effects of BoNTs are largely correlated with dose. Modified BoNTs with improved specificity for neurons that maintain the same level of toxin activity with lower dose is highly desired.

SUMMARY

Some aspects of the present disclosure provide modified *Clostridial Botulinum* neurotoxin (BoNT) polypeptides comprising a modified receptor binding domain of *Clostridial Botulinum* serotype B (BoNT/B), comprising one or more substitution mutation(s) at positions corresponding to 1248 or 1249 in BoNT serotype B, strain 1 (BoNT/B1).

In some embodiments, the modified BoNT polypeptide comprises an amino acid sequence of any one of SEQ ID NOs: 1-8, having one or more substitution mutation(s) at positions 1248 or 1249 in any one of SEQ ID NOs: 1-7, or one or more substitution mutation(s) at positions 1249 or 1250 in SEQ ID NO: 8.

In some embodiments, the modified BoNT polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 1-8, having one or more substitution mutation(s) at positions 1248 or 1249 in any one of SEQ ID NOs: 1-7, or one or more substitution mutation(s) at positions 1249 or 1250 in SEQ ID NO: 8.

In some embodiments, the modified BoNT polypeptide consists of an amino acid sequence of any one of SEQ ID NOs: 1-8, having one or more substitution mutation(s) at positions 1248 or 1249 in any one of SEQ ID NOs: 1-7, or one or more substitution mutation(s) at positions 1249 or 1250 in SEQ ID NO: 8.

In some embodiments, the substitution mutation introduces any one of tryptophan (W), phenylalanine (F), tyrosine (Y), or histidine (H) at positions 1248 or 1249 in any one of SEQ ID NOs: 1-7, or at positions 1249 or 1250 in SEQ ID NO: 8. In some embodiments, the substitution mutation introduces a tryptophan (W) in both positions 1248 and 1249 in any one of SEQ ID NOs: 1-7, or positions 1249 and 1250 in SEQ ID NO: 8. In some embodiments, the modified BoNT polypeptide comprises the amino acid sequence of SEQ ID NO: 33.

In some embodiments, the modified BoNT polypeptide comprises an amino acid sequence of any one of SEQ ID NOs: 9-16, having one or more substitution mutation(s) at positions 389 or 390 in any one of SEQ ID NOs: 9-15, or one or more substitution mutation(s) at positions 390 or 391 in SEQ ID NO: 16.

In some embodiments, the modified BoNT polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 9-16, having one or more substitution mutation(s) at positions 389 or 390 in any one of SEQ ID NOs: 9-15, or one or more substitution mutation(s) at positions 390 or 391 in SEQ ID NO: 16.

In some embodiments, the modified BoNT polypeptide consists of an amino acid sequence of any one of SEQ ID NOs: 9-16, having one or more substitution mutation(s) at positions 389 or 390 in any one of SEQ ID NOs: 9-15, or one or more substitution mutation(s) at positions 390 or 391 in SEQ ID NO: 16.

In some embodiments, the substitution mutation introduces any one of tryptophan (W), phenylalanine (F), tyrosine (Y), or histidine (H) at positions 389 or 390 in any one of SEQ ID NOs: 9-15, or at positions 390 or 391 in SEQ ID NO: 16. In some embodiments, the substitution mutation introduces a tryptophan (W) in both positions 389 and 390 in any one of SEQ ID NOs: 9-15, or positions 390 and 391 in SEQ ID NO: 16. In some embodiments, the modified BoNT polypeptide comprises the amino acid sequence of SEQ ID NO: 34.

In some embodiments, the modified BoNT polypeptide comprises an amino acid sequence of any one of SEQ ID NOs: 17-24, having one or more substitution mutation(s) at positions 1261 or 1262 in any one of SEQ ID NOs: 17-24.

In some embodiments, the modified BoNT polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 17-24, having one or more substitution mutation(s) at positions 1261 or 1262 in any one of SEQ ID NOs: 17-24.

In some embodiments, the modified BoNT polypeptide consists of the amino acid sequence of any one of SEQ ID NOs: 17-24, having one or more substitution mutation(s) at positions 1261 or 1262 in any one of SEQ ID NOs: 17-24.

In some embodiments, the substitution mutation introduces any one of tryptophan (W), phenylalanine (F), tyrosine (Y), or histidine (H) at positions 1261 or 1262 in any one of SEQ ID NOs: 17-24. In some embodiments, the substitution mutation introduces a tryptophan (W) in both positions 1261 and 1262 in any one of SEQ ID NOs: 17-24. In some embodiments, the modified BoNT polypeptide comprises the amino acid sequence of SEQ ID NO: 35 or SEQ ID NO: 36.

Some aspects of the present disclosure provide modified BoNT polypeptides, comprising the amino acid sequence of a polypeptide corresponding to a fragment between amino acid 1245 and amino acid 1252 of serotype B, strain 1 (BoNT/B1), having one or more substitution mutation(s) at positions corresponding to 1248 or 1249 in BoNT/B1.

In some embodiments, the modified BoNT polypeptide comprises the amino acid sequence of any one of SEQ ID NOs: 25-32, having one or more substitution mutation(s) at positions 4 or 5 in any one of SEQ ID NOs: 25-32.

In some embodiments, the modified BoNT comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 25-32, having one or more substitution mutation(s) at positions 4 or 5 in any one of SEQ ID NOs: 25-32. In some embodiments, the modified BoNT polypeptide consists of the amino acid sequence of any one of SEQ ID NOs: 25-32, having one or more substitution mutations at positions 4 or 5 in any one of SEQ ID NOs: 25-32.

In some embodiments, the substitution mutation introduces any one of tryptophan (W), phenylalanine (F), tyrosine (Y), or histidine (H) at positions 4 or 5 in any one of SEQ ID NOs: 25-32. In some embodiments, the substitution mutation introduces a tryptophan (W) in both positions 4 and 5 in any one of SEQ ID NOs: 25-32. In some embodiments, the modified BoNT polypeptide comprises the amino acid sequence of SEQ ID NOs: 37.

In some embodiments, the substitution mutation creates a loop in the receptor binding domain that penetrates a lipid membrane. In some embodiments, the modified BoNT polypeptides disclosed herein have enhanced binding to a nerve terminal, compared to a corresponding wild type BoNT polypeptide, and wherein the enhanced binding is mediated by the penetration of the loop into the lipid membrane.

In some embodiments, the enhanced binding is specific to a presynaptic nerve terminal. In some embodiments, the presynaptic nerve terminal is a mouse presynaptic nerve terminal. In some embodiments, the presynaptic nerve terminal is a human presynaptic nerve terminal.

In some embodiments, the modified BoNT polypeptide further comprises one or more substitution mutation(s) at positions corresponding to 1178, 1191, or 1199 in BoNT/B1. In some embodiments, the substitution mutation(s) correspond to E1191M/S1199Y, E1191M/S1199W, E1191M/W1178Q, E1191V/S1199Y, 1191V/S1199W, E1199V/W1178Q, or E1199Q/S1199Y in BoNT/B1. In some embodiments, the modified BoNT polypeptide comprises the amino acid sequence of any one of SEQ ID NOs: 46-66.

In some embodiments, the modified BoNT polypeptide has enhanced binding affinity to SytII.

Further provided herein are nucleic acid molecules comprising a polynucleotide encoding a modified BoNT polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identity the modified BoNT polypeptide disclosed herein. Nucleic acid vectors comprising the such nucleic acid molecules are also described.

Further provided herein are cells containing the nucleic acid molecules or the nucleic acid vector described herein. Cells expressing the modified BoNT polypeptide of the present disclosure are also described.

Other aspects of the present disclosure provide methods of producing the modified BoNT polypeptides disclosed herein, comprising the steps of culturing the cell expressing such modified BoNT polypeptides under conditions wherein said modified BoNT polypeptide is produced. In some embodiments, the method further comprises recovering the modified BoNT polypeptide from the culture.

Other aspects of the present disclosure provide modified *Clostridial Botulinum* neurotoxin (BoNT) polypeptides comprising: a) a protease domain; b) a protease cleavage site; c) a translocation domain; and d) a modified receptor binding domain of *Clostridial Botulinum* serotype B, comprising one or more substitution mutation(s) at positions corresponding to 1248 or 1249 in BoNT serotype B, strain 1 (BoNT/B1).

In some embodiments, the polypeptide comprises a modified receptor binding domain of any one of BoNT/B1, BoNT/B2, BoNT/B3, BoNT/B4, BoNT/B5, BoNT/B6, BoNT/B7, and BoNT/B8.

In some embodiments, the modified receptor binding domain comprises one substitution mutation. In some embodiments, the one substitution mutation corresponds to I1248F, I1248Y, I1248H, I1248W, V1249W, V1249F, V1249Y, or V1249H in BoNT/B1.

In some embodiments, the modified receptor binding domain comprises two substitution mutations. In some embodiments, the substitution mutation corresponds to I1248W/V1249F, I1248W/V1249Y, I1248W/V1249H, I1248F/V1249Y, I1248F/V1249H, I1248Y/V1249H, I1248F/V1249W, I1248Y/V1249W, I1248H/V1249W, I1248Y/V1249F, I1248H/V1249F, or I1248H/V1249Y in BoNT/B1.

In some embodiments, the protease domain, translocation domain, and protease cleavage site are from serotype selected from the group consisting of A, B, C, D, E, F, G, and combinations thereof.

In some embodiments, the protease domain, translocation domain, and protease cleavage site are from serotype B, strain 1. In some embodiments, the protease domain, translocation domain, and protease cleavage site are from serotype A, strain 1.

In some embodiments, the modified BoNT polypeptide penetrates a lipid membrane. In some embodiments, the modified BoNT polypeptide has enhanced binding to a nerve terminal, compared to a corresponding wild-type BoNT, and wherein the enhanced binding is mediated by the penetration of the loop of the lipid membrane. In some embodiments, the enhanced binding is specific to a presynaptic nerve terminal. In some embodiments, the presynaptic nerve terminal is a mouse presynaptic nerve terminal. In some embodiments, the presynaptic nerve terminal is a human presynaptic nerve terminal.

In some embodiments, the modified BoNT polypeptide disclosed herein, further comprises one or more substitution mutation(s) at positions corresponding to 1178, 1191, or 1199 in BoNT/B1. In some embodiments, the substitution mutation(s) correspond to E1191M/S1199Y, E1191M/S1199W, E1191M/W1178Q, E1191V/S1199Y, 1191V/S1199W, E1199V/W1178Q, or E1199Q/S1199Y in BoNT/B1. In some embodiments, the modified BoNT polypeptide comprises the amino acid sequence of any one of SEQ ID NOs: 46-66. In some embodiments, the modified BoNT polypeptide has enhanced binding affinity to SytII.

Further provided herein are isolated nucleic acid molecules comprising a polynucleotide encoding a modified BoNT polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identity the modified BoNT polypeptide of the present disclosure. Also provided herein are nucleic acid vectors comprising such nucleic acid molecules and cells containing them. Cells expressing the modified BoNT polypeptides are also contemplated.

Further provided herein are methods of producing a modified botulinum neurotoxin (BoNT) polypeptide, comprising the steps of culturing the cells described herein under conditions wherein said BoNT polypeptide is produced. In some embodiments, the method further comprises recovering the BoNT polypeptide from the culture.

Other aspects of the present disclosure provide chimeric molecules comprising a first portion linked to a second portion, wherein the first portion is a modified BoNT polypeptide of the present disclosure.

In some embodiments, the first portion and the second portion are linked covalently. In some embodiments, the first portion and the second portion are linked non-covalently.

In some embodiments, the second portion is selected from the group consisting of a small molecule, a nucleic acid, a short polypeptide and a protein. In some embodiments, the second portion is a bioactive molecule. In some embodiments, the second portion is a non-polypeptide drug. In some embodiments, the second portion is a therapeutic polypeptide.

Nucleic acids, nucleic acid vectors encoding such chimeric molecules, cells containing the nucleic acids, and cells that express such chimeric molecules are also described.

Other aspects of the present disclosure provide pharmaceutical compositions comprising the modified BoNT polypeptide or the chimeric molecule described herein. In some embodiments, the pharmaceutical composition further comprises a pharmaceutically acceptable excipient.

Kits comprising a pharmaceutical composition and directions for therapeutic administration of the pharmaceutical composition are also described.

Other aspects of the present disclosure provide methods of treating a condition of unwanted neuronal activity, the method comprising administering a therapeutically effective amount of the modified BoNT polypeptide, the chimeric molecule, or the pharmaceutical composition disclosed herein to a subject to treat the condition.

In some embodiments, condition is associated with overactive neurons or glands. In some embodiments, the condition is selected from the group consisting of, spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions, secretory disorders, pain from muscle spasms, headache pain, sports injuries, and dermatological or aesthetic/cosmetic conditions.

In some embodiments, the administering is via injection, wherein the injection is where unwanted neuronal activity is present. In some embodiments, uptake of the modified BoNT polypeptide by the neuron(s) at the site of injection is enhanced, and wherein the diffusion of the polypeptide to other regions is reduced.

In some embodiments, uptake of the modified BoNT polypeptide by the neuron(s) at the injection is enhanced, and wherein the polypeptide has reduced immunogenicity.

In some embodiments, the modified BoNT polypeptide, the chimeric molecule, and the pharmaceutical composition of the present disclosure, may be used for treating a condition associated with unwanted neuronal activity.

In some embodiments, the modified BoNT polypeptide, the chimeric molecule, and the pharmaceutical composition of the present disclosure, may be used in medicine.

Yet another aspect of the present disclosure provide methods of making a modified *Clostridial Botulinum* neurotoxin (BoNT), the method comprising making one or more substitution mutation(s) at a position corresponding to 1248 or 1249 in serotype B, strain 1 (BoNT/B1).

In some embodiments, the substitution mutation corresponds to I1248F, I1248Y, I1248H, I1248W, V1249W, V1249F, V1249Y, V1249H, I1248W/V1249F, I1248W/V1249Y, I1248W/V1249H, I1248F/V1249Y, I1248F/V1249H, I1248Y/V1249H, I1248F/V1249W, I1248Y/V1249W, I1248H/V1249W, I1248Y/V1249F, I1248H/V1249F, or I1248H/V1249Y.

In some embodiments, the BoNT polypeptide is BoNT serotype B (BoNT/B). In some embodiments, the BoNT polypeptide is any one of BoNT/B, strains 1-8. In some embodiments, the modified BoNT polypeptide penetrates a lipid membrane. In some embodiments, the modified BoNT polypeptide has enhanced binding to neurons, wherein the enhanced binding is mediated by penetrating the lipid membrane. In some embodiments, the enhanced binding is specific to a presynaptic nerve terminal. In some embodiments, the presynaptic nerve terminal is a mouse presynaptic nerve terminal. In some embodiments, the presynaptic nerve terminal is a human presynaptic nerve terminal.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

Figures 1C, 1D:
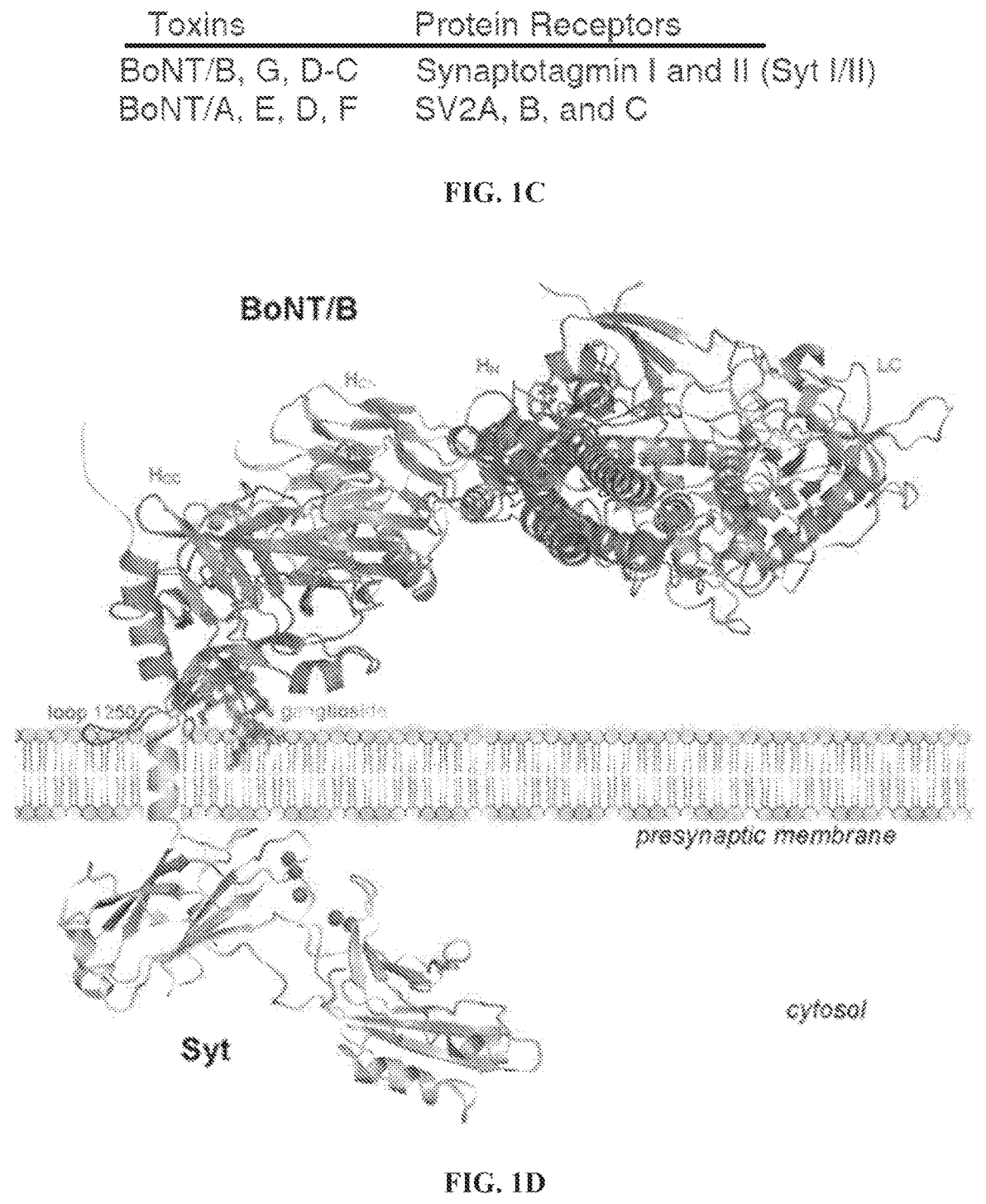

FIGS. 1A-1D show schematic models for how BoNTs target neurons (FIG. 1A), their overall protein structure (FIG. 1B), a list of identified receptors (FIG. 1C), and the structural model for BoNT/B binding to its receptors Syt and gangliosides (FIG. 1D). FIG. 1A shows a schematic view of BoNT actions: BoNTs recognize neurons by binding to their specific receptors (step 1), enter neurons via receptor-mediated endocytosis (step 2), the light chains of BoNTs then translocate across endosomal membranes into the cytosol (step 3), where these light chains act as proteases to cleave target host proteins (step 4). FIG. 1A is adapted from Arnon, S. et al, *JAMA,* 285:1059, 2001[35]. FIG. 1B shows BoNTs composed of a light chain and a heavy chain, connected via a disulfide bond. The heavy chain can be further divided into two domains: the translocation domain ($H_N$) and the receptor binding domain ($H_C$). These functional domains are switchable between different BoNTs. For instance, BoNT/B-$H_C$ can be used to replace BoNT/A-$H_C$ to generate chimeric toxins. FIG. 1C provides a list of identified toxins receptors. FIG. 1D is a structural model showing binding of BoNT/B to its protein receptor, Syt (I/II), as well as its lipid co-receptor, gangliosides, on the cell surface. The extended loop that is analogous to the loop in BoNT/DC is labeled as "loop 1250". The extended loop is marked as "loop 1250". FIG. 1D is adapted from Chai et al, *Nature,* 444:1096, 2006.

FIGS. 2A-2B show the extended loop in BoNT/DC that penetrating into lipid membranes and the analogous loop in BoNT/B. FIG. 2A shows overlaid crystal structures of BoNT/DC-$H_C$ and BoNT/B-$H_C$, with their extended loop in BoNT/DC-$H_C$ and in BoNT/B-$H_C$ marked with arrows. FIG. 2B shows the crystal structure of BoNT/B-$H_C$ modeled on plasma membranes (PM), showing that the extended loop is located at an ideal position to interact with PM.

FIG. 3A is a schematic drawing of liposome flotation assay. FIG. 3B shows the results of experiments carried out as depicted in FIG. 3A. Briefly, liposomes containing PC alone or PC plus a brain ganglioside mixture (gang mix, 1%) were incubated with indicated BoNT/B-$H_C$. Samples were centrifuged for 1 hour at 240,000 g in a sucrose gradient. Liposome fractions that floated to the top of the gradient were collected and subjected to immunoblotting analysis detecting HA tagged BoNT/B-$H_C$. Samples without liposomes served as a negative control. WT BoNT/B-$H_C$ did not bind to PC liposomes, with or without gangliosides. In contrast, BoNT/B-$H_C$ (I1248W) and BoNT/B-$H_C$ (I1248W/V1249W) showed strong binding to PC liposomes and further enhanced binding to ganglioside-containing liposomes.

FIG. 4A shows the results of cultured rat cortical neurons exposed to indicated BoNT/B-$H_C$ (100 nM, 5 min in High $K^+$ buffer). Cells were washed and harvested. Cell lysates were subjected to immunoblotting analysis. Actin served as an internal loading control. FIG. 4B shows the binding of BoNT/B-$H_C$ to neurons as described in FIG. 4A quantified and normalized to actin levels. BoNT/B-$H_C$ (I1248W) showed 2.7-fold increase and BoNT/B-$H_C$ (I1248W/V1249W) showed 3.5-fold increase over WT BoNT/B-$H_C$.

FIG. 5 shows that I1248W and V1249W mutations in BoNT/B-$H_C$ enhanced specific binding to presynaptic nerve terminals. Cultured rat cortical neurons were exposed to indicated BoNT/B-$H_C$ (100 nM, 5 min in High $K^+$ buffer). Cells were washed, fixed and subjected to immunostaining analysis. Synapsin was labeled as a marker for presynaptic terminals. BoNT/B-$H_C$ (I1248W) and BoNT/B-$H_C$ (I1248W/V1249W) showed greatly increased binding to neurons than WT BoNT/B-$H_C$. The area marked by white squares are enlarged at the lower panels to show that binding of BoNT/B-$H_C$ (I1248W) and BoNT/B-$H_C$ (I1248W/V1249W) are co-localized with synapsin, thus demonstrating that these mutants maintained the specificity toward presynaptic terminals.

DETAILED DESCRIPTION OF CERTAIN EMBODIMENTS

Figure 1A:
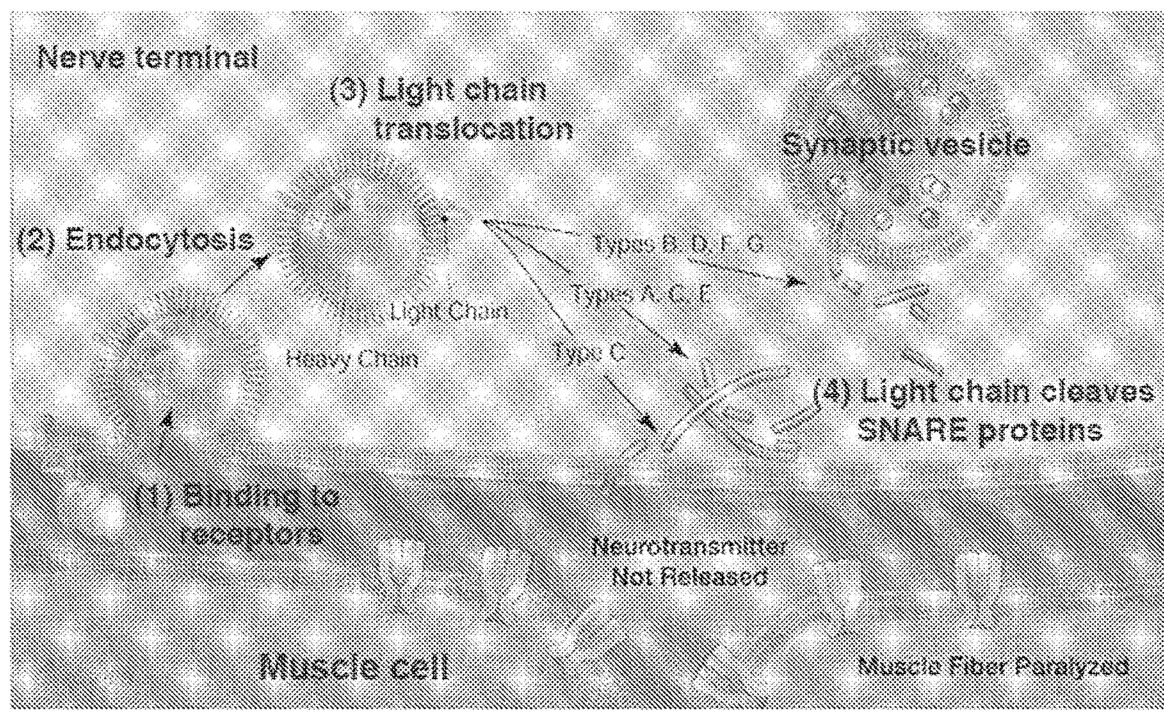
Figure 1B:
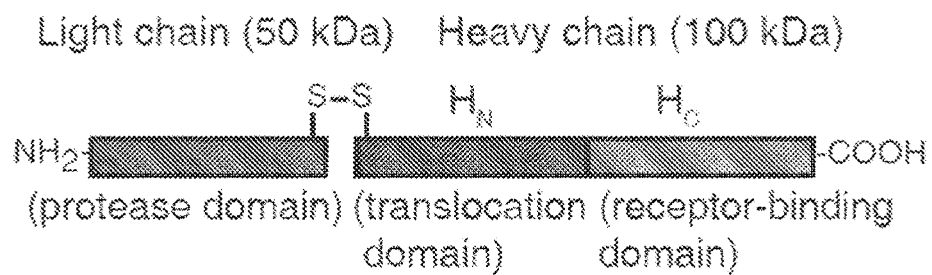

Botulinum neurotoxins are a family of bacterial toxins, including seven major serotypes (BoNT/A-G)[1]. These toxins act by blocking neurotransmitter release from neurons, thus paralyzing animals and humans. In recent years, BoNTs have been widely used to treat a growing list of medical conditions: local injections of minute amount of toxins can attenuate neuronal activity in targeted regions, which can be beneficial in many medical conditions as well as for cosmetic purposes[2-4].

BoNT/A and BoNT/B are the only two BoNTs that are currently FDA-approved for use in humans[2-4]. These are toxins purified from bacteria without any sequence modifications (defined as wild type, WT). As the application of BoNTs grows, limitations and adverse effects have been reported. The major limitation is the generation of neutralizing antibodies in patients, which renders future treatment ineffective[5]. Termination of BoNT usage often leaves patients with no other effective ways to treat/relieve their disorders. The possibility of antibody responses is directly related to both toxin doses and the frequency of injection[5]. Therefore, this limitation mainly occurs in treating muscle spasms, which involves high dose of toxins. Consistently, antibody responses have not been observed in cosmetic applications, which use extremely low toxin doses.

The major adverse effects are also often associated with treating muscle spasms, but not cosmetic applications. This is because the adverse effects are largely due to diffusion of toxins to other regions of the body and the possibility of toxin diffusion is directly related to injected doses. The adverse effects ranges from transient non-serious events such as ptosis and diplopia to life-threatening events even death[6,7]. In a petition letter filed in 2008 by Dr. Sidney Wolfe to FDA, a total of 180 serious adverse events, including 16 deaths have been documented. As a result, FDA now requires the "Black box warning" on all BoNT products, highlighting the risk of the spread of toxins, following similar warnings issued by the European Union.

Because both the generation of neutralizing antibodies and toxin diffusion are directly related to injected doses, lowering toxin doses (while maintaining the same levels of toxin activity) is highly desired, which means the efficacy of individual toxin molecules has to be enhanced. Such modified BoNTs with improved specificity for neurons will also reduce any potential off-target effects due to non-specific entry into other cell types.

Enhancing the ability of BoNTs to recognize their neuronal receptors will facilitate absorbance of toxins into neurons at the injection site, therefore shielding toxins from triggering immune responses and also preventing their diffusion. Enhanced affinity and specificity to neuronal receptors will also reduce potential off-target effects due to non-specific entry into other cell types.

By utilizing both protein and ganglioside receptors, BoNTs gain the ability to target neurons with extremely high efficacy and specificity. BoNT/B is less specific and potent in humans due to its greatly diminished binding affinity toward human Syt II (h-Syt II). Humans remain sensitive to BoNT/B, as BoNT/B still binds human Syt I (h-Syt I). It has been a long-standing clinical observation that BoNT/B has to be used at ~60-100 fold higher doses than BoNT/A in order to achieve the same level of effects in patients. Higher BoNT/B doses correspond to increased chances for triggering antibody responses and for serious side-effects to occur.

Accordingly, restoring high-affinity binding of BoNT/B to its target cells (e.g., neurons) may increase its efficacy and specificity, reduce the dose in therapeutic applications, and lower the occurrence of detrimental adverse effects for this major therapeutic toxin. A series of mutations in BoNT/B receptor binding domain in positions 1178, 1191 or S1199

(e.g., E1191M/S1199Y, E1191M/S1199W, E1191M/W1178Q, E1191V/S1199Y, 1191V/S1199W, E1199V/W1178Q, or E1199Q/S1199Y) that significantly enhanced binding of BoNT/B to human Syt II were recently discovered (WO 2013180799, the entire contents of which is hereby incorporated by reference).

Figures 2A, 2B:
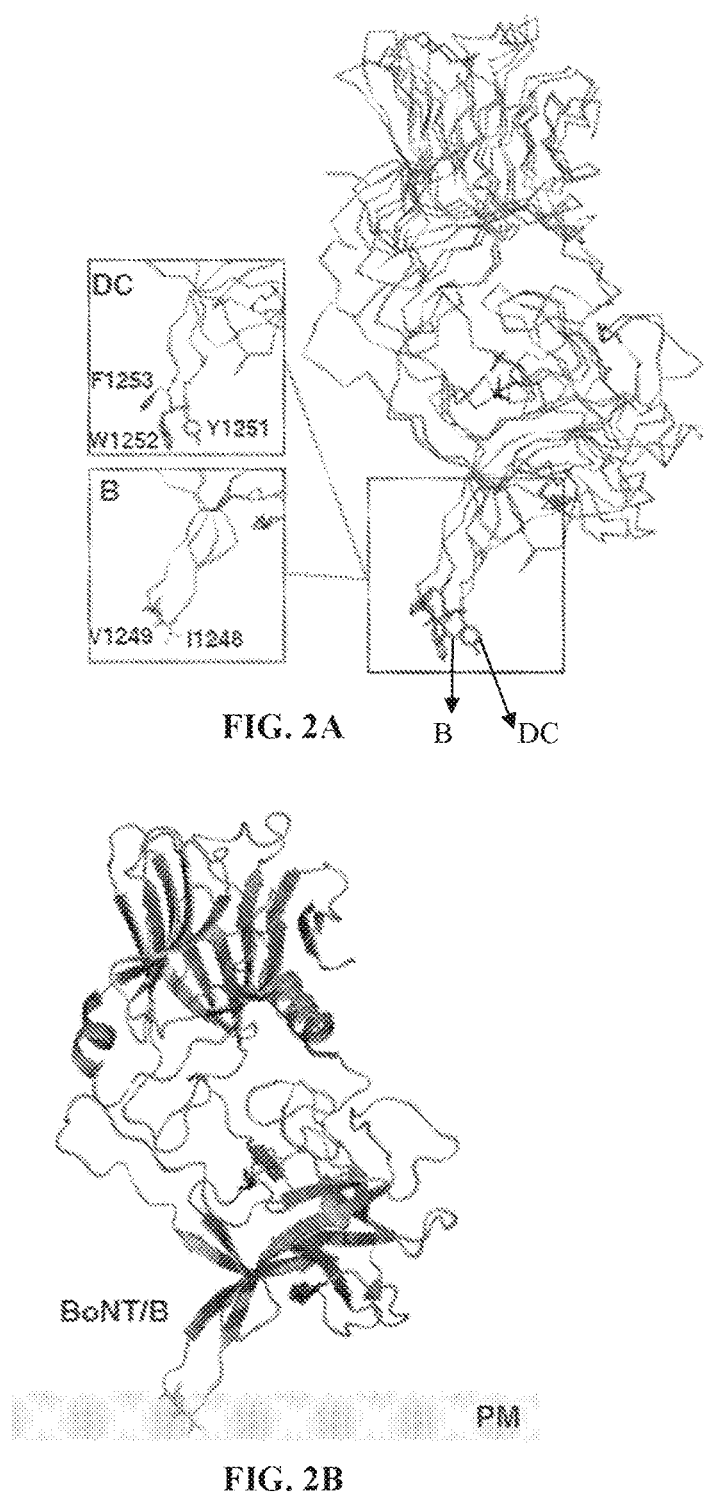

Described herein are novel BoNT/B mutations that further enhance the binding of BoNT/B to its target cells via a previously unexplored mechanism. The identification of these novel mutations are based, at least in part, on the observation that one botulinum neurotoxin, BoNT/DC, showed the highest potency in mice ($1.1\times10^{9}$ $LD_{50}$/mg, which is roughly 5-30 fold more than any other BoNTs). Similar to other BoNTs, BoNT/DC shares Syt I/II as its receptor and requires gangliosides as co-receptor. Thus, its superior potency may stem from other unidentified source. As shown in FIG. 2A, the crystal structure of BoNT/DC revealed an extended loop in the receptor binding domain (FIG. 2A)[32]. This loop contains many hydrophobic residues and is widely accepted in the art as ganglioside binding loop (GBL), as mutations within this loop abolishes binding of BoNT/DC-$H_C$ to immobilized gangliosides[33,34].

Provided herein, are novel and unexpected findings that this loop is not directly involved in ganglioside binding. Instead, this loop indirectly contributes to ganglioside binding via non-specific penetration into hydrophobic lipid membranes. Indeed, a point mutation at a tip residue, F1253A, was found to abolish BoNT/DC-$H_C$ binding to ganglioside-free liposomes, suggesting that the tip of this loop penetrates into lipid membranes. This action provides an additional anchor to neuronal membranes, which greatly facilitates binding of BoNT/DC to gangliosides and Syt I/II in a synergistic manner, therefore enhancing the overall binding of BoNT/DC to neurons.

Interestingly, the crystal structure of BoNT/B revealed that it has an extended loop similar to the one found in BoNT/DC (FIG. 2B) 15. It is also located in an ideal position for penetrating into membranes when BoNT/B binds to gangliosides and Syt I/II, even though the wild-type BoNT/B does not have the ability to penetrate into membranes. The major difference between the loop in BoNT/B and the loop in BoNT/DC is that their exposed residues at the tip of the loop are different: BoNT/B contains I1248/V1249, while BoNT/DC contains W1252/F1253. Both W and F are typical hydrophobic residues with strong tendency of penetrating into lipid membranes, while I and V are less likely to interact with membranes. Replacing I1248/V1249 with W or F residues may create a loop in BoNT/B that can penetrate into membranes, just like the one in BoNT/DC.

Accordingly, some aspects of the present disclosure provide modified *Clostridial Botulinum* neurotoxins (BoNT) comprising a modified receptor binding domain of *Clostridial Botulinum* serotype B.

As used herein, the term "*Clostridial Botulinum* neurotoxin (BoNT)" encompasses any polypeptide or fragment from a Botulinum neurotoxin. In some embodiments, the term BoNT refers to a full-length BoNT. In some embodiments, the term BoNT refers to a fragment of the BoNT that can execute the overall cellular mechanism whereby a BoNT enters a neuron and inhibits neurotransmitter release. In some embodiments, the term BoNT simply refers to a fragment of the BoNT, without requiring the fragment to have any specific function or activity. Other terms that may be used throughout the present disclosure for "*Clostridial Botulinum* neurotoxins" may be BoNTs, Botulinum toxins, or *C. Botulium* toxins. It is to be understood that these terms are used interchangeably.

A "modified *Clostridial Botulinum* neurotoxin (BoNT)" encompasses a BoNT comprising any modifications in the amino acid sequence, e.g., truncation, addition, amino acid substitution, and any combination thereof. For example, a BoNT comprising amino acid substitution mutation in I1248 or V1249 is a modified BoNT. In another example, a fragment or a domain of the full-length BoNT (e.g., the receptor binding domain) is considered a modified BoNT. In some embodiments, a domain of the BoNT may also comprise amino acid substitution mutation(s), e.g., a receptor binding domain comprising substitution mutation at positions corresponding to 1248 or 1249 of the full-length BoNT.

The term "enters a cell" when used to describe the action of a BoNT of the present disclosure, encompasses the binding of a BoNT to a low or high affinity receptor complex, binding of a BoNT to ganglioside, penetration of a BoNT into the lipid membrane, the internalization of the toxin, the translocation of the toxin light chain into the cytoplasm and the enzymatic modification of a BoNT substrate.

As used herein, the term "*Clostridial Botulinum* neurotoxin (BoNT) protease domain" means a BoNT domain that can execute the enzymatic target modification step of the intoxication process. Thus, a BoNT protease domain specifically targets a *C. Botulinum* toxin substrate and encompasses the proteolytic cleavage of a *C. Botulinum* toxin substrate, such as, e.g., SNARE proteins like a SNAP-25 substrate, a VAMP substrate and a Syntaxin substrate.

As used herein, the term "*Clostridial Botulinum* neurotoxin (BoNT) translocation domain" or "$H_n$" means a BoNT domain that can execute the translocation step of the intoxication process that mediates BoNT light chain translocation. Thus, an $H_n$ facilitates the movement of a BoNT light chain across a membrane into the cytoplasm of a cell. Non-limiting examples of a H include a BoNT/A H, a BoNT/B HN, a BoNT/C1 HN, a BoNT/D HN, a BoNT/E HN, a BoNT/F HN, and a BoNT/G HN.

As used herein, the term "*Clostridial Botulinum* neurotoxin (BoNT) receptor-binding domain" is synonymous with "He domain" and means any naturally occurring BoNT receptor binding domain that can execute the cell binding step of the intoxication process, including, e.g., the binding of the BoNT to a BoNT-specific receptor system located on the plasma membrane surface of a target cell. Some aspects of present disclosure relate to modified BoNT receptor binding domains from serotype B (BoNT/B), that enhances the binding of the BoNT/B to a cell, e.g., neurons. BoNT/B has eight subtypes, BoNT/B1, BoNT/B2, BoNT/B3, BoNT/B4, BoNT/B5, BoNT/B6, BoNT/B7, and BoNT/B8. Thus, the present disclosure encompasses modified BoNT/B receptor binding domain from all and any of the eight subtypes. It is appreciated that when "BoNT/B" is referred to, it encompasses all the subtypes of BoNT/B. In some embodiments, a "modified BoNT/B receptor binding domain" comprises novel amino acid substitution mutations described in the present disclosure. Such amino acid substitution mutations form a "membrane penetration loop" in the modified receptor binding domain. Such "membrane penetration loop" penetrates into the lipid membrane of a neuron when the neuron contacts the modified receptor binding domain of the BoNT/B, enhances the binding of the BoNT to the neuron, and facilitates the intake of the BoNT/B by the neuron. Such a molecule is typically generated through genetic recombination technology.

The term "binding activity" means that one molecule is directly or indirectly contacting another molecule via at least one intermolecular or intramolecular force, including, without limitation, a covalent bond, an ionic bond, a metallic bond, a hydrogen bond, a hydrophobic interaction, a van der Waals interaction, and the like, or any combination thereof. "Bound" and "bind" are considered terms for binding.

As used herein, the term "*Clostridial Botulinum* neurotoxin (BoNT) target cell" means a cell that is a naturally occurring cell that a naturally occurring BoNT is capable of intoxicating, including, without limitation, motor neurons; sensory neurons; autonomic neurons; such as, e.g., sympathetic neurons and parasympathetic neurons; non-peptidergic neurons, such as, e.g., cholinergic neurons, adrenergic neurons, noradrenergic neurons, serotonergic neurons, GABAergic neurons; and peptidergic neurons, such as, e.g., Substance P neurons, Calcitonin Gene Related Peptide neurons, vasoactive intestinal peptide neurons, Neuropeptide Y neurons, cholecystokinin neurons.

As used herein, the term "binding affinity" means how strong a molecule's binding activity is for a particular receptor system. In general, high binding affinity results from greater intermolecular force between a binding domain and its receptor system while low binding affinity involves less intermolecular force between the ligand and its receptor. High binding affinity involves a longer residence time for the binding domain at its receptor binding site than is the case for low binding affinity. As such, a molecule with a high binding affinity means a lower concentration of that molecule is required to maximally occupy the binding sites of a receptor system and trigger a physiological response. Conversely, low binding affinity means a relatively high concentration of a molecule is required before the receptor binding sites of a receptor system is maximally occupied and the maximum physiological response is achieved. Thus, a botulinum neurotoxin of the present disclosure with increased binding activity due to high binding affinity will allow administration of reduced doses of the toxin, thereby reducing or preventing unwanted side-effects associated with toxin dispersal into non-targeted areas.

As the term is used herein, "enhanced binding" when used to describe the binding affinity of a modified BoNT molecule of the present disclosure to a cell (e.g., a neuron), refers to an increase in the binding affinity for a cell (e.g., increased by 10%, 20%, 30%, 40%, 50%, 60%, 70%, 80%, 90%, or more of the binding affinity of the wild type molecule) as compared to the non-substituted version of the molecule. In one embodiment, the enhanced binding is an order of magnitude or more higher than the Kd of the non-substituted neurotoxin (e.g., the neurotoxin with a naturally occurring receptor binding domain). In one embodiment, the enhanced binding is significantly higher (e.g., 1.5×, 2.0×, 2.5×, 3.0×, or more) than the Kd of the non-substituted fragment.

By "isolated" is meant a material that is free to varying degrees from components which normally accompany it as found in its native state. "Isolate" denotes a degree of separation from original source or surroundings, e.g. from flanking DNA or from the natural source of the DNA. The term "purified" is used to refer to a substance such as a polypeptide that is "substantially pure", with respect to other components of a preparation (e.g., other polypeptides). It can refer to a polypeptide that is at least about 50%, 60%, 70%, or 75%, preferably at least about 85%, more preferably at least about 90%, and most preferably at least about 95% pure, with respect to other components. The terms "substantially pure" or "essentially purified", with regard to a polypeptide, refers to a preparation that contains fewer than about 20%, more preferably fewer than about 15%, 10%, 8%, 7%, most preferably fewer than about 5%, 4%, 3%, 2%, 1%, or less than 1%, of one or more other components (e.g., other polypeptides or cellular components).

The term "substitution mutation" without the reference to a specific amino acid, may include any amino acid other than the wild type residue normally found at that position. Such substitutions may be replacement with non-polar (hydrophobic) amino acids, such as glycine, alanine, valine, leucine, isoleucine, methionine, phenylalanine, tryptophan, and proline.

Substitutions may be replacement with polar (hydrophylic) amino acids such as serine, threonine, cysteine, tyrosine, asparagine, and glutamine. Substitutions may be replacement with electrically charged amino acids, e.g., negatively electrically charged amino acids such as aspartic acid and glutamic acid and positively electrically charged amino acids such as lysine, arginine, and histidine.

The substitution mutations described herein will typically be replacement with a different naturally occurring amino acid residue, but in some cases non-naturally occurring amino acid residues may also be substituted. Non-natural amino acids, as the term is used herein, are non-proteinogenic (i.e., non-protein coding) amino acids that either occur naturally or are chemically synthesized. Examples include but are not limited to β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. In some embodiments, the amino acid can be substituted or unsubstituted. The substituted amino acid or substituent can be a halogenated aromatic or aliphatic amino acid, a halogenated aliphatic or aromatic modification on the hydrophobic side chain, or an aliphatic or aromatic modification.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

The modified BoNTs of the present disclosure, comprise one or more amino acid substitution mutation(s) at positions corresponding to 1248 or 1249 in BoNT serotype B, strain 1 (BoNT/B1, SEQ ID NO: 1). BoNT/B has 8 subtypes (BoNT/B1-B8). Thus, provided herein are modified BoNT polypeptide comprising a modified receptor binding domain from any one of BoNT/B1 (SEQ ID NO: 1), BoNT/B2 (SEQ ID NO: 2), BoNT/B3 (SEQ ID NO: 3), BoNT/B4 (SEQ ID NO: 4), BoNT/B5 (SEQ ID NO: 5), BoNT/B6 (SEQ ID NO: 6), BoNT/B7 (SEQ ID NO: 7), and BoNT/B8 (SEQ ID NO: 8), with substitution mutation(s) at positions corresponding to 1248 or 1249 in SEQ ID NO: 1. The skilled artisan will be able to determine the positions of the substitution modifications in each subtype based on his/her knowledge in protein homology, with or without the assistance of a sequence alignment software.

In some embodiments, the amino acid residues in any of BoNT/B1-BoNT/B8 at positions corresponding to 1248 or 1249 of BoNT/B1 may each be substituted by Tryptophan (W), Phenylalanine (F), Tyrosine (Y), or Histidine (H). In some embodiments, one of the two residues is substituted. In some embodiments, both residues are substituted. In some embodiments, the amino acid residues at positions corresponding to 1248 and 1249 of BoNT/B1 are both substituted with a W.

In some embodiments, the modified BoNT polypeptide comprises a modified receptor binding domain from BoNT/B1, comprising substitution mutation(s) in I1248 or V1249. Thus, the modified BoNT/B1 receptor binding domain may comprise any of the following mutations: I1248F; I1248Y; I1248H; I1248W; V1249W; V1249F; V1249Y; V1249H; I1248W/V1249F; I1248W/V1249Y; I1248W/V1249H; I1248F/V1249Y; I1248F/V1249H; I1248Y/V1249H; I1248F/V1249W; I1248Y/V1249W; I1248H/V1249W; I1248Y/V1249F; I1248H/V1249F; or I1248H/V1249Y ("/" indicates double mutation). In some embodiments, the modified BoNT polypeptide comprising the modified receptor binding domain of BoNT/B1 may comprise the amino acid sequence set forth in SEQ ID NO: 1 and further comprise any of the above mentioned substitution mutations. For example, the modified BoNT polypeptide may comprise the amino acid sequence set forth in SEQ ID NO: 1 and comprise an I1248W mutation. In another example, the modified BoNT polypeptide may comprise the amino acid sequence set forth in SEQ ID NO: 1 and comprise I1248W/V1249W mutations. An exemplary amino acid sequence of a BoNT/B1 with double substitution mutations I1248W/V1249W is provided (SEQ ID NO: 33). The examples provided herein are for illustration purpose only and are not meant to be limiting.

In some embodiments, the modified BoNT polypeptide comprises a modified receptor binding domain from BoNT/B2, comprising substitution mutation(s) in I1248 or V1249. Thus, the modified BoNT/B2 receptor binding domain may comprise any of the following mutations: I1248F; I1248Y; I1248H; I1248W; V1249W; V1249F; V1249Y; V1249H; I1248W/V1249F; I1248W/V1249Y; I1248W/V1249H; I1248F/V1249Y; I1248F/V1249H; I1248Y/V1249H; I1248F/V1249W; I1248Y/V1249W; I1248H/V1249W; I1248Y/V1249F; I1248H/V1249F; or I1248H/V1249Y ("/" indicates double mutation). In some embodiments, the modified BoNT polypeptide comprising the modified receptor binding domain of BoNT/B2 may comprise the amino acid sequence set forth in SEQ ID NO: 2 and further comprise any of the above mentioned substitution mutations. For example, the modified BoNT polypeptide may comprise the amino acid sequence set forth in SEQ ID NO: 2 and comprise an I1248W mutation. In another example, the modified BoNT polypeptide may comprise the amino acid sequence set forth in SEQ ID NO: 2 and comprise I1248W/V1249W mutations. The examples provided herein are for illustration purpose only and are not meant to be limiting.

In some embodiments, the modified BoNT polypeptide comprises a modified receptor binding domain from BoNT/B3, comprising substitution mutation(s) in I1248 or V1249. Thus, the modified BoNT/B3 receptor binding domain may comprise any of the following mutations: I1248F; I1248Y; I1248H; I1248W; V1249W; V1249F; V1249Y; V1249H; I1248W/V1249F; I1248W/V1249Y; I1248W/V1249H; I1248F/V1249Y; I1248F/V1249H; I1248Y/V1249H; I1248F/V1249W; I1248Y/V1249W; I1248H/V1249W; I1248Y/V1249F; I1248H/V1249F; or I1248H/V1249Y ("/" indicates double mutation). In some embodiments, the modified BoNT polypeptide comprising the modified receptor binding domain of BoNT/B3 may comprise the amino acid sequence set forth in SEQ ID NO: 3 and further comprise any of the above mentioned substitution mutations. For example, the modified BoNT polypeptide may comprise the amino acid sequence set forth in SEQ ID NO: 3 and comprise an I1248W mutation. In another example, the modified BoNT polypeptide may comprise the amino acid sequence set forth in SEQ ID NO: 3 and comprise I1248W/V1249W mutations. The examples provided herein are for illustration purpose only and are not meant to be limiting.

In some embodiments, the modified BoNT polypeptide comprises a modified receptor binding domain from BoNT/B4, comprising substitution mutation(s) in V1248 or L1249. Thus, the modified BoNT/B4 receptor binding domain may comprise any of the following mutations: V1248F; V1248Y; V1248H; V1248W; L1249W; L1249F; L1249Y; L1249H; L1248W/L1249F; V1248W/L1249Y; V1248W/L1249H; V1248F/L1249Y; V1248F/L1249H; V1248Y/L1249H; V1248F/L1249W; V1248Y/L1249W; V1248H/L1249W; V1248Y/L1249F; V1248H/L1249F; or V1248H/L1249Y ("/" indicates double mutation). In some embodiments, the modified BoNT polypeptide comprising the modified receptor binding domain of BoNT/B4 may comprise the amino acid sequence set forth in SEQ ID NO: 4 and further comprise any of the above mentioned substitution mutations. For example, the modified BoNT polypeptide may comprise the amino acid sequence set forth in SEQ ID NO: 4 and comprise an V1248W mutation. In another example, the modified BoNT polypeptide may comprise the amino acid sequence set forth in SEQ ID NO: 4 and comprise V1248W/L1249W mutations. The examples provided herein are for illustration purpose only and are not meant to be limiting.

In some embodiments, the modified BoNT polypeptide comprises a modified receptor binding domain from BoNT/B5, comprising substitution mutation(s) in I1248 or V1249. Thus, the modified BoNT/B5 receptor binding domain may comprise any of the following mutations: I1248F; I1248Y; I1248H; I1248W; V1249W; V1249F; V1249Y; V1249H; I1248W/V1249F; I1248W/V1249Y; I1248W/V1249H; I1248F/V1249Y; I1248F/V1249H; I1248Y/V1249H; I1248F/V1249W; I1248Y/V1249W; I1248H/V1249W; I1248Y/V1249F; I1248H/V1249F; or I1248H/V1249Y ("/" indicates double mutation). In some embodiments, the modified BoNT polypeptide comprising the modified receptor binding domain of BoNT/B5 may comprise the amino acid sequence set forth in SEQ ID NO: 5 and further comprise any of the above mentioned substitution mutations. For example, the modified BoNT polypeptide may comprise the amino acid sequence set forth in SEQ ID NO: 5 and comprise an I1248W mutation. In another example, the modified BoNT polypeptide may comprise the amino acid sequence set forth in SEQ ID NO: 5 and comprise I1248W/V1249W mutations. The examples provided herein are for illustration purpose only and are not meant to be limiting.

In some embodiments, the modified BoNT polypeptide comprises a modified receptor binding domain from BoNT/B6, comprising substitution mutations in I1248 or V1249. Thus, the modified BoNT/B6 receptor binding domain may comprise any of the following mutations: I1248F; I1248Y; I1248H; I1248W; V1249W; V1249F; V1249Y; V1249H; I1248W/V1249F; I1248W/V1249Y; I1248W/V1249H; I1248F/V1249Y; I1248F/V1249H; I1248Y/V1249H; I1248F/V1249W; I1248Y/V1249W; I1248H/V1249W; I1248Y/V1249F; I1248H/V1249F; or I1248H/V1249Y ("/" indicates double mutation). In some embodiments, the modified BoNT polypeptide comprising the modified receptor binding domain of BoNT/B6 may comprise the amino acid sequence set forth in SEQ ID NO: 6 and further comprise any of the above mentioned substitution mutations. For example, the modified BoNT polypeptide may comprise the amino acid sequence set forth in SEQ ID NO: 6 and comprise an I1248W mutation. In another example, the modified BoNT polypeptide may comprise the amino acid sequence set forth in SEQ ID NO: 6 and comprise I1248W/V1249W mutations. The examples provided herein are for illustration purpose only and are not meant to be limiting.

In some embodiments, the modified BoNT polypeptide comprises a modified receptor binding domain from BoNT/B7, comprising substitution mutations in I1248 or L1249. Thus, the modified BoNT/B7 receptor binding domain may comprise any of the following mutations: I1248F; I1248Y; I1248H; I1248W; L1249W; L1249F; L1249Y; L1249H; I1248W/L1249F; I1248W/L1249Y; I1248W/L1249H; I1248F/L1249Y; I1248F/L1249H; I1248Y/L1249H; I1248F/L1249W; I1248Y/L1249W; I1248H/L1249W; I1248Y/L1249F; I1248H/L1249F; or I1248H/L1249Y ("/" indicates double mutation). In some embodiments, the modified BoNT polypeptide comprising the modified receptor binding domain of BoNT/B7 may comprise the amino acid sequence set forth in SEQ ID NO: 7 and further comprise any of the above mentioned substitution mutations. For example, the modified BoNT polypeptide may comprise the amino acid sequence set forth in SEQ ID NO: 7 and comprise an I1248W mutation. In another example, the modified BoNT polypeptide may comprise the amino acid sequence set forth in SEQ ID NO: 7 and comprise I1248W/L1249W mutations. The examples provided herein are for illustration purpose only and are not meant to be limiting.

In some embodiments, the modified BoNT polypeptide comprises a modified receptor binding domain from BoNT/B8, comprising substitution mutations in F1249 or V1250. Thus, the modified BoNT/B8 receptor binding domain may comprise any of the following mutations: F1249Y; F1249H; F1249W; V1250W; V1250F; V1250Y; V1250H; F1249W/V1250F; F1249W/V1250Y; F1249W/V1250H; F1249Y/V1250H; F1249Y/V1250W; F1249H/V1250W; F1249Y/V1250F; F1249H/V1250F; or F1249H/V1250Y ("/" indicates double mutation). In some embodiments, the modified BoNT polypeptide comprising the modified receptor binding domain of BoNT/B8 may comprise the amino acid sequence set forth in SEQ ID NO: 8 and further comprise any of the above mentioned substitution mutations. For example, the modified BoNT polypeptide may comprise the amino acid sequence set forth in SEQ ID NO: 8 and comprise an F1249W mutation. In another example, the modified BoNT polypeptide may comprise the amino acid sequence set forth in SEQ ID NO: 8 and comprise F1249W/V1250W mutations. The examples provided herein are for illustration purpose only and are not meant to be limiting.

In some embodiments, the modified BoNT polypeptide of the present disclosure comprises an amino acid sequence of any one of SEQ ID NO: 1-8, having the amino acid substitutions described herein. In some embodiments, the modified BoNT polypeptide of the present disclosure comprises an amino acid sequence that has at least 85% identify to any one of SEQ ID NO: 1-8, having the amino acid substitutions described herein. For example, the modified BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 1-8, having one or more substitution mutation(s) at positions 1248 or 1249 in any one of SEQ ID NO: 1-7, or one or more substitution mutation(s) at positions 1249 or 1250 in SEQ ID NO: 8. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any of SEQ ID NOs: 1-8, having amino acid substitution mutation(s) at positions 1248 or 1249 in any one of SEQ ID NOs: 1-7, or positions 1249 or 1250 in SEQ ID NO: 8. In some embodiments, the modified BoNT polypeptide consists of the amino acid sequence of any of SEQ ID NOs: 1-8, having amino acid substitution mutation(s) at positions corresponding to 1248 or 1249 in BoNT/B1 (SEQ ID NO: 1).

In some embodiments, the modified BoNT polypeptide comprises an amino acid sequence of SEQ ID NO: 33. In some embodiments, the modified BoNT polypeptide of the present disclosure comprises an amino acid sequence that has at least 85% identify to SEQ ID NO: 33. For example, the modified BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 33. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to SEQ ID NO: 33. In some embodiments, the modified BoNT polypeptide consists of the amino acid sequence of SEQ ID NO: 33.

In some embodiments, the modified BoNT polypeptides of the present disclosure may be a modified receptor binding domain of BoNT/B (e.g., the receptor binding domain of BoNT/B1, BoNT/B2, BoNT/B3. BoNT/B4, BoNT/B5, BoNT/B6, BoNT/B7, or BoNT/B8) comprising substitution mutation(s) at positions corresponding to 1248 or 1249 in SEQ ID NO: 1. The skilled artisan will be able to determine the positions of the substitution modifications in each subtype based on his/her knowledge in protein homology, with or without the assistance of a sequence alignment software.

In some embodiments, the amino acid residues in the receptor binding domains of any of BoNT/B1-BoNT/B8 at positions corresponding to 1248 or 1249 of BoNT/B1 may each be substituted by Tryptophan (W), Phenylalanine (F), Tyrosine (Y), or Histidine (H). In some embodiments, either one of the two residues is substituted. In some embodiments, both residues are substituted. In some embodiments, the amino acid residues at positions corresponding to 1248 or 1249 of BoNT/B1 are substituted with a W.

The sequences of the receptor binding domains of BoNT/B1-B8 are provided in SEQ ID NOs: 9-16, respectively. The substitution mutation(s) are made at positions 389 or 390 in any of SEQ ID NOs: 9-15, or positions 390 and 391 in SEQ ID NO: 16. Thus, for example, without limitation, in some embodiments, positions 389 and 390 in any of SEQ ID NOs: 9-15 are substituted with a W.

In some embodiments, the modified BoNT polypeptide comprises a modified receptor binding domain from BoNT/B1, comprising substitution mutation(s) in I389 or V390. The modified BoNT/B1 receptor binding domain may comprise any of the following mutations: I389F; I389Y; I389H; I389W; V390W; V390F; V390Y; V390H; I389W/V390F; I389W/V390Y; I389W/V390H; I389F/V390Y; I389F/V390H; I389Y/V390H; I389F/V390W; I389Y/V390W; I389H/V390W; I389Y/V390F; I389H/V390F; or I389H/V390Y ("/" indicates double mutation). For example, the modified BoNT polypeptide may comprise the amino acid sequence set forth in SEQ ID NO: 9 and comprise an I389W mutation. In another example, the modified BoNT polypeptide may comprise the amino acid sequence set forth in SEQ ID NO: 9 and comprise I389W/V390W mutations. In some embodiments, the modified BoNT may comprise the amino acid sequence of SEQ ID NO: 34. The examples provided herein are for illustration purpose only and are not meant to be limiting.

In some embodiments, the modified BoNT polypeptide comprises a modified receptor binding domain from BoNT/B2, comprising substitution mutation(s) in 1389 or V390. The modified BoNT/B2 receptor binding domain may comprise any of the following mutations: I389F; I389Y; I389H; I389W; V390W; V390F; V390Y; V390H; I389W/V390F; I389W/V390Y; I389W/V390H; I389F/V390Y; I389F/V390H; I389Y/V390H; I389F/V390W; I389Y/V390W; I389H/V390W; I389Y/V390F; I389H/V390F; or I389H/V390Y ("/" indicates double mutation). For example, the modified BoNT polypeptide may comprise the amino acid sequence set forth in SEQ ID NO: 10 and comprise an I389W mutation. In another example, the modified BoNT polypeptide may comprise the amino acid sequence set forth in SEQ ID NO: 10 and comprise I389W/V390W mutations. The examples provided herein are for illustration purpose only and are not meant to be limiting.

In some embodiments, the modified BoNT polypeptide comprises a modified receptor binding domain from BoNT/B3, comprising substitution mutation(s) in 1389 or V390. The modified BoNT/B3 receptor binding domain may comprise any of the following mutations: I389F; I389Y; I389H; I389W; V390W; V390F; V390Y; V390H; I389W/V390F; I389W/V390Y; I389W/V390H; I389F/V390Y; I389F/V390H; I389Y/V390H; I389F/V390W; I389Y/V390W; I389H/V390W; I389Y/V390F; I389H/V390F; or I389H/V390Y ("/" indicates double mutation). For example, the modified BoNT polypeptide may comprise the amino acid sequence set forth in SEQ ID NO: 11 and comprise an I389W mutation. In another example, the modified BoNT polypeptide may comprise the amino acid sequence set forth in SEQ ID NO: 11 and comprise I389W/V390W mutations. The examples provided herein are for illustration purpose only and are not meant to be limiting.

In some embodiments, the modified BoNT polypeptide comprises a modified receptor binding domain from BoNT/B4, comprising substitution mutation(s) in V389 or L390. The modified BoNT/B4 receptor binding domain may comprise any of the following mutations: V389F; V389Y; V389H; V389W; L390W; L390F; L390Y; L390H; L389W/L390F; V389W/L390Y; V389W/L390H; V389F/L390Y; V389F/L390H; V389Y/L390H; V389F/L390W; V389Y/L390W; V389H/L390W; V389Y/L390F; V389H/L390F; or V389H/L390Y ("/" indicates double mutation). For example, the modified BoNT polypeptide may comprise the amino acid sequence set forth in SEQ ID NO: 12 and comprise an V389W mutation. In another example, the modified BoNT polypeptide may comprise the amino acid sequence set forth in SEQ ID NO: 12 and comprise V389W/L390W mutations. The examples provided herein are for illustration purpose only and are not meant to be limiting.

In some embodiments, the modified BoNT polypeptide comprises a modified receptor binding domain from BoNT/B5, comprising substitution mutation(s) in 1389 or V390. The modified BoNT/B5 receptor binding domain may comprise any of the following mutations: I389F; I389Y; I389H; I389W; V390W; V390F; V390Y; V390H; I389W/V390F; I389W/V390Y; I389W/V390H; I389F/V390Y; I389F/V390H; I389Y/V390H; I389F/V390W; I389Y/V390W; I389H/V390W; I389Y/V390F; I389H/V390F; or I389H/V390Y ("/" indicates double mutation). For example, the modified BoNT polypeptide may comprise the amino acid sequence set forth in SEQ ID NO: 13 and comprise an I389W mutation. In another example, the modified BoNT polypeptide may comprise the amino acid sequence set forth in SEQ ID NO: 13 and comprise I389W/V390W mutations. The examples provided herein are for illustration purpose only and are not meant to be limiting.

In some embodiments, the modified BoNT polypeptide comprises a modified receptor binding domain from BoNT/B6, comprising substitution mutation(s) in 1389 or V390. The modified BoNT/B6 receptor binding domain may comprise any of the following mutations: I389F; I389Y; I389H; I389W; V390W; V390F; V390Y; V390H; I389W/V390F; I389W/V390Y; I389W/V390H; I389F/V390Y; I389F/V390H; I389Y/V390H; I389F/V390W; I389Y/V390W; I389H/V390W; I389Y/V390F; I389H/V390F; or I389H/V390Y ("/" indicates double mutation). For example, the modified BoNT polypeptide may comprise the amino acid sequence set forth in SEQ ID NO: 14 and comprise an I389W mutation. In another example, the modified BoNT polypeptide may comprise the amino acid sequence set forth in SEQ ID NO: 14 and comprise I389W/V390W mutations. The examples provided herein are for illustration purpose only and are not meant to be limiting.

In some embodiments, the modified BoNT polypeptide comprises a modified receptor binding domain from BoNT/B7, comprising substitution mutation(s) in 1389 or L390. The modified BoNT/B7 receptor binding domain may comprise any of the following mutations: I389F; I389Y; I389H; I389W; L390W; L390F; L390Y; L390H; I389W/L390F; I389W/L390Y; I389W/L390H; I389F/L390Y; I389F/L390H; I389Y/L390H; I389F/L390W; I389Y/L390W; I389H/L390W; I389Y/L390F; I389H/L390F; or I389H/L390Y ("/" indicates double mutation). For example, the modified BoNT polypeptide may comprise the amino acid sequence set forth in SEQ ID NO: 15 and comprise an I389W mutation. In another example, the modified BoNT polypeptide may comprise the amino acid sequence set forth in SEQ ID NO: 15 and comprise I389W/L390W mutations. The examples provided herein are for illustration purpose only and are not meant to be limiting.

In some embodiments, the modified BoNT polypeptide comprises a modified receptor binding domain from BoNT/B8, comprising substitution mutation(s) in F390 or V391. The modified BoNT/B8 receptor binding domain may comprise any of the following mutations: F390Y; F390H; F390W; V391W; V391F; V391Y; V391H; F390W/V391F; F390W/V391Y; F390W/V391H; F390Y/V391H; F390Y/V391W; F390H/V391W; F390Y/V391F; F390H/V391F; or F390H/V391Y ("/" indicates double mutation). For example, the modified BoNT polypeptide may comprise the amino acid sequence set forth in SEQ ID NO: 16 and comprise an F390W mutation. In another example, the modified BoNT polypeptide may comprise the amino acid sequence set forth in SEQ ID NO: 16 and comprise F390W/V391W mutations. The examples provided herein are for illustration purpose only and are not meant to be limiting.

In some embodiments, the modified BoNT polypeptide of the present disclosure comprises and amino acid sequence of any one of SEQ ID NO: 9-16, having the amino acid substitutions described herein. In some embodiments, the modified BoNT polypeptide of the present disclosure comprises and amino acid sequence that has at least 85% identify to any one of SEQ ID NO: 9-16, having the amino acid substitutions described herein. For example, the modified BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 9-16, having one or more substitution mutation(s) at positions 389 or 390 in any one of SEQ ID NO: 9-15, or one or more substitution mutation(s) at positions 390 or 391 in SEQ ID NO: 16. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any of SEQ ID NOs: 9-16, having amino acid substitution mutation(s) at positions 389 or 390 in any one of SEQ ID NO: 9-15, or one or more substitution mutation(s) at positions 390 or 391 in SEQ ID NO: 16. In some embodiments, the modified BoNT polypeptide consists of the amino acid sequence of any of SEQ ID NOs: 9-16, having amino acid substitution mutation(s) at positions 389 or 390 in any one of SEQ ID NO: 9-15, or one or more substitution mutation(s) at positions 390 or 391 in SEQ ID NO: 16.

In some embodiments, the modified BoNT polypeptide comprises an amino acid sequence of SEQ ID NO: 34. In some embodiments, the modified BoNT polypeptide of the present disclosure comprises an amino acid sequence that has at least 85% identify to SEQ ID NO: 34. For example, the modified BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 34. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to SEQ ID NO: 34. In some embodiments, the modified BoNT polypeptide consists of the amino acid sequence of SEQ ID NO: 34.

In some embodiments, the modified BoNT polypeptides of the present disclosure may be a chimeric BoNT polypeptide comprising modified receptor binding domains of BoNT/B (e.g., the receptor binding domain of BoNT/B1, BoNT/B2, BoNT/B3. BoNT/B4, BoNT/B5, BoNT/B6, BoNT/B7, or BoNT/B8) comprising substitution mutation(s) at positions corresponding 1248 or 1249 in SEQ ID NO: 1.

In a non-limiting example, a chimeric BoNT/BA may be generated by replacing the receptor binding domain of BoNT/A with the modified receptor binding domain of BoNT/B described herein. It is to be understood that the receptor binding domain of any of BoNT/B1 to BoNT/B8 is suitable for the chimeric toxin. Similarly, any of the subtypes of BoNT/A is suitable for the chimera toxin (e.g., BoNT/A1, BoNT/A2, BoNT/A3, BoNT/A4, BoNT/A5, BoNT/A6, BoNT/A7, and BoNT/A8). It is to be appreciated that when BoNT/A is referred to, it encompasses all the BoNT/A subtypes).

Thus, a chimeric BoNT of the present disclosure, may be any of the following combinations: BoNT/A1-B1, BoNT/A2-B1, BoNT/A3-B1, BoNT/A4-B1, BoNT/A5-B1, BoNT/A7-B1, BoNT/A7-B1, BoNT/A8-B1, BoNT/A2-B1, BoNT/A2-B2, BoNT/A2-B3, BoNT/A2-B4, BoNT/A2-B5, BoNT/A2-B6, BoNT/A2-B7, BoNT/A2-B8, BoNT/A3-B1, BoNT/A3-B2, BoNT/A3-B3, BoNT/A3-B4, BoNT/A3-B5, BoNT/A3-B6, BoNT/A3-B7, BoNT/A3-B8, BoNT/A4-B1, BoNT/A4-B2, BoNT/A4-B3, BoNT/A4-B4, BoNT/A4-B5, BoNT/A4-B6, BoNT/A4-B7, BoNT/A4-B8, BoNT/A5-B1, BoNT/A5-B2, BoNT/A5-B3, BoNT/A5-B4, BoNT/A5-B5, BoNT/A5-B6, BoNT/A5-B7, BoNT/A5-B8, BoNT/A6-B1, BoNT/A6-B2, BoNT/A6-B3, BoNT/A6-B4, BoNT/A6-B5, BoNT/A6-B6, BoNT/A6-B7, BoNT/A6-B8, BoNT/A7-B1, BoNT/A7-B2, BoNT/A7-B3, BoNT/A7-B4, BoNT/A7-B5, BoNT/A7-B6, BoNT/A7-B7, BoNT/A7-B8, BoNT/A8-B1, BoNT/A8-B2, BoNT/A8-B3, BoNT/A8-B4, BoNT/A8-B5, BoNT/A8-B6, BoNT/A8-B7, or BoNT/A8-B8. It is appreciated that when "BoNT/AB" is referred to, it encompasses all the combinations of the subtypes described herein. The skilled artisan will be able to determine the positions of the substitution modifications in each chimeric toxin, based on his/her knowledge in protein homology, with or without the assistance of a sequence alignment software.

To generate the chimeric toxins, e.g., the BoNT/AB toxin, a fragment of BoNT/A comprising amino acid of about 1-872 of any of BoNT/A1-BoNT/A8 (SEQ ID NOs: 38-45) is fused to the receptor binding domain of any of BoNT/B (e.g., the receptor binding domains of any of BoNT/B1-B8). The receptor binding domains of BoNT/B correspond to amino acids of about 860-1291 of BoNT/B1. It is to be understood that the border of the BoNT/A fragment and/or the receptor binding domain of BoNT/B may vary by 1-10 amino acids. For example, the BoNT/A fragment that may be used for the chimeric toxin may comprise amino acid 1-872, 1-871, 1-870, 1-869, 1-868, 1-867, 1-866, 1-865, 1-864, 1-863, 1-873, 1-874, 1-875, 1-876, 1-877, 1-878, 1-879, 1-880, 1-881, or 1-882 of any of BoNT/A1-A8. Similarly, the receptor binding domain of BoNT/B that may be used for the chimeric toxin may comprise amino acid 861-1291, 862-1291, 863-1291, 864-1291, 865-1291, 866-1291, 867-1291, 868-1291, 869-1291, 870-1291, 860-1291, 859-1291, 858-1291, 857-1291, 856-1291, 855-1291, 854-1291, 853-1291, 852-1291, or 851-1291 of any of BoNT/B1-B8. The methods of fusing the fragments of BoNT/A and BoNT/B are standard recombinant techniques that are well known to one skilled in the art.

Non-limiting, exemplary sequences of BoNTA1-B1, BoNT/A2-B1, BoNT/A3-B1, BoNT/A4-B1, BoNT/A5-B1, BoNT/A6-B1, BoNT/A7-B1, and BoNT/A8-B1 are provided as SEQ ID NO: 17-24, respectively. The positions corresponding to positions 1248 or 1249 in BoNT/B1 are positions 1261 or 1262 in any of SEQ ID NOs: 17-24.

In some embodiments, the chimeric BoNT polypeptide comprises a BoNT/A1 polypeptide with its receptor binding domain replaced by the modified receptor binding domain from BoNT/B1 (BoNT/A1-B1), comprising substitution mutation(s) at positions 1261 or 1262. The chimeric BoNT/A1-B1 may comprise any of the following mutations: I1261F; I1261Y; I1261H; I1261W; V1262W; V1262F; V1262Y; V1262H; I1261W/V1262F; I1261W/V1262Y; I1261W/V1262H; I1261F/V1262Y; I1261F/V1262H; I1261Y/V1262H; I1261F/V1262W; I1261Y/V1262W; I1261H/V1262W; I1261Y/V1262F; I1261H/V1262F; or I1261H/V1262Y ("/" indicates double mutation). For example, the chimeric BoNT polypeptide may comprise the amino acid sequence set forth in SEQ ID NO: 17 and comprise an I1261W mutation. In another example, the chimeric BoNT polypeptide may comprise the amino acid sequence set forth in SEQ ID NO: 17 and comprise I1261W/V1262W mutations. In some embodiments, the chimeri BoNT polypeptide may comprise an amino acid sequence of SEQ ID NO: 35. The examples here are for illustration purpose only and are not meant to be limiting.

In some embodiments, the chimeric BoNT polypeptide comprises a BoNT/A2 polypeptide with its receptor binding domain replaced by the modified receptor binding domain from BoNT/B1 (BoNT/A2-B1), comprising substitution mutation(s) in positions 1261 or 1262. The chimeric BoNT/A2-B1 may comprise any of the following mutations: I1261F; I1261Y; I1261H; I1261W; V1262W; V1262F; V1262Y; V1262H; I1261W/V1262F; I1261W/V1262Y; I1261W/V1262H; I1261F/V1262Y; I1261F/V1262H; I1261Y/V1262H; I1261F/V1262W; I11261Y/V1262W; I1261H/V1262W; I1261Y/V1262F; I1261H/V1262F; or I1261H/V1262Y ("/" indicates double mutation). For example, the chimeric BoNT polypeptide may comprise the amino acid sequence set forth in SEQ ID NO: 18 and comprise an I1261W mutation. In another example, the chimeric BoNT polypeptide may comprise the amino acid sequence set forth in SEQ ID NO: 18 and comprise I1261W/V1262W mutations. In some embodiments, the chimeri BoNT polypeptide may comprise an amino acid sequence of SEQ ID NO: 36. The examples here are for illustration purpose only and are not meant to be limiting.

In some embodiments, the chimeric BoNT polypeptide comprises a BoNT/A3 polypeptide with its receptor binding domain replaced by the modified receptor binding domain from BoNT/B1 (BoNT/A3-B1), comprising substitution mutation(s) in positions 1261 or 1262. The chimeric BoNT/A3-B1 may comprise any of the following mutations: I1261F; I1261Y; I1261H; I1261W; V1262W; V1262F; V1262Y; V1262H; I1261W/V1262F; I1261W/V1262Y; I1261W/V1262H; I1261F/V1262Y; I1261F/V1262H; I1261Y/V1262H; I1261F/V1262W; I11261Y/V1262W; I1261H/V1262W; I1261Y/V1262F; I1261H/V1262F; or I1261H/V1262Y ("/" indicates double mutation). For example, the chimeric BoNT polypeptide may comprise the amino acid sequence set forth in SEQ ID NO: 19 and comprise an I1261W mutation. In another example, the chimeric BoNT polypeptide may comprise the amino acid sequence set forth in SEQ ID NO: 19 and comprise I1261W/V1262W mutations. The examples here are for illustration purpose only and are not meant to be limiting.

In some embodiments, the chimeric BoNT polypeptide comprises a BoNT/A4 polypeptide with its receptor binding domain replaced by the modified receptor binding domain from BoNT/B1 (BoNT/A4-B1), comprising substitution mutation(s) in positions 1261 or 1262. The chimeric BoNT/A4-B1 may comprise any of the following mutations: V1261F; V1261Y; V1261H; V1261W; L1262W; L1262F; L1262Y; L1262H; L1261W/L1262F; V1261W/L1262Y; V1261W/L1262H; V1261F/L1262Y; V1261F/L1262H; V1261Y/L1262H; V1261F/L1262W; V1261Y/L1262W; V1261H/L1262W; V1261Y/L1262F; V1261H/L1262F; or V1261H/L1262Y ("/" indicates double mutation). For example, the chimeric BoNT polypeptide may comprise the amino acid sequence set forth in SEQ ID NO: 20 and comprise an V1261W mutation. In another example, the chimeric BoNT polypeptide may comprise the amino acid sequence set forth in SEQ ID NO: 20 and comprise V1261W/L1262W mutations. The examples here are for illustration purpose only and are not meant to be limiting.

In some embodiments, the chimeric BoNT polypeptide comprises a BoNT/A5 polypeptide with its receptor binding domain replaced by the modified receptor binding domain from BoNT/B1 (BoNT/A5-B1), comprising substitution mutation(s) in positions 1261 or 1262. The chimeric BoNT/A5-B1 may comprise any of the following mutations: I1261F; I1261Y; I1261H; I1261W; V1262W; V1262F; V1262Y; V1262H; I1261W/V1262F; I1261W/V1262Y; I1261W/V1262H; I1261F/V1262Y; I1261F/V1262H; I1261Y/V1262H; I1261F/V1262W; I1261Y/V1262W; I1261H/V1262W; I1261Y/V1262F; I1261H/V1262F; or I1261H/V1262Y ("/" indicates double mutation). For example, the chimeric BoNT polypeptide may comprise the amino acid sequence set forth in SEQ ID NO: 21 and comprise an I1261W mutation. In another example, the chimeric BoNT polypeptide may comprise the amino acid sequence set forth in SEQ ID NO: 21 and comprise I1261W/V1262W mutations. The examples here are for illustration purpose only and are not meant to be limiting.

In some embodiments, the chimeric BoNT polypeptide comprises a BoNT/A6 polypeptide with its receptor binding domain replaced by the modified receptor binding domain from BoNT/B1 (BoNT/A6-B1), comprising substitution mutation(s) in positions 1261 or 1262. The chimeric BoNT/A6-B1 may comprise any of the following mutations: I1261F; I1261Y; I1261H; I1261W; V1262W; V1262F; V1262Y; V1262H; I1261W/V1262F; I1261W/V1262Y; I11261W/V1262H; I1261F/V1262Y; I1261F/V1262H; I1261Y/V1262H; I1261F/V1262W; I1261Y/V1262W; I1261H/V1262W; I1261Y/V1262F; I1261H/V1262F; or I1261H/V1262Y ("/" indicates double mutation). For example, the chimeric BoNT polypeptide may comprise the amino acid sequence set forth in SEQ ID NO: 22 and comprise an I1261W mutation. In another example, the chimeric BoNT polypeptide may comprise the amino acid sequence set forth in SEQ ID NO: 22 and comprise I1261W/V1262W mutations. The examples here are for illustration purpose only and are not meant to be limiting.

In some embodiments, the chimeric BoNT polypeptide comprises a BoNT/A7 polypeptide with its receptor binding domain replaced by the modified receptor binding domain from BoNT/B1 (BoNT/A7-B1), comprising substitution mutation(s) in positions 1261 or 1262. The chimeric BoNT/A7-B1 may comprise any of the following mutations: I1261F; I1261Y; I11261H; I1261W; L1262W; L1262F; L1262Y; L1262H; I1261W/L1262F; I1261W/L1262Y; I1261W/L1262H; I1261F/L1262Y; I1261F/L1262H; I1261Y/L1262H; I1261F/L1262W; I1261Y/L1262W; I1261H/L1262W; I1261Y/L1262F; I1261H/L1262F; or I1261H/L1262Y ("/" indicates double mutation). For example, the chimeric BoNT polypeptide may comprise the amino acid sequence set forth in SEQ ID NO: 23 and comprise an I1261W mutation. In another example, the chimeric BoNT polypeptide may comprise the amino acid sequence set forth in SEQ ID NO: 23 and comprise I1261W/L1262W mutations. The examples here are for illustration purpose only and are not meant to be limiting.

In some embodiments, the chimeric BoNT polypeptide comprises a BoNT/A8 polypeptide with its receptor binding domain replaced by the modified receptor binding domain from BoNT/B1 (BoNT/A8-B1), comprising substitution mutation(s) in positions 1261 or 1262. The chimeric BoNT/A8-B1 may comprise any of the following mutations: F1261Y; F1261H; F1261W; V1262W; V1262F; V1262Y; V1262H; F1261W/V1262F; F1261W/V1262Y; F1261W/V1262H; F1261Y/V1262H; F1261Y/V1262W; F1261H/V1262W; F1261Y/V1262F; F1261H/V1262F; or F1261H/V1262Y ("/" indicates double mutation). For example, the chimeric BoNT polypeptide may comprise the amino acid sequence set forth in SEQ ID NO: 24 and comprise an F1261W mutation. In another example, the chimeric BoNT polypeptide may comprise the amino acid sequence set forth in SEQ ID NO: 24 and comprise F1261W/V1262W mutations. The examples here are for illustration purpose only and are not meant to be limiting.

In some embodiments, the chimeric BoNT polypeptide of the present disclosure comprises and amino acid sequence of any of SEQ ID NOs: 17-24, having the amino acid substitutions described herein. In some embodiments, the chimeric BoNT polypeptide of the present disclosure comprises and amino acid sequence that has at least 85% identify to any one of SEQ ID NOs: 17-24, having the amino acid substitutions described herein. For example, the chimeric BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 17-24, having one or more substitution mutation(s) at positions 1261 or 1262 in any one of SEQ ID NOs: 17-24. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any of SEQ ID NOs: 17-24, having amino acid substitution mutation(s) at positions 1261 or 1262 in any one of SEQ ID NOs: 17-24. In some embodiments, the chimeric BoNT polypeptide consists of the amino acid sequence of any of SEQ ID NOs: 17-24, having amino acid substitution mutation(s) at positions 1261 or 1262 in any one of SEQ ID NOs: 17-24.

In some embodiments, the chimeric BoNT polypeptide comprises an amino acid sequence of SEQ ID NO: 35 or SEQ ID NO: 36. In some embodiments, the modified BoNT polypeptide of the present disclosure comprises an amino acid sequence that has at least 85% identify to SEQ ID NO: 35 or SEQ ID NO: 36. For example, the modified BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 35 or SEQ ID NO: 36. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to SEQ ID NO: 35 or SEQ ID NO: 36. In some embodiments, the modified BoNT polypeptide consists of the amino acid sequence of SEQ ID NO: 35 or SEQ ID NO: 36.

The modified BoNT polypeptides of the present disclosure (e.g., the modified full-length BoNT/B, the modified receptor binding domain of BoNT/B, or BoNT/BA chimeric toxins) may comprise additional mutations that further enhance their binding affinities to the target cells. Examples of such mutations are described in WO2013180799, the entire contents of which is hereby incorporated by reference. Thus, the modified BoNT polypeptides of the present disclosure may further comprise a series of mutations in BoNT/B receptor binding domain in positions corresponding to 1178, 1191 or 1199 in BoNT/B1 (e.g., E1191M/S1199Y, E1191M/S1199W, E1191M/W1178Q, E1191V/S1199Y, 1191V/S1199W, E1199V/W1178Q, or E1199Q/S1199Y), which significantly enhanced binding of BoNT/B to human Syt II.

In some embodiments, the modified BoNT polypeptides of the present disclosure further comprising these substitution mutations that enhance binding of the BoNT to human SytII, may comprise the amino acid sequence of any of SEQ ID NOs: 46-66. In some embodiments, the modified BoNT polypeptide comprises an amino acid sequence that has at least 85% identify to any of SEQ ID NOs: 46-66. For example, the modified BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any of SEQ ID NOs: 46-66. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any of SEQ ID NOs: 46-66. In some embodiments, the modified BoNT polypeptide consists of the amino acid sequence of any of SEQ ID NO: 46-66.

The amino acid substitution mutations described herein, e.g., I1248W/V1249W of BoNT/B1, create a loop that penetrates into the lipid membranes, which in turn enhances the binding of the BoNT to its target cells. Such loop is not otherwise present in the wild type BoNT/B. Thus, further provided herein are modified BoNT/B polypeptides that constitute the loop, corresponding to a fragment between amino acid 1245 and amino acid 1252 of BoNT/B1, having one or more substitution mutation(s) at positions corresponding to 1248 or 1249 in BoNT/B1. In some embodiments, the modified BoNT polypeptide comprises a fragment between amino acid 1245 and amino acid 1252 of BoNT/B1 (inclusive, SEQ ID NO: 25), having one or more substitution mutation(s) at positions corresponding to 4 or 5 in BoNT/B1 (positions 4 and 5 in SEQ ID NO: 25). Thus, the fragment may comprise any of the following mutations: I4F; I4Y; 14H; I4W; V5W; V5F; V5Y; V5H; I4W/V5F; I4W/V5Y; I4W/V5H; I4F/V5Y; 14F/V5H; I4Y/V5H; I4F/V5W; I4Y/V5W; I4H/V5W; I4Y/V5F; I4H/V5F; or I4H/V5Y ("/" indicates double mutation). For example, the modified BoNT polypeptide may comprise the amino acid sequence set forth in SEQ ID NO: 25 and comprise an I4W mutation. In another example, the modified BoNT polypeptide may comprise the amino acid sequence set forth in SEQ ID NO: 25 and comprise I4W/V5W mutations. In some embodiments, the modified BoNT of the present disclosure may comprise an amino acid sequence of SEQ ID NO: 37. The examples here are for illustration purpose only and are not meant to be limiting.

In some embodiments, the modified BoNT polypeptide comprises a fragment between amino acid 1245 and amino acid 1252 of BoNT/B2 (inclusive, SEQ ID NO: 26), having one or more substitution mutation(s) at positions corresponding to 4 or 5 in BoNT/B1 (positions 4 or 5 in SEQ ID NO: 26). Thus, the fragment may comprise any of the following mutations: I4F; I4Y; I4H; I4W; V5W; V5F; V5Y; V5H; I4W/V5F; I4W/V5Y; I4W/V5H; I4F/V5Y; I4F/V5H; I4Y/V5H; I4F/V5W; I4Y/V5W; I4H/V5W; I4Y/V5F; I4H/V5F; or I4H/V5Y ("/" indicates double mutation). For example, the modified BoNT polypeptide may comprise the amino acid sequence set forth in SEQ ID NO: 26 and comprise an I4W mutation. In another example, the modified BoNT polypeptide may comprise the amino acid sequence set forth in SEQ ID NO: 26 and comprise I4W/V5W mutations. The examples here are for illustration purpose only and are not meant to be limiting.

In some embodiments, the modified BoNT polypeptide comprises a fragment between amino acid 1245 and amino acid 1252 of BoNT/B3 (inclusive, SEQ ID NO: 27), having one or more substitution mutation(s) at positions corresponding to 4 or 5 in BoNT/B1 (positions 4 or 5 in SEQ ID NO: 27). Thus, the fragment may comprise any of the following mutations: I4F; I4Y; I4H; I4W; V5W; V5F; V5Y; V5H; I4W/V5F; I4W/V5Y; I4W/V5H; I4F/V5Y; I4F/V5H; I4Y/V5H; I4F/V5W; I4Y/V5W; I4H/V5W; I4Y/V5F; I4H/V5F; or I4H/V5Y ("/" indicates double mutation). For example, the modified BoNT polypeptide may comprise the amino acid sequence set forth in SEQ ID NO: 27 and comprise an I4W mutation. In another example, the modified BoNT polypeptide may comprise the amino acid sequence set forth in SEQ ID NO: 27 and comprise I4W/V5W mutations. The examples here are for illustration purpose only and are not meant to be limiting.

In some embodiments, the modified BoNT polypeptide comprises a fragment between amino acid 1245 and amino acid 1252 of BoNT/B4 (inclusive, SEQ ID NO: 28), having one or more substitution mutation(s) at positions corresponding to 4 or 5 in BoNT/B1 (positions 4 or 5 in SEQ ID NO: 28). Thus, the fragment may comprise any of the following mutations: V4F; V4Y; V4H; V4W; L5W; L5F; L5Y; L5H; L4W/L5F; V4W/L5Y; V4W/L5H; V4F/L5Y; V4F/L5H; V4Y/L5H; V4F/L5W; V4Y/L5W; V4H/L5W; V4Y/L5F; V4H/L5F; or V4H/L5Y ("/" indicates double mutation). For example, the modified BoNT polypeptide may comprise the amino acid sequence set forth in SEQ ID NO: 28 and comprise an V4W mutation. In another example, the modified BoNT polypeptide may comprise the amino acid sequence set forth in SEQ ID NO: 28 and comprise V4W/L5W mutations. The examples here are for illustration purpose only and are not meant to be limiting.

In some embodiments, the modified BoNT polypeptide comprises a fragment between amino acid 1245 and amino acid 1252 of BoNT/B5 (inclusive, SEQ ID NO: 29), having one or more substitution mutation(s) at positions corresponding to 4 or 5 in BoNT/B1 (positions 4 or 5 in SEQ ID NO: 29). Thus, the fragment may comprise any of the following mutations: I4F; I4Y; I4H; I4W; V5W; V5F; V5Y; V5H; I4W/V5F; I4W/V5Y; I4W/V5H; I4F/V5Y; I4F/V5H; I4Y/V5H; I4F/V5W; I4Y/V5W; I4H/V5W; I4Y/V5F; I4H/V5F; or I4H/V5Y ("/" indicates double mutation). For example, the modified BoNT polypeptide may comprise the amino acid sequence set forth in SEQ ID NO: 29 and comprise an I4W mutation. In another example, the modified BoNT polypeptide may comprise the amino acid sequence set forth in SEQ ID NO: 29 and comprise I4W/V5W mutations. The examples here are for illustration purpose only and are not meant to be limiting.

In some embodiments, the modified BoNT polypeptide comprises a fragment between amino acid 1245 and amino acid 1252 of BoNT/B6 (inclusive, SEQ ID NO: 30), having one or more substitution mutation(s) at positions corresponding to 4 or 5 in BoNT/B1 (positions 4 or 5 in SEQ ID NO: 30). Thus, the fragment may comprise any of the following mutations: I4F; I4Y; I4H; I4W; V5W; V5F; V5Y; V5H; I4W/V5F; I4W/V5Y; I4W/V5H; I4F/V5Y; I4F/V5H; I4Y/V5H; I4F/V5W; I4Y/V5W; I4H/V5W; I4Y/V5F; I4H/V5F; or I4H/V5Y ("/" indicates double mutation). For example, the modified BoNT polypeptide may comprise the amino acid sequence set forth in SEQ ID NO: 30 and comprise an I4W mutation. In another example, the modified BoNT polypeptide may comprise the amino acid sequence set forth in SEQ ID NO: 30 and comprise I4W/V5W mutations. The examples here are for illustration purpose only and are not meant to be limiting.

In some embodiments, the modified BoNT polypeptide comprises a fragment between amino acid 1245 and amino acid 1252 of BoNT/B7 (inclusive, SEQ ID NO: 31), having one or more substitution mutation(s) at positions corresponding to 4 or 5 in BoNT/B1 (positions 4 or 5 in SEQ ID NO: 31). Thus, the fragment may comprise any of the following mutations: I4F; I4Y; I4H; I4W; L5W; L5F; L5Y; L5H; I4W/L5F; I4W/L5Y; I4W/L5H; I4F/L5Y; I4F/L5H; 14Y/L5H; I4F/L5W; I4Y/L5W; I4H/L5W; I4Y/L5F; I4H/L5F; or I4H/L5Y ("/" indicates double mutation). For example, the modified BoNT polypeptide may comprise the amino acid sequence set forth in SEQ ID NO: 31 and comprise an I4W mutation. In another example, the modified BoNT polypeptide may comprise the amino acid sequence set forth in SEQ ID NO: 31 and comprise I4W/L5W mutations. The examples here are for illustration purpose only and are not meant to be limiting.

In some embodiments, the modified BoNT polypeptide comprises a fragment between amino acid 1246 and amino acid 1253 of BoNT/B8 (inclusive, SEQ ID NO: 32), having one or more substitution mutation(s) at positions corresponding to 4 or 5 in BoNT/B1 (positions 4 or 5 in SEQ ID NO: 32). Thus, the fragment may comprise any of the following mutations: F4Y; F5H; F4W; V5W; V5F; V5Y; V5H; F4W/V5F; F4W/V5Y; F4W/V5H; F4Y/V5H; F4Y/V5W; F4H/V5W; F4Y/V5F; F4H/V5F; or F4H/V5Y ("/" indicates double mutation). For example, the modified BoNT polypeptide may comprise the amino acid sequence set forth in SEQ ID NO: 32 and comprise an F4W mutation. In another example, the modified BoNT polypeptide may comprise the amino acid sequence set forth in SEQ ID NO: 32 and comprise F4W/V5W mutations. The examples here are for illustration purpose only and are not meant to be limiting.

In some embodiments, the modified BoNT polypeptide of the present disclosure comprises an amino acid sequence of any of SEQ ID NOs: 25-32, having the amino acid substitutions described herein. In some embodiments, the modified BoNT polypeptide of the present disclosure comprises an amino acid sequence that has at least 85% identify to any one of SEQ ID NOs: 25-32, having the amino acid substitutions described herein. For example, the modified BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 25-32, having one or more substitution mutation(s) at positions 4 or 5 in any one of SEQ ID NOs: 25-32. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any of SEQ ID NOs: 25-32, having amino acid substitution mutation(s) at positions 4 or 5 in any of SEQ ID NOs: 25-32. In some embodiments, the modified BoNT polypeptide consists of the amino acid sequence of any of SEQ ID NOs: 25-32, having amino acid substitution mutation(s) at positions 4 or 5 any of SEQ ID NOs: 25-32.

In some embodiments, the modified BoNT polypeptide comprises an amino acid sequence of SEQ ID NO: 37. In some embodiments, the modified BoNT polypeptide of the present disclosure comprises an amino acid sequence that has at least 85% identify to SEQ ID NO: 37. For example, the modified BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 37. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to SEQ ID NO: 37. In some embodiments, the modified BoNT polypeptide consists of the amino acid sequence of SEQ ID NO: 37.

In other embodiments, the modified *Clostridial Botulinum* neurotoxin (BoNT) polypeptide comprises four domains: a) a protease domain; b) a protease cleavage site; c) a translocation domain; and d) a modified receptor binding domain of *Clostridial Botulinum* serotype B, comprising one or more substitution mutation(s) at positions corresponding to 1248 or 1249 in BoNT serotype B, strain 1 (BoNT/B1). It is to be understood that the modified receptor binding domain of BoNT/B may be from any of the BoNT/B subtypes, e.g., BoNT/B, BoNT/B2, BoNT/B3, BoNT/B4, BoNT/B5, BoNT/B6, BoNT/B7, or BoNT/B8.

In some embodiments, the modified receptor binding domain of (d) comprises one substitution mutation in any of the two residues described herein. In some embodiments, the one substitution mutation correspond to I1248F, I1248Y, I1248H, I1248W, V1249W, V1249F, V1249Y, or V1249H in BoNT/B1. In some embodiments, the modified receptor binding domain of (d) comprises two substitution mutations. In some embodiments, the two substitution mutations correspond to I1248W/V1249F, I1248W/V1249Y, I1248W/V1249H, I1248F/V1249Y, I1248F/V1249H, I1248Y/V1249H, I1248F/V1249W, I1248Y/V1249W, I1248H/V1249W, I1248Y/V1249F, I1248H/V1249F, or I1248H/V1249Y in BoNT/B1.

In some embodiments, the modified BoNT polypeptide is a chimeric toxin, wherein protease domain, translocation domain, and protease cleavage site are from serotype selected from the group consisting of A, B, C, D, E, F, G, and combinations thereof. Thus, chimeric toxins of BoNT/AB, BoNT/CB, BoNT/DB, BoNT/EB, BoNT/FB, and BoNT/GB are contemplated, wherein the protease domain, translocation domain, and the protease cleavage site are from any of serotype A, C, D, E, F, and G, and the receptor binding domain is from BoNT/B. For example, in some embodiments, the protease domain, translocation domain, and protease cleavage site may be from serotype A. In some embodiments, the modified BoNT polypeptide is a full length BoNT/B. For example, the protease domain, translocation domain, and protease cleavage site may be from serotype B. Such modifications to the BoNT polypeptide enable it to penetrate into lipid membranes and enhances its binding affinity to its target cells (e.g., neurons).

Other aspects of the present disclosure related to methods of making a modified *Clostridial Botulinum* neurotoxin (BoNT), the method comprising making one or more substitution mutation(s) at position corresponding to 1248 or 1249 in serotype B, strain 1 (BoNT/B1). In some embodiments, the substitution mutations correspond to I1248F, I1248Y, I1248H, I1248W, V1249W, V1249F, V1249Y, V1249H, I1248W/V1249F, I1248W/V1249Y, I1248W/V1249H, I1248F/V1249Y, I1248F/V1249H, I1248Y/V1249H, I1248F/V1249W, I1248Y/V1249W, I1248H/V1249W, I1248Y/V1249F, I1248H/V1249F, or I1248H/V1249Y in BoNT/B. In some embodiments, the BoNT polypeptide is BoNT serotype B (BoNT/B). In some embodiments, the BoNT polypeptide is any one of BoNT/B, strains 1-8.

The modified BoNT polypeptides of the present disclosure (e.g., without limitation, polypeptides comprising amino acid sequence of any of SEQ ID NOs: 33-37 and 46-66), will generally be produced by expression form recombinant nucleic acids in appropriate cells (e.g., *E. coli*, or insect cells) and isolated. The nucleic acids encoding the polypeptides described herein may be obtained, and the nucleotide sequence of the nucleic acids determined, by any method known in the art.

Further provided herein are isolated and/or recombinant nucleic acids encoding any of the modified BoNT polypeptides disclosed herein. The nucleic acids encoding the isolated polypeptide fragments of the present disclosure, may be DNA or RNA, double-stranded or single stranded. In certain aspects, the subject nucleic acids encoding the isolated polypeptide fragments are further understood to include nucleic acids encoding polypeptides that are variants of any of the modified BoNT polypeptides described herein.

Variant nucleotide sequences include sequences that differ by one or more nucleotide substitutions, additions or deletions, such as allelic variants. In some embodiments, the isolated nucleic acid molecule of the present disclosure comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity of any of SEQ ID NOs: 33-37 and 46-66. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of any of SEQ ID NOs: 33-37 and 46-66.

In some embodiments, the nucleic acid is comprised within a vector, such as an expression vector. In some embodiments, the vector comprises a promoter operably linked to the nucleic acid.

A variety of promoters can be used for expression of the polypeptides described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter. Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)].

Other systems include FK506 dimer, VP16 or p65 using astradiol, RU486, diphenol murislerone, or rapamycin. Inducible systems are available from Invitrogen, Clontech and Ariad. Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., *Cell,* 49:603-612 (1987)]; Gossen and Bujard (1992); [M. Gossen et al., *Natl. Acad. Sci. USA,* 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89:5547-5551 (1992); Shockett et al., Proc. Natl. Acad. Sci. USA, 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the polypeptides described herein. In some embodiments, the expression of the polypeptides described herein is regulated by a constitutive, an inducible or a tissue-specific promoter.

The host cells used to express the isolated polypeptides described herein may be either bacterial cells such as *Escherichia coli*, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors," Gene 45:101-106; Cockett et al. (1990) "High Level Expression Of Tissue Inhibitor Of Metalloproteinases In Chinese Hamster Ovary Cells Using Glutamine Synthetase Gene Amplification," Biotechnology 8:662-667). A variety of host-expression vector systems may be utilized to express the isolated polypeptides described herein. Such host-expression systems represent vehicles by which the coding sequences of the isolate d polypeptides described herein may be produced and subsequently purified, but also represent cells which may, when transformed or transfected with the appropriate nucleotide coding sequences, express the isolated polypeptides described herein in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the isolated polypeptides described herein; yeast (e.g., *Saccharomyces pichia*) transformed with recombinant yeast expression vectors containing sequences encoding the isolated polypeptides described herein; insect cell systems infected with recombinant virus expression vectors (e.g., baclovirus) containing the sequences encoding the isolated polypeptides described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the isolated polypeptides described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the polypeptides being expressed. For example, when a large quantity of such a protein is to be produced, for the generation of pharmaceutical compositions of polypeptides described herein, vectors which direct the expression of high levels of fusion protein products that are readily purified may be desirable. Such vectors include, but are not limited, to the *E. coli* expression vector pUR278 (Riither et al. (1983) "Easy Identification Of cDNA Clones," EMBO J. 2:1791-1794), in which the coding sequence may be ligated individually into the vector in frame with the lac Z coding region so that a fusion protein is produced; pIN vectors (Inouye et al. (1985) "Up-Promoter Mutations In The lpp Gene Of *Escherichia Coli*," Nucleic Acids Res. 13:3101-3110; Van Heeke et al. (1989) "Expression Of Human Asparagine Synthetase In *Escherichia Coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione.

The pGEX vectors are designed to include thrombin or factor Xa protease cleavage sites so that the cloned target gene product can be released from the GST moiety. In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic.

The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544). In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. For example, in certain embodiments, the polypeptides described herein may be expressed as a single gene product (e.g., as a single polypeptide chain, i.e., as a polyprotein precursor), requiring proteolytic cleavage by native or recombinant cellular mechanisms to form separate polypeptides described herein.

The disclosure thus encompasses engineering a nucleic acid sequence to encode a polyprotein precursor molecule comprising the polypeptides described herein, which includes coding sequences capable of directing post translational cleavage of said polyprotein precursor. Post-translational cleavage of the polyprotein precursor results in the polypeptides described herein. The post translational cleavage of the precursor molecule comprising the polypeptides described herein may occur in vivo (i.e., within the host cell by native or recombinant cell systems/mechanisms, e.g. furin cleavage at an appropriate site) or may occur in vitro (e.g. incubation of said polypeptide chain in a composition comprising proteases or peptidases of known activity and/or in a composition comprising conditions or reagents known to foster the desired proteolytic action).

Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli*," Proc. Nat. Acad. Sci. USA 82:7252-7255, and reviewed in Jenny et al. (2003) "A Critical Review Of The Methods For Cleavage Of Fusion Proteins With Thrombin And Factor Xa," Protein Expr. Purif. 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," Biotechnology 13:982-987 hereby incorporated by reference herein in its entirety)), furin, and AcTEV (Parks et al. (1994) "Release Of Proteins And Peptides From Fusion Proteins Using A Recombinant Plant Virus Proteinase," Anal. Biochem. 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express polypeptides described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the polypeptides described herein. Such engineered cell lines may be particularly useful in screening and evaluation of polypeptides that interact directly or indirectly with the polypeptides described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," Bioessays 14: 495-500), and adenine phosphoribosyltransferase (Lowy et al. (1980) "Isolation Of Transforming DNA: Cloning The Hamster aprt Gene," *Cell* 22: 817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human Gene Therapy," Ann. Rev. Biochem. 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," J. Mol. Biol. 150:1-14.

The expression levels of polypeptides described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a polypeptide described herein is amplifiable, increase in the level of inhibitor present in culture of host cell will increase the number of copies of the marker gene. Since the amplified region is associated with the nucleotide sequence of a polypeptide described herein or a polypeptide described herein, production of the polypeptide will also increase (Crouse et al. (1983) "Expression And Amplification Of Engineered Mouse Dihydrofolate Reductase Minigenes," Mol. Cell. Biol. 3:257-266).

Once a polypeptide described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the polypeptide comprises an Fc domain (or portion thereof)), and sizing column chromatography), centrifugation, differential solubility, or by any other standard technique for the purification of polypeptides or antibodies. Other aspects of the present disclosure relate to a cell comprising a nucleic acid described herein or a vector described herein.

The cell may be a prokaryotic or eukaryotic cell. In some embodiments, the cell in a mammalian cell. Exemplary cell types are described herein. Other aspects of the present disclosure related to a cell expressing the modified BoNT polypeptides described herein. The cell may be a prokaryotic or eukaryotic cell. In some embodiments, the cell in a mammalian cell. Exemplary cell types are described herein. The cell can be for propagation of the nucleic acid or for expression of the nucleic acid, or both. Such cells include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, 4.sup.th ed. 2000); ANIMAL CELL CULTURE: A PRACTICAL APPROACH (John R. W. Masters ed., Oxford University Press, 3.sup.rd ed. 2000); MOLECULAR CLONING A LABORATORY MANUAL, supra, (2001); BASIC CELL CULTURE: A PRACTICAL APPROACH (John M. Davis, Oxford Press, 2.sup.nd ed. 2002); and CURRENT PROTOCOLS IN MOLECULAR BIOLOGY, supra, (2004).

These protocols are routine procedures within the scope of one skilled in the art and from the teaching herein. Yet other aspects of the present disclosure relate to a method of producing a polypeptide described herein, the method comprising obtaining a cell described herein and expressing nucleic acid described herein in said cell. In some embodiments, the method further comprises isolating and purifying a polypeptide described herein.

In some embodiments, botulinum neurotoxin can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive.

The bacterial strains that make botulinum toxin serotypes A and G possess endogenous proteases and serotypes A and G can therefore be recovered from bacterial cultures in predominantly their active form. In contrast, botulinum toxin serotypes Ci, D and E are synthesized by non-proteolytic strains and are therefore typically unactivated when recovered from culture. Serotypes B and F are produced by both proteolytic and non-proteolytic strains and therefore can be recovered in either the active or inactive form. The proteolytic strains that produce, for example, the botulinum toxin type B serotype may only cleave a portion of the toxin produced.

The exact proportion of nicked to un-nicked molecules depends on the length of incubation and the temperature of the culture. Therefore, a certain percentage of a preparation of, for example, the botulinum toxin type B toxin may be inactive. In one embodiment, the neurotoxin of the present disclosure is in an active state. In one embodiment, the neurotoxin is in an inactive state. In one embodiment, a combination of active and inactive neurotoxin is envisioned.

It is also envisioned that the modified receptor binding domain of BoNT/B described here can be utilized as a delivery tool to target neurons in humans. For example, the modified receptor binding domain of BoNT/B can be linked to other therapeutic agents, covalently or non-covalently, and acts as the targeting vehicle to deliver the therapeutic agents to neurons in humans.

As such, another aspect of the disclosure relates to a chimeric polypeptide molecule comprising a first portion that is a modified receptor binding domain of *C. Botulinum* serotype B, comprising one or more substitution mutation(s) which leads to significantly enhanced binding to neurons, linked to a second portion. The second portion of the molecule can be a bioactive molecule such as a therapeutic agent (e.g., a polypeptide or drug). Linkage of the first and second portions of the molecule can be covalent (e.g., in the form of a fusion protein) or non-covalent. Methods of such linkage are known in the art and can readily be applied by the skilled practitioner. When the second portion of the chimeric molecule is a polypeptide and the chimeric molecule is in the form of a protein, nucleic acids and nucleic acid vectors encoding such chimeric molecules are provided.

Also provided are cells comprising the nucleic acids or nucleic acid vectors, and cells expressing such chimeric molecules. The chimeric molecules in a fusion protein form may be expressed and isolated using the methods disclosed herein.

The modified BoNT polypeptides of the present disclosure, has a loop in the receptor binding domain that mediates penetration into lipid membranes and enhancing binding of the BoNT to its target cells. In some embodiments, the target cell is located in a nerve terminal. Thus, the binding of the modified BoNT polypeptides to the nerve terminal is enhanced, compared to a corresponding wild-type BoNT. In some embodiments, such enhanced binding is also specific to a presynaptic nerve terminal. In some embodiments, the presynaptic nerve terminal is in a mammal. In some embodiments, the presynaptic nerve terminal is in a rodent. In some embodiments, the presynaptic nerve terminal is a human presynaptic nerve terminal.

A modified BoNT polypeptide that has enhanced binding affinity to its target cells (e.g., neurons) affords potential for therapeutic use. For example, such modified BoNT polypeptide may be effective at a lower dose. A lower BoNT dose for therapeutic use is generally desirable because less toxin will diffuse to surrounding tissues at the injection site and less neutralizing antibodies may be generated against the BoNT.

Thus, the present disclosure also contemplates pharmaceutically compositions comprising the modified BoNTs or the chimeric molecules of the present disclosure. As it may also become clear later in the present disclosure, the pharmaceutical composition of the present disclosure, may further comprise other therapeutic agents suitable for the specific disease such composition is designed to treat. In some embodiments, the pharmaceutically composition of the present disclosure further comprises pharmaceutically-acceptable carriers.

The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the polypeptide from one site (e.g., the delivery site) of the body, to another site (e.g., organ, tissue or portion of the body).

A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethylcellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, a modified BoNT polypeptide of the present disclosure in a composition is administered by injection, by means of a catheter, by means of a suppository, or by means of an implant, the implant being of a porous, non-porous, or gelatinous material, including a membrane, such as a sialastic membrane, or a fiber.

Typically, when administering the composition, materials to which the polypeptide of the disclosure does not absorb are used. In other embodiments, the modified BoNT polypeptides of the present disclosure are delivered in a controlled release system. Such compositions and methods for administration are provides in U.S. Patent publication No. 2007/0020295, the contents of which are herein incorporated by reference. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

The modified BoNT polypeptides of the present disclosure can be administered as pharmaceutical compositions comprising a therapeutically effective amount of a binding agent and one or more pharmaceutically compatible ingredients. In typical embodiments, the pharmaceutical composition is formulated in accordance with routine procedures as a pharmaceutical composition adapted for intravenous or subcutaneous administration to a subject, e.g., a human being.

Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration. A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated. The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein.

The polypeptides of the present disclosure can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757. The pharmaceutical compositions of the present disclosure may be administered or packaged as a unit dose, for example.

The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle. In some embodiments, the modified BoNT polypeptides described herein may be conjugated to a therapeutic moiety, e.g., an antibiotic. Techniques for conjugating such therapeutic moieties to polypeptides, including e.g., Fc domains, are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al. (1982) "The Preparation And Cytotoxic Properties Of Antibody-Toxin Conjugates," Immunol. Rev., 62:119-158. Further, the pharmaceutical composition can be provided as a pharmaceutical kit comprising (a) a container containing a polypeptide of the disclosure in lyophilized form and (b) a second container containing a pharmaceutically acceptable diluent (e.g., sterile water) for injection. The pharmaceutically acceptable diluent can be used for reconstitution or dilution of the lyophilized polypeptide of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration. In another aspect, an article of manufacture containing materials useful for the treatment of the diseases described above is included. In some embodiments, the article of manufacture comprises a container and a label.

Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is an isolated polypeptide of the disclosure. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

The modified BoNT polypeptides, the chimeric molecules, and the pharmaceutical compositions of the present disclosure may be used for the treatment of conditions associated with unwanted neuronal activities. Thus, further provided herein are methods of treating a condition associated with unwanted neuronal activity, the method comprising administering a therapeutically effective amount of the modified BoNT polypeptide, the chimeric molecule, or the pharmaceutical composition described herein to thereby treat the condition. In some embodiments, the modified BoNT polypeptides, the chimeric molecules, and the pharmaceutic compositions of the present disclosure contact one or more neuron(s) exhibiting unwanted neuronal activity, Condition typically treated with a neurotoxin (e.g., skeletal muscle conditions, smooth muscle conditions, glandular conditions, a neuromuscular disorder, an autonomic disorder, pain, or an aesthetic/cosmetic condition) are associated with unwanted neuronal activity, as determined by the skilled practitioner. Administration is by a route that contacts an effective amount of the composition to neurons exhibiting the unwanted activity. In some embodiments, the condition may be associated with overactive neurons or glands. Specific conditions envisioned for treatment by the methods discussed herein include, without limitation, spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions as well as other secretory disorders, pain from muscle spasms, headache pain. In addition, the present disclosure can be used to treat dermato logical or aesthetic/cosmetic conditions, for example, reduction of brow furrows, reduction of skin wrinkles.

The present disclosure can also be used in the treatment of sports injuries. Borodic U.S. Pat. No. 5,053,005 discloses methods for treating juvenile spinal curvature, i.e. scoliosis, using botulinum type A. The disclosure of Borodic is incorporated in its entirety herein by reference. In one embodiment, using substantially similar methods as disclosed by Borodic, a modified neurotoxin can be administered to a mammal, preferably a human, to treat spinal curvature. In a suitable embodiment, a modified neurotoxin comprising botulinum type E fused with a leucine-based motif is administered. Even more preferably, a modified neurotoxin comprising botulinum type A-E with a leucine-based motif fused to the carboxyl terminal of its light chain is administered to the mammal, preferably a human, to treat spinal curvature.

In addition, the modified neurotoxin can be administered to treat other neuromuscular disorders using well known techniques that are commonly performed with botulinum type A. For example, the present disclosure can be used to treat pain, for example, headache pain, pain from muscle spasms and various forms of inflammatory pain. For example, Aoki U.S. Pat. No. 5,721,215 and Aoki U.S. Pat. No. 6,113,915 disclose methods of using botulinum toxin type A for treating pain. The disclosure of these two patents is incorporated in its entirety herein by reference.

Autonomic nervous system disorders can also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. disclose methods for treating the autonomic nervous system; for example, treating autonomic nervous system disorders such as excessive sweating, excessive salivation, asthma, etc., using naturally existing botulinum toxins. The disclosure of Sander et al. is incorporated in its entirety by reference herein.

In one embodiment, substantially similar methods to that of Sanders et al. can be employed, but using a modified neurotoxin, to treat autonomic nervous system disorders such as the ones discussed above. For example, a modified neurotoxin can be locally applied to the nasal cavity of the mammal in an amount sufficient to degenerate cholinergic neurons of the autonomic nervous system that control the mucous secretion in the nasal cavity. Pain that can be treated by a modified neurotoxin includes pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy can be treated with a naturally occurring botulinum toxin, for example Botulinum type A. The disclosures of Binder are incorporated in its entirety herein by reference.

In one embodiment, substantially similar methods to that of Binder can be employed, but using a modified neurotoxin, to treat headache, especially the ones caused by vascular disturbances, muscular tension, neuralgia and neuropathy. Pain caused by muscle spasm can also be treated by an administration of a modified neurotoxin. For example, a botulinum type E fused with a leucine-based motif, preferably at the carboxyl terminal of the botulinum type E light chain, can be administered intramuscularly at the pain/spasm location to alleviate pain. Furthermore, a modified neurotoxin can be administered to a mammal to treat pain that is not associated with a muscular disorder, such as spasm.

In one broad embodiment, methods of the present disclosure to treat non-spasm related pain include central administration or peripheral administration of the modified neurotoxin. For example, Foster et al. in U.S. Pat. No. 5,989,545 discloses that a botulinum toxin conjugated with a targeting moiety can be administered centrally (intrathecally) to alleviate pain. The disclosures of Foster et al. are incorporated in its entirety by reference herein.

In one embodiment, substantially similar methods to that of Foster et al. can be employed, but using the compositions described herein to treat pain. The pain to be treated can be an acute pain or chronic pain. An acute or chronic pain that is not associated with a muscle spasm can also be alleviated with a local, peripheral administration of the modified neurotoxin to an actual or a perceived pain location on the mammal.

In one embodiment, the modified neurotoxin is administered subcutaneously at or near the location of pain, for example, at or near a cut. In some embodiments, the modified neurotoxin is administered intramuscularly at or near the location of pain, for example, at or near a bruise location on the mammal. In some embodiments, the modified BoNT polypeptide is injected directly into a joint of a mammal, for treating or alleviating pain caused by arthritic conditions. Also, frequent repeated injection or infusion of the modified neurotoxin to a peripheral pain location is within the scope of the present disclosure. Routes of administration for such methods are known in the art and easily adapted to the methods described herein by the skilled practitioner (e.g., see for example, Harrison's Principles of Internal Medicine (1998), edited by Anthony Fauci et al., 14.sup.th edition, published by McGraw Hill).

By way of non-limiting example, the treatment of a neuromuscular disorder can comprise a step of locally administering an effective amount of the molecule to a muscle or a group of muscles, the treatment of an autonomic disorder can comprise a step of locally administering an effective of the molecule to a gland or glands, and the treatment of pain can comprise a step of administering an effective amount of the molecule the site of the pain. In addition, the treatment of pain can comprise a step of administering an effective amount of a modified neurotoxin to the spinal cord.

"A therapeutically effective amount" as used herein refers to the amount of each therapeutic agent of the present disclosure required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons. Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system.

Frequency of administration may be determined and adjusted over the course of therapy, and is generally, but not necessarily, based on treatment and/or suppression and/or amelioration and/or delay of a disease. Alternatively, sustained continuous release formulations of a polypeptide may be appropriate. Various formulations and devices for achieving sustained release are known in the art. In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays.

The dosing regimen (including the polypeptide used) can vary over time. In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the polypeptide (such as the half-life of the polypeptide, and other considerations well known in the art).

For the purpose of the present disclosure, the appropriate dosage of a therapeutic agent as described herein will depend on the specific agent (or compositions thereof) employed, the formulation and route of administration, the type and severity of the disease, whether the polypeptide is administered for preventive or therapeutic purposes, previous therapy, the subject's clinical history and response to the antagonist, and the discretion of the attending physician. Typically the clinician will administer a polypeptide until a dosage is reached that achieves the desired result.

Administration of one or more polypeptides can be continuous or intermittent, depending, for example, upon the recipient's physiological condition, whether the purpose of the administration is therapeutic or prophylactic, and other factors known to skilled practitioners. The administration of a polypeptide may be essentially continuous over a preselected period of time or may be in a series of spaced dose, e.g., either before, during, or after developing a disease. As used herein, the term "treating" refers to the application or administration of a polypeptide or composition including the polypeptide to a subject in need thereof.

"A subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease. In some embodiments, the subject has CDI. In some embodiments, the subject has cancer. In some embodiments, the subject is a mammal. In some embodiments, the subject is a non-human primate. In some embodiments, the subject is human. Alleviating a disease includes delaying the development or progression of the disease, or reducing disease severity. Alleviating the disease does not necessarily require curative results.

As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset.

As used herein "onset" or "occurrence" of a disease includes initial onset and/or recurrence. Conventional methods, known to those of ordinary skill in the art of medicine, can be used to administer the isolated polypeptide or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir.

The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

As used herein, a "subject" refers to a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human.

The terms, "patient" and "subject" are used interchangeably herein. A subject can be male or female. A subject can be a fully developed subject (e.g., an adult) or a subject undergoing the developmental process (e.g., a child, infant or fetus). Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with unwanted neuronal activity. In addition, the methods and compositions described herein can be used to treat domesticated animals and/or pets.

The following examples are intended to be illustrative of certain embodiments and are non-limiting. The entire contents of all of the references (including literature references, issued patents, published patent applications, and co pending patent applications) cited throughout this application are hereby expressly incorporated by reference.

EXAMPLES

Engineered BoNT/B Receptor Binding Domain

It was recently reported that BoNT/B has greatly diminished binding affinity toward human Syt II (h-Syt II) due to a single amino acid change from rodent (rat/mouse) Syt II within the toxin binding site[13,23]. This is a conservative change from phenylalanine (F) to leucine (L) at the position 54. Humans remain sensitive to BoNT/B, as human Syt I (h-Syt I) still contains phenylalanine at this position. However, Syt II appears to be the dominant isoform expressed in motor nerve terminals in mice and the rodent Syt II also has ~10-fold higher binding affinity to BoNT/B than Syt I[24,25].

Thus, BoNT/B might be less efficient in targeting motor neurons in humans than in rodents. It has been a long-standing clinical observation that BoNT/B has to be used at ~60-100 fold higher doses than BoNT/A in order to achieve the same level of effects in patients[26,27]. As the potency of both toxins is measured using mouse models, humans are indeed less sensitive to BoNT/B than mice. Accordingly, restoring high-affinity binding of BoNT/B to h-Syt II may increase its efficacy and specificity for targeting human neurons, reduce the dose in therapeutic applications, and lower the occurrence of detrimental adverse effects for this major therapeutic toxin[28]. A series of mutations in BoNT/B receptor binding domain (BoNT/B-$H_C$) such as E1191M/S1199Y that significantly enhanced binding of BoNT/B to human Syt II were recently discovered (WO 2013180799).

Furthermore, toxin diffusion and generation of neutralization antibodies are not limited to BoNT/B, but also observed for BoNT/A, indicating that the binding affinity of BoNT/A to its receptor SV2 also needs to be improved. Because BoNT/B binding to Syt I/II has much higher affinity than BoNT/A binding to SV2[18,24,29,30], a modified BoNT/B receptor binding domain (BoNT/B-$H_C$) with the ability to bind human Syt II can also be used to replace BoNT/A-$H_C$ to generate a modified chimeric BoNT/A with enhanced efficacy and specificity for human neurons than WT BoNT/A.

The Lipid Binding Loop in BoNT/DC

By utilizing both protein and ganglioside receptors, BoNTs gain the ability to target neurons with extremely high efficacy and specificity. Our interests in this question stemmed from the observation that one botulinum neurotoxin, BoNT/DC, showed the highest potency in mice ($1.1\times10^9$ $LD_{50}$/mg, which is roughly 5-30 fold more than any other BoNTs)[31], so further enhancement of the binding between BoNTs and neurons was investigated. BoNT/DC was found to share Syt I/II as its receptor and also requires gangliosides as co-receptor, similar to other BoNTs[13]. So there might be other reasons why BoNT/DC becomes so potent.

The crystal structure of BoNT/DC revealed an extended loop in the receptor binding domain (FIG. 2A)[32]. This loop contains many hydrophobic residues and has been previously proposed as ganglioside binding loop (GBL), as mutations within this loop abolishes binding of BoNT/DC-$H_C$ to immobilized gangliosides[33,34]. However, recent studies revealed that this loop is not directly involved in ganglioside binding. Instead, this loop contributes to ganglioside binding via non-specific penetration into hydrophobic lipid membranes. Indeed, a point mutation at a tip residue, F1253A, was found to abolish BoNT/DC-$H_C$ binding to ganglioside-free liposomes, suggesting that the tip of this loop penetrates into lipid membranes. This action provides an additional anchor to neuronal membranes, which greatly facilitates binding of BoNT/DC to gangliosides and Syt I/II in a synergistic manner, therefore enhancing the overall binding of BoNT/DC to neurons.

The crystal structure of BoNT/B revealed that it has an extended loop similar to the one found in BoNT/DC (FIG. 2B)[15]. It is also located in an ideal position for penetrating into membranes when BoNT/B binds to gangliosides and Syt I/II. The major difference between the loop in BoNT/B and the loop in BoNT/DC is that their exposed residues at the tip of the loop are different: BoNT/B contains I1248/V1249, while BoNT/DC contains W1252/F1253. Both W and F are typical hydrophobic residues with strong tendency of penetrating into lipid membranes, while I and V are less likely to interact with membranes. Replacing I1248/V1249 with W or F residues may create a loop in BoNT/B that can penetrate into membranes, just like the one in BoNT/DC.

Figure 3A:
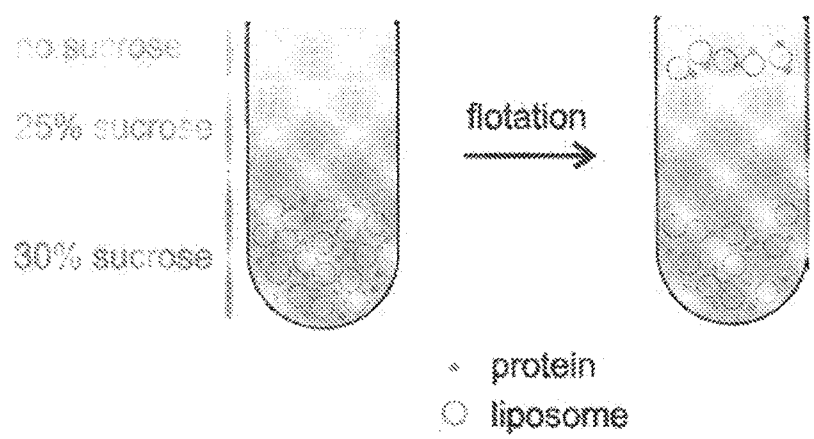
FIGS. 3A-3B show that I1248W and V1249W mutations in BoNT/B-$H_C$ enhanced toxin binding to liposomes, and the enhancement is synergistic with ganglioside-binding.
Figure 3B:
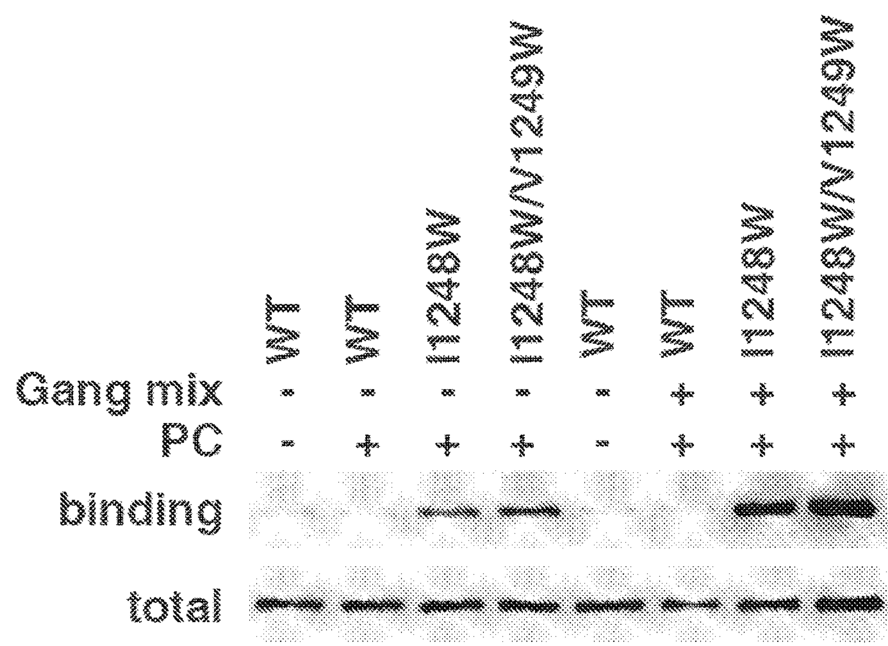

To test this hypothesis, both a single mutation: BoNT/B-$H_C$ (I1248W) and a double mutation BoNT/B-$H_C$ (I1248W/V1249W) were created. Binding of these mutants to artificial liposomes was examined using a well-established liposome floatation assay (FIG. 3A). The assay was carried out by first incubating BoNT/B-$H_C$ with liposomes containing either phosphatidylcholine (PC) alone or PC plus gangliosides (1%). The mixture was then subjected to centrifugation in a sucrose gradient. Liposomes will float to the top of the gradient due to its low density. Proteins that bound to the liposomes will float to the top together with liposomes, whereas proteins that do not bind to liposomes will stay at the bottom of the centrifuge tube (FIG. 3A). Bound proteins were than detected via immunoblotting analysis. As shown in FIG. 3B, BoNT/B-$H_C$ (I1248W) and BoNT/B-$H_C$ (I1248W/V1249W) gained the ability to bind PC liposomes, while WT BoNT/B-$H_C$ did not bind to liposomes. BoNT/B-$H_C$ (I1248W/V1249W) showed a further increased binding to liposomes compared to BoNT/B (I1248W). Adding gangliosides to liposomes did not enhance binding of WT BoNT/B-$H_C$, as the interactions between WT BoNT/B-$H_C$ and gangliosides are relatively weak. In contrast, BoNT/B-$H_C$ (I1248W) and BoNT/B-$H_C$ (I1248W/V1249W) showed strong binding to ganglioside-containing liposomes, higher than their binding to ganglioside-free liposomes (FIG. 3B). Together, these results not only demonstrate that BoNT/B-$H_C$ (I1248W) and BoNT/B-$H_C$ (I1248W/V1249W) gain the ability to bind lipid membranes, but also showed that their interactions with lipids can be synergistic with ganglioside-binding, resulting in a greatly elevated overall binding affinity toward ganglioside-containing membranes.

Figure 4A:
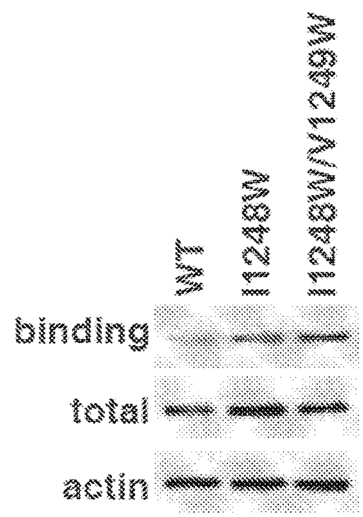
FIGS. 4A-4B show that I1248W and V1249W mutations in BoNT/B-$H_C$ enhanced toxin binding to neurons.
Figure 4B:
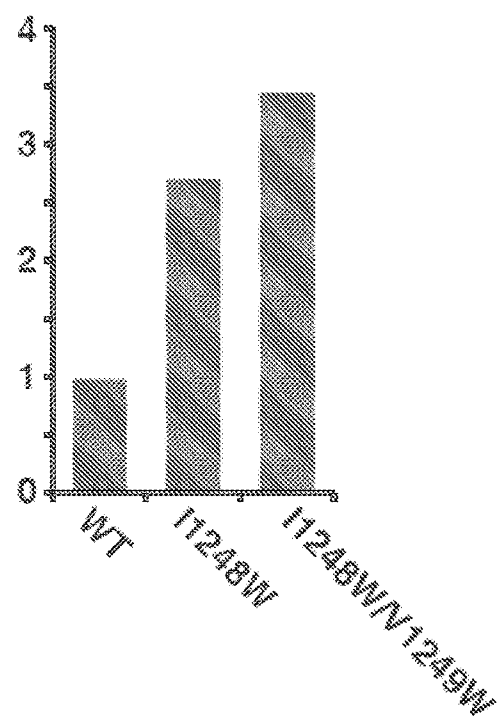

These findings were next validated on physiologically relevant neuronal surfaces. Cultured rat cortical neurons were exposed to WT, I1248W or I1248W/V1249W BoNT/B-$H_C$. Binding of BoNT/B-$H_C$ was detected by immunoblotting analysis of cell lysates, which provided a way to quantify the level of binding, As shown in FIG. 4, I1248W and I1248W/V1249W BoNT/B-$H_C$ showed significantly higher binding to neurons than WT BoNT/B-$H_C$, approximately 2.7- and 3.5-fold more than WT, respectively.

Figure 5:
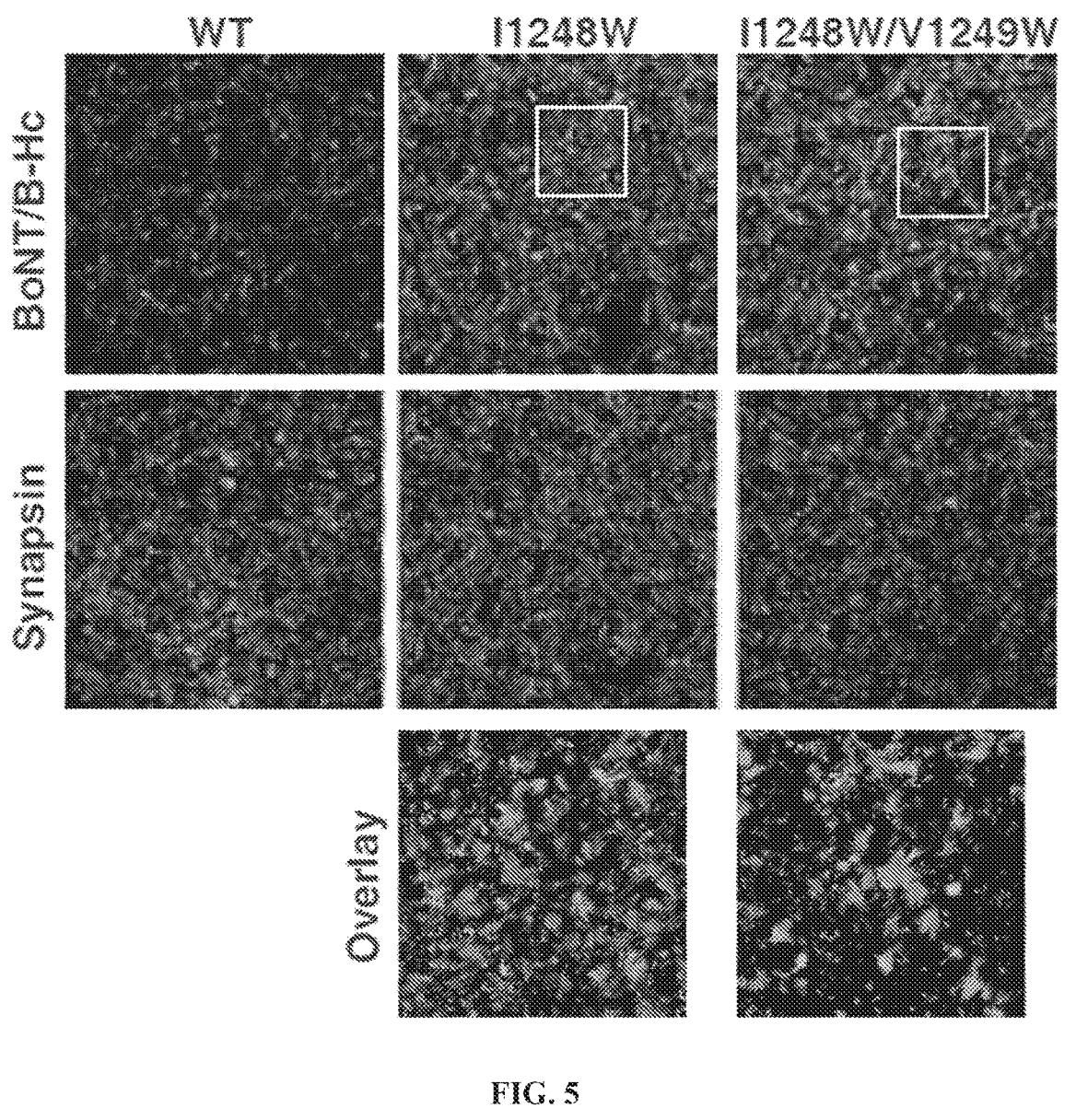

The binding of WT, I1248W or I1248W/V1249W BoNT/B-$H_C$ to neurons was further examined via immunostaining analysis, to determine whether the toxin binding is specifically localized to presynaptic nerve terminals. As shown in FIG. 5, I1248W and I1248W/V1249W BoNT/B-$H_C$ showed drastically higher binding to neurons than WT BoNT/B-$H_C$. Importantly, binding of I1248W and I1248W/V1249W BoNT/B-$H_C$ co-localizes with presynaptic nerve terminal marker synapsin, indicating that enhanced binding is specific to presynaptic nerve terminals.

Together, these results demonstrate that changing residues I1248 to W and V1249 to W created a functional loop as the "third anchor" in BoNT/B-$H_C$, which drastically enhanced binding to nerve terminals. Similarly, changing I1248/V1249 with other typical membrane-interacting residues such as F, Y, and H may also create a functional loop in BoNT/B that can penetrate into membranes and enhance binding of BoNT/B to neuronal membranes.

Therefore, replacing I1248 and V1249 with residues W, F, Y, or H creates novel engineered BoNT/B with significantly enhanced binding to nerve terminals. These mutations can be used to create a new generation of BoNT/B with greater efficacy than the natural BoNT/B. The receptor binding domain of BoNT/B containing these mutations can also be utilized to create chimeric toxins, such as BoNT/AB, with potentially greater efficacy than the natural BoNT/A.

Materials and Methods Antibodies and Materials:

The following antibodies were purchased from indicated vendors: mouse monoclonal anti-HA (16B12, Covance), rabbit polyclonal anti-synapsin (Millipore). Bovine mixed brain gangliosides were purchased from Matreya LLC (Pleasant Gap, Pa.) and were reconstituted in Tris-buffered saline (TBS: 20 mM Tris, 150 mM NaCl) as previously described 9.). PC lipids were purchased from Avanti (Alabaster, Ala.). cDNA and constructs: DNA encoding BoNT/B-$H_C$ (residue 856-1291, based on GenBank access No:AB232927) was synthesized by Geneart Inc. and its codon has been optimized for expression in *E. Coli*. DNA encoding BoNT/B-$H_C$ was subcloned into pET28a vector, with both a His6 tag and a HA tag (YPYDVPDYA (SEQ ID NO: 1)) fused to its N-terminus. Mutations in BoNT/B-$H_C$ were generated via PCR using Quickchange Site-directed Mutagenesis Kit (Agilent Technologies, CA), following the manufacturer's manual. All constructs were verified by sequencing.

Protein Expression and Purification:

WT and mutants of BoNT/B-$H_C$ were expressed as His6 tagged recombinant proteins in *E. Coli*. $His_6$-fusion proteins were purified as previously described 9, with the induction temperature at 20° C. overnight with 0.25 mM IPTG.

Neuron Culture and Toxin Binding Assays:

Rat cortical neurons were prepared from E18-19 embryos as described previously 9. Toxin binding to cortical neurons was carried out in high $K^+$ buffer (the same as PBS, but adjusted to 56 mM KCl and 87 mM NaCl plus 1 mM $CaCl_2$) for 5 min as previously described 9. Cells were washed and subjected to either immunoblotting analysis or immunostaining analysis. For immunostaining assays, cells were fixed and permeabilized for immunostaining analysis. Fluorescence images were collected using a Leica TCS SP8 confocal microscope with a 40× objective.

Liposome Co Flotation Assays:

PC was dissolved in chloroform. Gangliosides were dissolved in chloroform:methanol (3:1). PC alone or PC mixed with gangliosides (1%) were dried under nitrogen gas. Lipid films were re-hydrated with the lipid reconstitution buffer (30 mM Tris, 150 mM NaCl, 2 mM $MgCl_2$, 2 mM DTT, pH7.5). Re-suspended lipids were mixed using a shaker at room temperature (RT) for 1 hour. Liposomes were generated from re-suspended with an extruder (200 nm pore size, 20 strokes manually, Avanti). Liposomes (75 μl) were incubated with 1 μM proteins in a total volume of 150 μl for 30 min at RT. The liposome protein mixtures were then added to 100 al 75% sucrose solution (in lipid reconstitution buffer) to get 250 μl 30% sucrose solution that were loaded as the bottom layer in the centrifuge tube, followed by 200 μl 25% sucrose, and 50 μl lipid reconstitution buffer, as depicted in FIG. 5A. Loaded sucrose gradients were centrifuged at 240,000 g for 1 hour (Beckman TLS-55 rotor, OptiMax MAX-XP benchtop centrifuge). After the centrifugation, 50 μl solutions were taken from the top of the centrifuge tube, mixed with loading dyes, and subjected to immunoblotting analysis.

TABLE 1

*Clostridial Botulinum* neurotoxin (BoNT) amino acid sequences
*amino acid positions where substitutions occur are underlined

| SEQ ID NO | Description | Sequence |
|---|---|---|
| 1 | Wild-type BoNT/B1, Okra strain | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE<br>KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEWRV<br>YTYKYFKKEEEKLFLAPISDSDEFYNTIQIKEYDEQPTYSCQLLFKKDE<br>ESTDEIGLIGIHRFYESGIVFEEYKDYFCISKWYLKEVKRKPYNLKLGC<br>NWQFIPKDEGWTE |
| 2 | Wild-type BoNT/B2, 111 strain | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKNMEKEYRGQNKAINKQAYEEISKEHLAVYKIQMCKSVRA<br>PGICIDVDNEDLFFIADKNSFSDDLSKNERIEYDTQSNYIENRSSIDELIL<br>DTNLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVDDFVIEANKSSTMDKIADISLIVPYIGLALNVGNETAKGNFEN<br>AFEIAGASILLEFIPELLIPVVGAFLLESYIDNKNKIIKTIDNALTKRDEK<br>WIDMYGLIVAQWLSTVNTQFYTIKEGMYKALNYQAQALEEIIKYKYN<br>IYSEKEKSNINIDFNDINSKLNEGINQAVDNINNFINECSVSYLMKKMIP |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | LAVEKLLDFDNTLKKNLLNYIDENKLYLIGSAEYEKSKVDKHLKTIIPF<br>DLSMYTNNTILIEIFNKYNSEILNNIILNLRYRDNNLIDLSGYGANVEVY<br>DGVELNDKNQFKLTSSTNSEIRVTQNQNIIFNSMFLDFSVSFWIRIPKYK<br>NDGIQNYIHNEYTIINCIKNNSGWKISIRGNRIIWTLTDINGKTKSVFFE<br>YSIREDISDYINRWFFVTITNNSDNAKIYINGKLESNIDIKDIGEVIANGE<br>IIFKLDGDIDRTQFIWMKYFSIFNTELSQSNIKEIYKIQSYSEYLKDFWG<br>NPLMYNKEYYMFNAGNKNSYIKLKKDSSVGEILTRSKYNQNSNYINY<br>RNLYIGEKFIIRRKSNSQSINDDIVRKEDYIYLDFFNSNREWRVYAYKD<br>FKEEEKKLFLANIYDSNEFYKTIQIKEYDEQPTYSCQLLFKKDEESTDEI<br>GLIGIHRFYESGIVLKDYKNYFCISKWYLKEVKRKPYNPNLGCNWQFI<br>PKDEGWIE |
| 3 | Wild-type BoNT/B3, CDC795 strain | MPVTINNFNYNDPIDNDNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPRIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKNMEKEYRGQNKAINKQAYEEISKEHLAVYKIQMCKSVRA<br>PGICIDVDNEDLFFIADKNSFSDDLSKNERIEYDTQSNYIENRSSIDELIL<br>DTNLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVDDFVIEANKSSTMDKIADISLIVPYIGLALNVGNETAKGNFEN<br>AFEIAGASILLEFIPELLIPVVGAFLLESYIDNKNKIIKTIDNALTKRDEK<br>WIDMYGLIVAQWLSTVNTQFYTIKEGMYKALNYQAQALEEIIKYKYN<br>IYSEKEKSNINIDFNDINSKLNEGINQAIDNINNFINECSVSYLMKKMIPL<br>AVEKLLDFDNTLKKNLLNYIDENKLYLIGSAEYEKSKVDKHLKTIIPFD<br>LSMYTNNTILIEIFNKYNSEILNNIILNLRYRDNNLIDLSGYGAKVEVYN<br>GVELNDKNQFKLTSSANSKIRVTQNQDIIFNSMFLDFSVSFWIRIPKYK<br>NDGIQNYIHNEYTIINCIKNNSGWKISIRGNKIIWTLTDINGKTKSVFFE<br>YSIRKDVSEYINRWFFVTITNNSDNAKIYINGKLESNIDIKDIGEVIANG<br>EIIFKLDGDIDRTQFIWMKYFSIFNTELSQSNIKEIYKIQSYSEYLKDFW<br>GNPLMYNKEYYMFNAGNKNSYIKLKKDSSVGEILTRSKYNQNSNYIN<br>YRNLYIGEKFIIRRKSNSQSINDDIVRKEDYIYLDFFNLNQEWRVYAYK<br>DFKKKEEKLFLANIYDSNEFYNTIQIKEYDEQPTYSCQLLFKKDEESTD<br>EIGLIGIHRFYESGIVFKDYKDYFCISKWYLKEVKRKPYNPNLGCNWQ<br>FIPKDEGWIE |
| 4 | Wild-type BoNT/B4, Eklund 17B strain | MPVTINNFNYNDPIDNDNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VEQKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDTIQAEELYTFGGQDPSIISPSTDKSIYDKVLQN<br>FRGIVDRLNKVLVCISDPNININIYKNKFKDKYKFVEDSEGKYSIDVESF<br>NKLYKSLMFGFTEINIAENYKIKTRASYFSDSLPPVKIKNLLDNEIYTIE<br>EGFNISDKNMGKEYRGQNKAINKQAYEEISKEHLAVYKIQMCKSVKV<br>PGICIDVDNENLFFIADKNSFSDDLSKNERVEYNTQNNYIGNDFPINELI<br>LDTDLISKIELPSENTESLTDFNVDVPVYEKQPAIKKVFTDENTIFQYLY<br>SQTFPLNIRDISLTSSFDDALLVSSKVYSFFSMDYIKTANKVVEAGLFA<br>GWVKQIVDDFVIEANKSSTMDKIADISLIVPYIGLALNVGDETAKGNFE<br>SAFEIAGSSILLEFIPELLIPVVGVFLLESYIDNKNKIIKTIDNALTKRVEK<br>WIDMYGLIVAQWLSTVNTQFYTIKEGMYKALNYQAQALEEIIKYKYN<br>IYSEEEKSNININFNDINSKLNDGINQAMDNINDFINECSVSYLMKKMIP<br>LAVKKLLDFDNTLKKNLLNYIDENKLYLIGSVEDEKSKVDKYLKTIIPF<br>DLSTYTNNEILIKIFNKYNSEILNNIILNLRYRDNNLIDLSGYGAKVEVY<br>DGVKLNDKNQFKLTSSADSKIRVTQNQNIIFNSMFLDFSVSFWIRIPKY<br>RNDDIQNYIHNEYTIINCMKNNSGWKISIRGNRIIWTLIDINGKTKSVFF<br>EYNIREDISEYINRWFFVTITNNLDNAKIYINGTLESNMDIKDIGEVIVN<br>GEITFKLDGDVDRTQFIWMKYFSIFNTQLNQSNIKEIYKIQSYSEYLKD<br>FWGNPLMYNKEYYMFNAGNKNSYIKLVKDSSVGEILIRSKYNQNSNY<br>INYRNLYIGEKFIIRRKSNSQSINDDIVRKEDYIHLDFVNSNEEWRVYA<br>YKNFKEQEQKLFLSIIYDSNEFYKTIQIKEYDEQPTYSCQLLFKKDEEST<br>DDIGLIGIHRFYESGVLRKKYKDYFCISKWYLKEVKRKPYKSNLGCN<br>WQFIPKDEGWTE |
| 5 | Wild-type BoNT/B5, CDC795 strain | MPVTINNFNYNDPIDNNNIIMMEPPFARGMGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVN<br>DLPIVPNEKKFFMQSTDAIQAEELYTFGGQDPSIISPSTDKSIYDKVLQN |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKNMEKEYRGQNKAINKQAYEEISKEHLAVYKIQMCKSVKA<br>PGICIDVDNEDLFFIADKNSFSDDLSKNERIAYNTQNNYIENDFSINELIL<br>DTDLISKIELPSENTESLTDFNVYVPVYKKQPAIKKIFTDENTIFQYLYS<br>QTFPLDIRDISLTSSFDDALLFSNKVYSFFSMDYIKTANKVVEAGLFAG<br>WVKQIVDDFVIEANKSSTMDKIADISLIVPYIGLALNVGNETAKGNFEN<br>AFEIAGASILLEFIPELLIPVVGAFLLESYIDNKNKIIETINSALTKRDEK<br>WIDMYGLIVAQWLSTVNTQFYTIKEGMYKALNYQAQALEEIIKYKYN<br>IYSEKERSNINIDFNDVNSKLNEGINQAIDNINNFINECSVSYLMKKMIP<br>LAVEKLLDFDNTLRKNLLNYIDENKLYLIGSAEYEKSKVDKYLKTSIPF<br>DLSTYTNNTILIEIFNKYNSDILNNIILNLRYRDNKLIDLSGYGAKVEVY<br>DGVKLNDKNQFKLTSSANSKIRVIQNQNIIFNSMFLDFSVSFWIRIPKY<br>KNDGIQNYIHNEYTIINCMKNNSGWKISIRGNMIIWTLIDINGKIKSVFF<br>EYSIKEDISEYINRWFFVTITNNSDNAKIYINGKLESHIDIRDIREVIAND<br>EIIFKLDGNIDRTQFIWMKYFSIFNTELSQSNIEEIYKIQSYSEYLKDFWG<br>NPLMYNKEYYMFNAGNKNSYIKLKKDSSVGEILTRSKYNQNSKYINY<br>RDLYIGEKFIIRRKSNSQSINDDIVRKEDYIYLDFFNLNQEWRVYMYKY<br>FKKEEEKLFLAPISDSDEFYNTIQIKEYDEQPTYSCQLLFKKDEESTDEI<br>GLIGIHRFYESGIVFKEYKDYFCISKWYLKEVKRKPYNSKLGCNWQFIP<br>KDEGWTE |
| 6 | Wild-type BoNT/B6, Osaka05 strain | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKNMEKEYRGQNKAINKQAYEEISKEHLAVYKIQMCKSVRA<br>PGICIDVDNEDLFFIADKNSFSDDLSKNERIEYDTQSNYIENRSSIDELIL<br>DTNLISKIELPSENTESLTDFNVDVPVYEKQPAIKKFFTDENTIFQYLYS<br>QTFPLDIRDISLTSSFDDALLFSNKVYSFFSMDYIKTANKVVEAGLFAG<br>WVKQIVDDFVIEANKSNTMDKLADISLIVPYIGLALNVGNETAKGNFE<br>NAFEIAGASILLEFIPELLIPVVGAFLLESYIDNKNKIIKTIDNALTKRDE<br>KWRDMYGLIVAQWLSTVNTQFYTIKEGMYKALNYQAQALEEIIKYK<br>YNIYSEKEKSNINIDFNDINSKLNEGINQAIDNINNFINECSVSYLMKKM<br>IPLAVEKLLDFDNTLKKNLLNYIDENKLYLIGSAEYEKSKVDKHLKTII<br>PFDLSMYTNNTILIEIFKKYNSEILNNIILNLRYRDNNLIDLSGYGANVE<br>VYDGVELNDKNQFKLTSSTNSEIRVTQNQNIIFNSMFLDFSVSFWIRIPK<br>YKNDGIQNYIHNEYTIINCIKNNSGWKISIRGNRIIWTLTDINGKTKSVF<br>FEYSIREDISDYINRWFFVTITNNSDNAKIYINGKLESNIDIKDIGEVIAN<br>GEIIFKLDGDIDRTQFIWMKYFSIFNTELSQSNIKEIYKIQSYSEYLKDF<br>WGNPLMYNKEYYMFNAGNKNSYIKLKKDSPVGEILTRSKYNQNSNYI<br>NYRNLYIGEKFIIRRKSNSQSINDDIVRKEDYIYLDFFNLNQEWRVYAL<br>KNFKKKEEKLFLAPISDSDEFYNTIQIKEYDEQPTYSCQLLFKKDEEST<br>DEIGLIGIHRFYESGIVFKDYKYYFCISKWYLKEVKRKPYNPNLGCNW<br>QFIPKDEGWIE |
| 7 | Wild-type BoNT/B7, Bac-04-07755 strain | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTKNIYIENYFSINELIL<br>DTDLISGIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIIDDFVIEANKSSTMDKIADISLIVPYIGLALNVGNETAKGNFEN<br>AFEIAGASILLEFIPELLIPVVGAFLLESYIDNKNKIIKTIDNALTKRVEK<br>WIDMYGLIVAQWLSTVNTQFYTIKEGMYKALNYQAQALEEIIKYKYN<br>IYSEKEKLNINIDFNDINSKLNEGINQAIDNINNFINECSVSYLMKKMIPL<br>AIEKLLDFDNALKKNLLNYIDENKLYLIGSVEEEKSKVDKFFKTIIPFDL<br>SMYTNNTILIEMVNKYNSEILNNIILNLRYRDNNLIDSSGYGAKVEVYN<br>GVELNDKNQFKLTSSANSKIKVTQNQNITFNSMFLDFSVSFWIRIPKYK<br>NDGIQNYIHNEYTIINCMKNNSGWKISIRGNRIIWTLTDINGKTKSVFFE<br>YSIREDISDYINRWFFVTITNNLDNAKIYINGKLESNIDIRDIREVIVNGEI<br>IFKLDGEIDRTQFIWMKYFSIFNTELSQSNVKEIYKIQSYSKYLKDFWG<br>NPLMYNKEYYMFNAGNKNSYIKLVKDSSVGEILTRSKYNQNSNYINY<br>RNLYIGEKFIIRRKSSSQSISDDIVRKEDYIYLDFFNSNREWRVYAYKNF |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | KGQEEKLFLANIYDSNEFYKTIQIKEYDEQPTYSCQLLFKKDEESTDEI<br>GLIGIHNFYESGILFKDYKDYFCISKWYLKEVKKKPYSSNLGCNWQFIP<br>KDEGWTE |
| 8 | Wild-type BoNT/B8, Maehongson strain | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGG<br>EERKEGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNGKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDDEIYTIE<br>EGFNISDKNMGKEYRGQNKAINKQAYEEISKEHLAVYKIQMCKSVRA<br>PGICIDVDNEDLFFIADKNSFSDDLSKNERIEYNTQSNYIENDFSINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVDDFVIEANKSNTMDKIADISLIVPYIGLALNVGNETAKGNFE<br>NAFEIAGSSILLEFIPELLIPVVGAFLLESYIDNKNKIIKTIDNALTKRDEK<br>WIDMYGLIVAQWLSTVNTQFYTIKEGMYKALNYQAQALEEIIKYKYN<br>IYSEKEKSNISIDFNDINSKLNEGINQAIDNINDFINECSVSYLMKKMIPL<br>AVEKLLDFDNTLKKNLLNYIDENKLYLIGSAEYEKSKVDKHLKTIMTF<br>DLSMYTNNTILIKMVNKYNSEILNNIILNLRYRDNNLIDLSGYGANVEV<br>YDGVELNDKNQFKLTSSTNSEIRVTQNQNIIVNSMFLDFSVSFWIRIPK<br>YKNDGIQNYIHNEYTIINCMKNNSGWKISIRGNRIIWTLIDINGKIKSVF<br>FEYSIRKDVSEYINRWFFVTITNNLDNAKIYINGKLESNMDIRDIREVIA<br>NGEIIFKLDGDIDRTQFIWMKYFSIFNTELSQSNIEEIYKIQSYSEYLKDF<br>WGNPLMYNKEYYMFNAGSKNSYIKLKKDSSVGEILTRSKYNQNSQYI<br>NYRDLYIGEKFIIKRKSNSQSINDDIVRKEDYIYLDFFNLNQEWRVYAY<br>KDFKGQKEQKLFLANIHDSNEFYKTIQIKEYDEQPTYSCQLLFKKDEES<br>TDEIGLIGIHRFYESGFVFQEYKYYFCISKWYLKEVKKKPYNPDLGCN<br>WQFIPKDEGWTE |
| 9 | Wild-type BoNT/B1 receptor binding domain (860-1291) | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY<br>FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEWRVYTYKYFKKEEEKLFLAPISDSDEF<br>YNTIQIKEYDEQPTYSCQLLFKKDEESTDEIGLIGIHRFYESGIVFEEYK<br>DYFCISKWYLKEVKRKPYNLKLGCNWQFIPKDEGWTE |
| 10 | Wild-type BoNT/B2 receptor binding domain (860-1291) | ILNNIILNLRYRDNNLIDLSGYGANVEVYDGVELNDKNQFKLTSSTNSE<br>IRVTQNQNIIFNSMFLDFSVSFWIRIPKYKNDGIQNYIHNEYTIINCIKNN<br>SGWKISIRGNRIIWTLTDINGKTKSVFFEYSIREDISDYINRWFFVTITNN<br>SDNAKIYINGKLESNIDIKDIGEVIANGEIIFKLDGDIDRTQFIWMKYFSI<br>FNTELSQSNIKEIYKIQSYSEYLKDFWGNPLMYNKEYYMFNAGNKNS<br>YIKLKKDSSVGEILTRSKYNQNSNYINYRNLYIGEKFIIRRKSNSQSIND<br>DIVRKEDYIYLDFFNSNREWRVYAYKDFKEEEKKLFLANIYDSNEFYK<br>TIQIKEYDEQPTYSCQLLFKKDEESTDEIGLIGIHRFYESGIVLKDYKNY<br>FCISKWYLKEVKRKPYNPNLGCNWQFIPKDEGWIE |
| 11 | Wild-type BoNT/B3 receptor binding domain (860-1291) | ILNNIILNLRYRDNNLIDLSGYGAKVEVYNGVELNDKNQFKLTSSANS<br>KIRVTQNQDIIFNSMFLDFSVSFWIRIPKYKNDGIQNYIHNEYTIINCIKN<br>NSGWKISIRGNKIIWTLTDINGKTKSVFFEYSIRKDVSEYINRWFFVTIT<br>NNSDNAKIYINGKLESNIDIKDIGEVIANGEIIFKLDGDIDRTQFIWMKY<br>FSIFNTELSQSNIKEIYKIQSYSEYLKDFWGNPLMYNKEYYMFNAGNK<br>NSYIKLKKDSSVGEILTRSKYNQNSNYINYRNLYIGEKFIIRRKSNSQSI<br>NDDIVRKEDYIYLDFFNLNQEWRVYAYKDFKKKEEKLFLANIYDSNE<br>FYNTIQIKEYDEQPTYSCQLLFKKDEESTDEIGLIGIHRFYESGIVFKDY<br>KDYFCISKWYLKEVKRKPYNPNLGCNWQFIPKDEGWIE |
| 12 | Wild-type BoNT/B4 receptor binding domain (860-1291) | ILNNIILNLRYRDNNLIDLSGYGAKVEVYDGVKLNDKNQFKLTSSADS<br>KIRVTQNQNIIFNSMFLDFSVSFWIRIPKYRNDDIQNYIHNEYTIINCMK<br>NNSGWKISIRGNRIIWTLIDINGKTKSVFFEYNIREDISEYINRWFFVTIT<br>NNLDNAKIYINGTLESNMDIKDIGEVIVNGEITFKLDGDVDRTQFIWM<br>KYFSIFNTQLNQSNIKEIYKIQSYSEYLKDFWGNPLMYNKEYYMFNAG<br>NKNSYIKLVKDSSVGEILIRSKYNQNSNYINYRNLYIGEKFIIRRKSNSQ<br>SINDDIVRKEDYIHLDFVNSNEEWRVYAYKNFKEQEQKLFLSIIYDSNE<br>FYKTIQIKEYDEQPTYSCQLLFKKDEESTDDIGLIGIHRFYESGVLRKKY<br>KDYFCISKWYLKEVKRKPYKSNLGCNWQFIPKDEGWTE |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| 13 | Wild-type BoNT/B5 receptor binding domain (860-1291) | ILNNIILNLRYRDNKLIDLSGYGAKVEVYDGVKLNDKNQFKLTSSANS<br>KIRVIQNQNIIFNSMFLDFSVSFWIRIPKYKNDGIQNYIHNEYTIINCMK<br>NNSGWKISIRGNMIIWTLIDINGKIKSVFFEYSIKEDISEYINRWFFVTIT<br>NNSDNAKIYINGKLESHIDIRDIREVIANDEIIFKLDGNIDRTQFIWMKY<br>FSIFNTELSQSNIEEIYKIQSYSEYLKDFWGNPLMYNKEYYMFNAGNK<br>NSYIKLKKDSSVGEILTRSKYNQNSKYINYRDLYIGEKFIIRRKSNSQSI<br>NDDIVRKEDYIYLDFFNLNQEWRVYMYKYFKKEEEKLFLAPISDSDEF<br>YNTIQIKEYDEQPTYSCQLLFKKDEESTDEIGLIGIHRFYESGIVFKEYK<br>DYFCISKWYLKEVKRKPYNSKLGCNWQFIPKDEGWTE |
| 14 | Wild-type BoNT/B6 receptor binding domain (860-1291) | ILNNIILNLRYRDNNLIDLSGYGANVEVYDGVELNDKNQFKLTSSTNSE<br>IRVTQNQNIIFNSMFLDFSVSFWIRIPKYKNDGIQNYIHNEYTIINCIKNN<br>SGWKISIRGNRIIWTLTDINGKTKSVFFEYSIREDISDYINRWFFVTITNN<br>SDNAKIYINGKLESNIDIKDIGEVIANGEIIFKLDGDIDRTQFIWMKYFSI<br>FNTELSQSNIKEIYKIQSYSEYLKDFWGNPLMYNKEYYMFNAGNKNS<br>YIKLKKDSPVGEILTRSKYNQNSNYINYRNLYIGEKFIIRRKSNSQSIND<br>DIVRKEDYIYLDFFNLNQEWRVYALKNFKKKEEKLFLAPISDSDEFYN<br>TIQIKEYDEQPTYSCQLLFKKDEESTDEIGLIGIHRFYESGIVFKDYKYY<br>FCISKWYLKEVKRKPYNPNLGCNWQFIPKDEGWIE |
| 15 | Wild-type BoNT/B7 receptor binding domain (860-1291) | ILNNIILNLRYRDNNLIDSSGYGAKVEVYNGVELNDKNQFKLTSSANS<br>KIKVTQNQNITFNSMFLDFSVSFWIRIPKYKNDGIQNYIHNEYTIINCMK<br>NNSGWKISIRGNRIIWTLTDINGKTKSVFFEYSIREDISDYINRWFFVTIT<br>NNLDNAKIYINGKLESNIDIRDIREVIVNGEIIFKLDGEIDRTQFIWMKY<br>FSIFNTELSQSNVKEIYKIQSYSKYLKDFWGNPLMYNKEYYMFNAGN<br>KNSYIKLVKDSSVGEILTRSKYNQNSNYINYRNLYIGEKFIIRRKSSSQSI<br>SDDIVRKEDYIYLDFFNSNREWRVYAYKNFKGQEEKLFLANIYDSNEF<br>YKTIQIKEYDEQPTYSCQLLFKKDEESTDEIGLIGIHNFYESGILFKDYK<br>DYFCISKWYLKEVKKKPYSSNLGCNWQFIPKDEGWTE |
| 16 | Wild-type BoNT/B8 receptor binding domain (860-1291) | ILNNIILNLRYRDNNLIDLSGYGANVEVYDGVELNDKNQFKLTSSTNSE<br>IRVTQNQNIIVNSMFLDFSVSFWIRIPKYKNDGIQNYIHNEYTIINCMKN<br>NSGWKISIRGNRIIWTLIDINGKIKSVFFEYSIRKDVSEYINRWFFVTITN<br>NLDNAKIYINGKLESNMDIRDIREVIANGEIIFKLDGDIDRTQFIWMKYF<br>SIFNTELSQSNIEEIYKIQSYSEYLKDFWGNPLMYNKEYYMFNAGSKNS<br>YIKLKKDSSVGEILTRSKYNQNSQYINYRDLYIGEKFIIKRKSNSQSIND<br>DIVRKEDYIYLDFFNLNQEWRVYAYKDFKGQKEQKLFLANIHDSNEF<br>YKTIQIKEYDEQPTYSCQLLFKKDEESTDEIGLIGIHRFYESGFVFQEYK<br>YYFCISKWYLKEVKKKPYNPDLGCNWQFIPKDEGWTE |
| 17 | Chimeric toxin BoNT/A1 (1-872)-B1 (860-1291) | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEWRVYTYKYFKKEEEKLFLAPISDSDEFYNTI<br>QIKEYDEQPTYSCQLLFKKDEESTDEIGLIGIHRFYESGIVFEEYKDYFCI<br>SKWYLKEVKRKPYNLKLGCNWQFIPKDEGWTE |
| 18 | Chimeric toxin BoNT/A2 (1-872)-B1 (860-1291) | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHDVLNLTRNGYGSTQYIRFSPDFTFGFE<br>ESLEVDTNPLLGAGKFATDPAVTLAHELIHAEHRLYGIAINPNRVFKV<br>NTNAYYEMSGLEVSFEELRTFGGHDAKFIDSLQENEFRLYYYNKFKD |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | VASTLNKAKSIIGTTASLQYMKNVFKEKYLLSEDTSGKFSVDKLKFDK<br>LYKMLTEIYTEDNFVNFFKVINRKTYLNFDKAVFRINIVPDENYTIKDG<br>FNLKGANLSTNFNGQNTEINSRNFTRLKNFTGLFEFYKLLCVRGIIPFK<br>TKSLDEGYNKALNDLCIKVNNWDLFFSPSEDNFTNDLDKVEEITADTN<br>IEAAEENISLDLIQQYYLTFDFDNEPENISIENLSSDIIGQLEPMPNIERFP<br>NGKKYELDKYTMFHYLRAQEFEHGDSRIILTNSAEEALLKPNVAYTFF<br>SSKYVKKINKAVEAFMFLNWAEELVYDFTDETNEVTTMDKIADITIIV<br>PYIGPALNIGNMLSKGEFVEAIIFTGVVAMLEFIPEYALPVFGTFAIVSYI<br>ANKVLTVQTINNALSKRNEKWDEVYKYTVTNWLAKVNTQIDLIREK<br>MKKALENQAEATKAIINYQYNQYTEEEKNNINFNIDDLSSKLNESINSA<br>MININKFLDQCSVSYLMNSMIPYAVKRLKDFDASVRDVLLKYIYDNR<br>GTLVLQVDRLKDEVNNTLSADIPFQLSKYVDNKKLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEWRVYTYKYFKKEEEKLFLAPISDSDEFYNTI<br>QIKEYDEQPTYSCQLLFKKDEESTDEIGLIGIHRFYESGIVFEEYKDYFCI<br>SKWYLKEVKRKPYNLKLGCNWQFIPKDEGWTE |
| 19 | Chimeric toxin BoNT/A3 (1-872)-B1 (860-1291) | MPFVNKPFNYRDPGNGVDIAYIKIPNAGQMQPVKAFKIHEGVWVIPER<br>DTFTNPEEGDLNPPPEAKQVPVSYYDSTYLSTDNEKDNYLKGVIKLFD<br>RIYSTGLGRMLLSFIVKGIPFWGGSTIDTELKVIDTNCINVIEPGGSYRSE<br>ELNLVITGPSADIIQFECKSFGHDVFNLTRNGYGSTQYIRFSPDFTFGFE<br>ESLEVDTNPLLGAGTFATDPAVTLAHELIHAAHRLYGIAINPNRVLKV<br>KTNAYYEMSGLEVSFEELRTFGGNDTNFIDSLWQKKFSRDAYDNLQN<br>IARILNEAKTIVGTTTPLQYMKNIFIRKYFLSEDASGKISVNKAAFKEFY<br>RVLTRGFTELEFVNPFKVINRKTYLNFDKAVFRINIVPDENYTINEGFN<br>LEGANSNGQNTEINSRNFTRLKNFTGLFEFYKLLCVRGIIPFKTKSLDE<br>GYNKALNYLCIKVNNWDLFFSPSEDNFTNDLDKVEEITADTNIEAAEE<br>NISSDLIQQYYLTFDFDNEPENISIENLSSDIIGQLEPMPNIERFPNGKKY<br>ELDKYTMFHYLRAQEFEHGDSRIILTNSAEEALLKPNVAYTFFSSKYV<br>KKINKAVEAVIFLSWAEELVYDFTDETNEVTTMDKIADITIIVPYIGPAL<br>NIGNMVSKGEFVEAILFTGVVALLEFIPEYSLPVFGTFAIVSYIANKVLT<br>VQTINNALSKRNEKWDEVYKYTVTNWLAKVNTQIDLIREKMKKALE<br>NQAEATRAIINYQYNQYTEEEKNNINFNIDDLSSKLNRSINRAMININK<br>FLDQCSVSYLMNSMIPYAVKRLKDFDASVRDVLLKYIYDNRGTLILQV<br>DRLKDEVNNTLSADIPFQLSKYVNDKKLLSTFTEYIKNIVNTILNNIILN<br>LRYKDNNLIDLSGYGAKVEVYDGVELNDKNQFKLTSSANSKIRVTQN<br>QNIIFNSVFLDFSVSFWIRIPKYKNDGIQNYIHNEYTIINCMKNNSGWKI<br>SIRGNRIIWTLIDINGKTKSVFFEYNIREDISEYINRWFFVTITNNLNNAK<br>IYINGKLESNTDIKDIREVIANGEIIFKLDGDIDRTQFIWMKYFSIFNTEL<br>SQSNIEERYKIQSYSEYLKDFWGNPLMYNKEYYMFNAGNKNSYIKLK<br>KDSPVGEILTRSKYNQNSKYINYRDLYIGEKFIIRRKSNSQSINDDIVRK<br>EDYIYLDFFNLNQEWRVYTYKYFKKEEEKLFLAPISDSDEFYNTIQIKE<br>YDEQPTYSCQLLFKKDEESTDEIGLIGIHRFYESGIVFEEYKDYFCISKW<br>YLKEVKRKPYNLKLGCNWQFIPKDEGWTE |
| 20 | Chimeric toxin BoNT/A4 (1-872)-B1 (860-1291) | MPLVNQQINYYDPVNGVDIAYIKIPNAGKMQPVKAFKIHNKVWVIPE<br>RDIFTNPEEVDLNPPPEAKQVPISYYDSAYLSTDNEKDNYLKGVIKLFE<br>RIYSTDLGRMLLISIVRGIPFWGGGKIDTELKVIDTNCINIIQLDDSYRSE<br>ELNLAIIGPSANIIESQCSSFRDDVLNLTRNGYGSTQYIRFSPDFTVGFEE<br>SLEVDTNPLLGAGKFAQDPAVALAHELIHAEHRLYGIAINTNRVFKVN<br>TNAYYEMAGLEVSLEELITFGGNDAKFIDSLQKKEFSLYYYNKFKDIA<br>STLNKAKSIVGTTASLQYMKNVFKEKYLLSEDATGKFLVDRLKFDEL<br>YKLLTEIYTEDNFVKFFKVLNRKTYLNFDKAVFKINIVPDVNYTIHDGF<br>NLRNTNLAANFNGQNIEINNKNFDKLKNFTGLFEFYKLLCVRGIITSKT<br>KSLDEGYNKALNELCIKVNNWDLFFSPSEDNFTNDLDKVEEITSDTNIE<br>AAEENISLDLIQQYYLNFNFDNEPENTSIENLSSDIIGQLEPMPNIERFPN<br>GKKYELNKYTMFHYLRAQEFKHSNSRIILTNSAKEALLKPNIVYTFFSS<br>KYIKAINKAVEAVTFVNWIENLVYDFTDETNEVSTMDKIADITIVIPYI<br>GPALNIGNMIYKGEFVEAIIFSGAVILLEIVPEIALPVLGTFALVSYVSNK<br>VLTVQTIDNALSKRNEKWDEVYKYIVTNWLAIVNTQINLIREKMKKA<br>LENQAEATKAIINYQYNQYTEEEKNNINFNIDDLSSKLNESINSAMININ<br>KFLDQCSVSYLMNSMIPYAVKRLKDFDASVRDVLLKYIYDNRGTLIG<br>QVNRLKDKVNNTLSADIPFQLSKYVDNKKLLSTFTEYIKNILNNIILNL<br>RYKDNNLIDLSGYGAKVEVYDGVELNDKNQFKLTSSANSKIRVTQNQ<br>NIIFNSVFLDFSVSFWIRIPKYKNDGIQNYIHNEYTIINCMKNNSGWKISI<br>RGNRIIWTLIDINGKTKSVFFEYNIREDISEYINRWFFVTITNNLNNAKIY<br>INGKLESNTDIKDIREVIANGEIIFKLDGDIDRTQFIWMKYFSIFNTELSQ<br>SNIEERYKIQSYSEYLKDFWGNPLMYNKEYYMFNAGNKNSYIKLKKD<br>SPVGEILTRSKYNQNSKYINYRDLYIGEKFIIRRKSNSQSINDDIVRKED |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | YIYLDFFNLNQEWRVYTYKYFKKEEEKLFLAPISDSDEFYNTIQIKEYD<br>EQPTYSCQLLFKKDEESTDEIGLIGIHRFYESGIVFEEYKDYFCISKWYL<br>KEVKRKPYNLKLGCNWQFIPKDEGWTE |
| 21 | Chimeric toxin BoNT/A51 (1-872)-B1 (860-1291) | MLFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTELGRMLLTSIVRGIPFWGGSTIDTELKVIDTNCINVIQPDGSYRSE<br>ELNLVIIGPSADIIQFECKSFGHDVLNLTRNGYGSTQYIRFSPDFTFGFEE<br>SLEVDTNPLLGAGKFATDPAVTLAHELIHAGHRLYGIAINPNRVFKVN<br>TNAYYEMSGLEVSFEELRTFGEHDAKFIDSLQENEFRLYYYNKFKDIA<br>STLNKAKSIVGTTASLQYMKNVFKEKYLLSEDTSGKFSVDKLKFDKL<br>YKMLTEIYTEDNFVKFFKVLNRKTYLNFDKAVFKINIVPEVNYTIYDG<br>FNLRNTNLAANFNGQNTEINNMNFTKLKNFTGLFEFYKLLCVRGIITS<br>KTKSLDEGYNKALNDLCIKVNNWDLFFSPSEDNFTNDLNKGEEITSDT<br>NIEAAEENISLDLIQQYYLTFNFDNEPENISIENLSSDIIGQLELMPNIERF<br>PNGKKYELDKYTMFHYLRAQEFEHGKSRIVLTNSVNEALLNPSSVYTF<br>FSSDYVRKVNKATEAAMFLGWVEQLVYDFTDETSEVSTTDKIADITIII<br>PYIGPALNIGNMLYKDDFVGALIFSGAVILLEFIPEIAIPVLGTFALVSYI<br>ANKVLTVQTIDNALSKRNEKWGEVYKYIVTNWLAKVNTQIDLIRKK<br>MKEALENQAEATKAIINYQYNQYTEEEKNNINFNIGDLSSKLNDSINK<br>AMININKFLNQCSVSYLMNSMIPYGVKRLEDFDASLKDALLKYIYDNR<br>GTLIGQVDRLKDKVNNTLSTDIPFQLSKYVDNQRLLSTFTEYIKNILNN<br>IILNLRYKDNNLIDLSGYGAKVEVYDGVELNDKNQFKLTSSANSKIRV<br>TQNQNIIFNSVFLDFSVSFWIRIPKYKNDGIQNYIHNEYTIINCMKNNSG<br>WKISIRGNRIIWTLIDINGKTKSVFFEYNIREDISEYINRWFFVTITNNLN<br>NAKIYINGKLESNTDIKDIREVIANGEIIFKLDGDIDRTQFIWMKYFSIFN<br>TELSQSNIEERYKIQSYSEYLKDFWGNPLMYNKEYYMFNAGNKNSYI<br>KLKKDSPVGEILTRSKYNQNSKYINYRDLYIGEKFIIRRKSNSQSINDDI<br>VRKEDYIYLDFFNLNQEWRVYTYKYFKKEEEKLFLAPISDSDEFYNTI<br>QIKEYDEQPTYSCQLLFKKDEESTDEIGLIGIHRFYESGIVFEEYKDYFCI<br>SKWYLKEVKRKPYNLKLGCNWQFIPKDEGWTE |
| 22 | Chimeric toxin BoNT/A6 (1-872)-B1 (860-1291) | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFAKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLSAQEFEHGKSRIDLTNSVNEALLNPSHVYT<br>FFSSDYVKKVNKATEAAMFLGWVEQLVYDFTDETSEVSTTDKIADITII<br>IPYIGPALNIGNMLYKDDFVGALIFSGAVILLEFIPEIAIPVLGTFAIVSYI<br>ANKVLTVQTINNALSKRNEKWDEVYKYTVTNWLAKVNTQIDLIREK<br>MKKALENQAEATKAIINYQYNQYTEEEKNNINFNIDDLSSKLNESINSA<br>MININKFLDQCSVSYLMNSMIPYAVKRLKDFDASVRDVLLKYIYDNR<br>GTLIGQVDRLKDKVNNTLSTDIPFQLSKYVDNQRLLSTFTEYIKNILNN<br>IILNLRYKDNNLIDLSGYGAKVEVYDGVELNDKNQFKLTSSANSKIRV<br>TQNQNIIFNSVFLDFSVSFWIRIPKYKNDGIQNYIHNEYTIINCMKNNSG<br>WKISIRGNRIIWTLIDINGKTKSVFFEYNIREDISEYINRWFFVTITNNLN<br>NAKIYINGKLESNTDIKDIREVIANGEIIFKLDGDIDRTQFIWMKYFSIFN<br>TELSQSNIEERYKIQSYSEYLKDFWGNPLMYNKEYYMFNAGNKNSYI<br>KLKKDSPVGEILTRSKYNQNSKYINYRDLYIGEKFIIRRKSNSQSINDDI<br>VRKEDYIYLDFFNLNQEWRVYTYKYFKKEEEKLFLAPISDSDEFYNTI<br>QIKEYDEQPTYSCQLLFKKDEESTDEIGLIGIHRFYESGIVFEEYKDYFCI<br>SKWYLKEVKRKPYNLKLGCNWQFIPKDEGWTE |
| 23 | Chimeric toxin BoNT/A7 (1-872)-B1 (860-1291) | MPFVNKQFNYKDPVNGVDIAYIKIPNAGQMQPVKAFKIHNKIWVIPER<br>DIFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIINFECKSFGHDVLNLTRNGYGSTQYIRFSPDFTFGFE<br>ESLEVDTNPLLGAGKFAIDPAVTLAHELIHAGHRLYGIAINPNRVFKVN<br>TNAYYEMSGLEVSFEELRTFGGHDAKFIDSLQENEFRLYYYNKFKEVA<br>SILNKAKSIIGTTASLQYMKNVFKEKYLLSEDTSGKFSVDKLRFDKLY<br>KMLTEIYTEDNFVKFFKVLNRKTYLNFDKAVFKMNIVPEVNYTIYDGF<br>NLRNTNLAANFNGQNTEINNMNFTKLKNFTGLFEFYKLLCVRGIITSK<br>TKSLDEGYNKALNDLCIKVNNWDLFFSPSEDNFTNDLNKGEEITSDTN<br>IEAAEENISSDLIQQYYLTFNFDNEPENISIENLSSDIIGQLELMPNIERFP<br>NGKKYELDKYTMFHYLRAQEFEYGNSRIVLINSVNEALLNPSSVYTFF<br>SSDYVKKANEATEAAMFLGWVEQLVYDFTDETSEVSTMDKIADITIIV<br>PYIGPALNIGNMVYKKKFEEALIFSGAVILLEFVPEIVLPILGTFALVSYT |

TABLE 1-continued

| SEQ ID NO | Description | Sequence |
|---|---|---|
| | | SNKVLTVRTIDNALSKRNEKWEEVYKYIVTNWLAKVNTQINLIRKKM<br>KEALENQAEATKAIINYQYNQYTEEEKNNINFNIGDLSSKLNDSINKA<br>MININKFLDQCSVSYLMNSMIPQGVKQLKDFDTSLRDSLLKYIYDNRG<br>TLIGQVDRLKDKVNNTLSTDIPFQLSKYADNQRLLSTFTEYIKNILNNII<br>LNLRYKDNNLIDLSGYGAKVEVYDGVELNDKNQFKLTSSANSKIRVT<br>QNQNIIFNSVFLDFSVSFWIRIPKYKNDGIQNYIHNEYTIINCMKNNSG<br>WKISIRGNRIIWTLIDINGKTKSVFFEYNIREDISEYINRWFFVTITNNLN<br>NAKIYINGKLESNTDIKDIREVIANGEIIFKLDGDIDRTQFIWMKYFSIFN<br>TELSQSNIEERYKIQSYSEYLKDFWGNPLMYNKEYYMFNAGNKNSYI<br>KLKKDSPVGEILTRSKYNQNSKYINYRDLYIGEKFIIRRKSNSQSINDDI<br>VRKEDYIYLDFFNLNQEWRVYTYKYFKKEEEKLFLAPISDSDEFYNTI<br>QIKEYDEQPTYSCQLLFKKDEESTDEIGLIGIHRFYESGIVFEEYKDYFCI<br>SKWYLKEVKRKPYNLKLGCNWQFIPKDEGWTE |
| 24 | Chimeric toxin BoNT/A8 (1-872)-B1 (860-1292) | MPFVNKQFNYKDTVNGIDIAYIKIPNAGQMQPVKAFKIHNKIWVIPER<br>DTFTNPKEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHDVLNLTRNGYGSTQYIRFSPDFTFGFE<br>ESLEVDTNPLLGAGKFATDPAVTLAHELIHAEHRLYGIAINPNRVFKV<br>NTNAYYEMSGLEVSFEELRTFGGHNAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPDENYTIKD<br>GFNLKNTNLAANFNGQNTEINSRNFTKLKNFTGLFEFYKLLCVRGIIPF<br>KTKSLDEGYNKALNDLCIKVNNWDLFFSPSEDNFTNDLDKVEEITSDT<br>NIEAAEENISLDLIQQYYLTFDFDNEPENISIENLSSDIIGQLEPMPNIERF<br>PNGKKYELDKYTMFHYLRAQEFEHSKSRIALTNSVNEALLNPSRVYTF<br>FSSDYVKKVNKATEAAMFLGWVEQLVYDFTDETSEVSTTDKIADITIII<br>PYIGPALNIGNMLYKDDFVGALIFSGAVILLEFIPEIAIPVLGTFALVSYI<br>ANKVLTVQTIDNALSKRNEKWDEVYKYIVTNWLAKVNTQIDLVRKK<br>MKEALENQAEATKAIINYQYNQYTEEEKNNINFNIDDLSSKLNESINSA<br>MTNINKFLDQCSVSYLMNSMIPYAVKRLKDFDASVREVLLKYIYDNR<br>GTLILQVDRLKDKVNNTLSADIPFQLSKYVDNKKLLSTFTEYIKNILNN<br>IILNLRYKDNNLIDLSGYGAKVEVYDGVELNDKNQFKLTSSANSKIRV<br>TQNQNIIFNSVFLDFSVSFWIRIPKYKNDGIQNYIHNEYTIINCMKNNSG<br>WKISIRGNRIIWTLIDINGKTKSVFFEYNIREDISEYINRWFFVTITNNLN<br>NAKIYINGKLESNTDIKDIREVIANGEIIFKLDGDIDRTQFIWMKYFSIFN<br>TELSQSNIEERYKIQSYSEYLKDFWGNPLMYNKEYYMFNAGNKNSYI<br>KLKKDSPVGEILTRSKYNQNSKYINYRDLYIGEKFIIRRKSNSQSINDDI<br>VRKEDYIYLDFFNLNQEWRVYTYKYFKKEEEKLFLAPISDSDEFYNTI<br>QIKEYDEQPTYSCQLLFKKDEESTDEIGLIGIHRFYESGIVFEEYKDYFCI<br>SKWYLKEVKRKPYNLKLGCNWQFIPKDEGWTE |
| 25 | BoNT/B1 loop peptide (1245-1252) | ESGIVFEE |
| 26 | BoNT/B2 loop peptide (1245-1252) | ESGIVLKD |
| 27 | BoNT/B3 loop peptide (1245-1252) | ESGIVFKD |
| 28 | BoNT/B4 loop peptide (1245-1252) | ESGVLRKK |
| 29 | BoNT/B5 loop peptide (1245-1252) | ESGIVFKE |
| 30 | BoNT/B6 loop peptide (1245-1252) | ESGIVFKD |
| 31 | BoNT/B7 loop peptide (1245-1252) | ESGILFKD |
| 32 | BoNT/B8 loop peptide (1246-1253) | ESGFVFQE |
| 33 | BoNT/B1 I1228W/V1249W | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE |

*Clostridial Botulinum* neurotoxin (BoNT) amino acid sequences
*amino acid positions where substitutions occur are underlined TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE<br>KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEWRV<br>YTYKYFKKEEEKLFLAPISDSDEFYNTIQIKEYDEQPTYSCQLLFKKDE<br>ESTDEIGLIGIHRFYESGWWFEEYKDYFCISKWYLKEVKRKPYNLKLG<br>CNWQFIPKDEGWTE |
| 34 | Receptor binding domain of BoNT/B1 I389W/V390W | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY<br>FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEWRVYTYKYFKKEEEKLFLAPISDSDEF<br>YNTIQIKEYDEQPTYSCQLLFKKDEESTDEIGLIGIHRFYESGWWFEEY<br>KDYFCISKWYLKEVKRKPYNLKLGCNWQFIPKDEGWTE |
| 35 | Chimeric toxin BoNT/A1-B1 I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEWRVYTYKYFKKEEEKLFLAPISDSDEFYNTI<br>QIKEYDEQPTYSCQLLFKKDEESTDEIGLIGIHRFYESGWWFEEYKDYF<br>CISKWYLKEVKRKPYNLKLGCNWQFIPKDEGWTE |
| 36 | Chimeric toxin BoNT/A2-B1 I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHDVLNLTRNGYGSTQYIRFSPDFTFGFE<br>ESLEVDTNPLLGAGKFATDPAVTLAHELIHAEHRLYGIAINPNRVFKV<br>NTNAYYEMSGLEVSFEELRTFGGHDAKFIDSLQENEFRLYYYNKFKD<br>VASTLNKAKSIIGTTASLQYMKNVFKEKYLLSEDTSGKFSVDKLKFDK<br>LYKMLTEIYTEDNFVNFFKVINRKTYLNFDKAVFRINIVPDENYTIKDG<br>FNLKGANLSTNFNGQNTEINSRNFTRLKNFTGLFEFYKLLCVRGIIPFK<br>TKSLDEGYNKALNDLCIKVNNWDLFFSPSEDNFTNDLDKVEEITADTN<br>IEAAEENISLDLIQQYYLTFDFDNEPENISIENLSSDIIGQLEPMPNIERFP<br>NGKKYELDKYTMFHYLRAQEFEHGDSRIILTNSAEEALLKPNVAYTFF<br>SSKYVKKINKAVEAFMFLNWAEELVYDFTDETNEVTTMDKIADITIIV<br>PYIGPALNIGNMLSKGEFVEAIIFTGVVAMLEFIPEYALPVFGTFAIVSYI<br>ANKVLTVQTINNALSKRNEKWDEVYKYTVTNWLAKVNTQIDLIREK<br>MKKALENQAEATKAIINYQYNQYTEEEKNNINFNIDDLSSKLNESINSA |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | MININKFLDQCSVSYLMNSMIPYAVKRLKDFDASVRDVLLKYIYDNR<br>GTLVLQVDRLKDEVNNTLSADIPFQLSKYVDNKKLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEWRVYTYKYFKKEEEKLFLAPISDSDEFYNTI<br>QIKEYDEQPTYSCQLLFKKDEESTDEIGLIGIHRFYESGWWFEEYKDYF<br>CISKWYLKEVKRKPYNLKLGCNWQFIPKDEGWTE |
| 37 | BoNT/B1 loop peptide I4W/I5W | ESGWWFEE |
| 38 | BoNT/A1 fragment (1-872) | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKN |
| 39 | BoNT/A2 fragment (1-872) | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHDVLNLTRNGYGSTQYIRFSPDFTFGFE<br>ESLEVDTNPLLGAGKFATDPAVTLAHELIHAEHRLYGIAINPNRVFKV<br>NTNAYYEMSGLEVSFEELRTFGGHDAKFIDSLQENEFRLYYYNKFKD<br>VASTLNKAKSIIGTTASLQYMKNVFKEKYLLSEDTSGKFSVDKLKFDK<br>LYKMLTEIYTEDNFVNFFKVINRKTYLNFDKAVFRINIVPDENYTIKDG<br>FNLKGANLSTNFNGQNTEINSRNFTRLKNFTGLFEFYKLLCVRGIIPFK<br>TKSLDEGYNKALNDLCIKVNNWDLFFSPSEDNFTNDLDKVEEITADTN<br>IEAAEENISLDLIQQYYLTFDFDNEPENISIENLSSDIIGQLEPMPNIERFP<br>NGKKYELDKYTMFHYLRAQEFEHGDSRIILTNSAEEALLKPNVAYTFF<br>SSKYVKKINKAVEAFMFLNWAEELVYDFTDETNEVTTMDKIADITIIV<br>PYIGPALNIGNMLSKGEFVEAIIFTGVVAMLEFIPEYALPVFGTFAIVSYI<br>ANKVLTVQTINNALSKRNEKWDEVYKYTVTNWLAKVNTQIDLIREK<br>MKKALENQAEATKAIINYQYNQYTEEEKNNINFNIDDLSSKLNESINSA<br>MININKFLDQCSVSYLMNSMIPYAVKRLKDFDASVRDVLLKYIYDNR<br>GTLVLQVDRLKDEVNNTLSADIPFQLSKYVDNKKLLSTFTEYIKN |
| 40 | BoNT/A3 fragment (1-872) | MPFVNKPFNYRDPGNGVDIAYIKIPNAGQMQPVKAFKIHEGVWVIPER<br>DTFTNPEEGDLNPPPEAKQVPVSYYDSTYLSTDNEKDNYLKGVIKLFD<br>RIYSTGLGRMLLSFIVKGIPFWGGSTIDTELKVIDTNCINVIEPGGSYRSE<br>ELNLVITGPSADIIQFECKSFGHDVFNLTRNGYGSTQYIRFSPDFTFGFE<br>ESLEVDTNPLLGAGTFATDPAVTLAHELIHAAHRLYGIAINPNRVLKV<br>KTNAYYEMSGLEVSFEELRTFGGNDTNFISLWQKKFSRDAYDNLQN<br>IARILNEAKTIVGTTTPLQYMKNIFIRKYFLSEDASGKISVNKAAFKEFY<br>RVLTRGFTELEFVNPFKVINRKTYLNFDKAVFRINIVPDENYTINEGFN<br>LEGANSNGQNTEINSRNFTRLKNFTGLFEFYKLLCVRGIIPFKTKSLDE<br>GYNKALNYLCIKVNNWDLFFSPSEDNFTNDLDKVEEITADTNIEAAEE<br>NISSDLIQQYYLTFDFDNEPENISIENLSSDIIGQLEPMPNIERFPNGKKY<br>ELDKYTMFHYLRAQEFEHGDSRIILTNSAEEALLKPNVAYTFFSSKYV<br>KKINKAVEAVIFLSWAEELVYDFTDETNEVTTMDKIADITIIVPYIGPAL<br>NIGNMVSKGEFVEAILFTGVVALLEFIPEYSLPVFGTFAIVSYIANKVLT<br>VQTINNALSKRNEKWDEVYKYTVTNWLAKVNTQIDLIREKMKKALE<br>NQAEATRAIINYQYNQYTEEEKNNINFNIDDLSSKLNRSINRAMININK<br>FLDQCSVSYLMNSMIPYAVKRLKDFDASVRDVLLKYIYDNRGTLILQV<br>DRLKDEVNNTLSADIPFQLSKYVNDKKLLSTFTEYIKNIVNT |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| 41 | BoNT/A4 fragment (1-872) | MPLVNQQINYYDPVNGVDIAYIKIPNAGKMQPVKAFKIHNKVWVIPE<br>RDIFTNPEEVDLNPPPEAKQVPISYYDSAYLSTDNEKDNYLKGVIKLFE<br>RIYSTDLGRMLLISIVRGIPFWGGGKIDTELKVIDTNCINIIQLDDSYRSE<br>ELNLAIIGPSANIIESQCSSFRDDVLNLTRNGYGSTQYIRFSPDFTVGFEE<br>SLEVDTNPLLGAGKFAQDPAVALAHELIHAEHRLYGIAINTNRVFKVN<br>TNAYYEMAGLEVSLEELITFGGNDAKFIDSLQKKEFSLYYYNKFKDIA<br>STLNKAKSIVGTTASLQYMKNVFKEKYLLSEDATGKFLVDRLKFDEL<br>YKLLTEIYTEDNFVKFFKVLNRKTYLNFDKAVFKINIVPDVNYTIHDGF<br>NLRNTNLAANFNGQNIEINNKNFDKLKNFTGLFEFYKLLCVRGIITSKT<br>KSLDEGYNKALNELCIKVNNWDLFFSPSEDNFTNDLDKVEEITSDTNIE<br>AAEENISLDLIQQYYLNFNFDNEPENTSIENLSSDIIGQLEPMPNIERFPN<br>GKKYELNKYTMFHYLRAQEFKHSNSRIILTNSAKEALLKPNIVYTFFSS<br>KYIKAINKAVEAVTFVNWIENLVYDFTDETNEVSTMDKIADITIVIPYI<br>GPALNIGNMIYKGEFVEAIIFSGAVILLEIVPEIALPVLGTFALVSYVSNK<br>VLTVQTIDNALSKRNEKWDEVYKYIVTNWLAIVNTQINLIREKMKKA<br>LENQAEATKAIINYQYNQYTEEEKNNINFNIDDLSSKLNESINSAMININ<br>KFLDQCSVSYLMNSMIPYAVKRLKDFDASVRDVLLKYIYDNRGTLIG<br>QVNRLKDKVNNTLSADIPFQLSKYVDNKKLLSTFTEYIKN |
| 42 | BoNT/A5 fragment (1-872) | MLFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTELGRMLLTSIVRGIPFWGGSTIDTELKVIDTNCINVIQPDGSYRSE<br>ELNLVIIGPSADIIQFECKSFGHDVLNLTRNGYGSTQYIRFSPDFTFGFEE<br>SLEVDTNPLLGA<br>GKFATDPAVTLAHELIHAGHRLYGIAINPNRVFKVNTNAYYEMSGLE<br>VSFEELRTFGEHDAKFIDSLQENEFRLYYYNKFKDIASTLNKAKSIVGT<br>TASLQYMKNVFKEKYLLSEDTSGKFSVDKLKFDKLYKMLTEIYTEDN<br>FVKFFKVLNRKTYLNFDKAVFKINIVPEVNYTIYDGFNLRNTNLAANF<br>NGQNTEINNMNFTKLKNFTGLFEFYKLLCVRGIITSKTKSLDEGYNKA<br>LNDLCIKVNNWDLFFSPSEDNFTNDLNKGEEITSDTNIEAAEENISLDLI<br>QQYYLTFNFDNEPENISIENLSSDIIGQLELMPNIERFPNGKKYELDKYT<br>MFHYLRAQEFEHGKSRIVLTNSVNEALLNPSSVYTFFSSDYVRKVNKA<br>TEAAMFLGWVEQLVYDFTDETSEVSTTDKIADITIIIPYIGPALNIGNML<br>YKDDFVGALIFSGAVILLEFIPEIAIPVLGTFALVSYIANKVLTVQTIDNA<br>LSKRNEKWGEVYKYIVTNWLAKVNTQIDLIRKKMKEALENQAEATK<br>AIINYQYNQYTEEEKNNINFNIGDLSSKLNDSINKAMININKFLNQCSVS<br>YLMNSMIPYGVKRLEDFDASLKDALLKYIYDNRGTLIGQVDRLKDKV<br>NNTLSTDIPFQLSKYVDNQRLLSTFTEYIKN |
| 43 | BoNT/A6 fragment (1-872) | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFAKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLSAQEFEHGKSRIDLTNSVNEALLNPSHVYT<br>FFSSDYVKKVNKATEAAMFLGWVEQLVYDFTDETSEVSTTDKIADITII<br>IPYIGPALNIGNMLYKDDFVGALIFSGAVILLEFIPEIAIPVLGTFAIVSYI<br>ANKVLTVQTINNALSKRNEKWDEVYKYTVTNWLAKVNTQIDLIREK<br>MKKALENQAEATKAIINYQYNQYTEEEKNNINFNIDDLSSKLNESINSA<br>MININKFLDQCSVSYLMNSMIPYAVKRLKDFDASVRDVLLKYIYDNR<br>GTLIGQVDRLKDKVNNTLSTDIPFQLSKYVDNQRLLSTFTEYIKN |
| 44 | BoNT/A7 fragment (1-872) | MPFVNKQFNYKDPVNGVDIAYIKIPNAGQMQPVKAFKIHNKIWVIPER<br>DIFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIINFECKSFGHDVLNLTRNGYGSTQYIRFSPDFTFGFE<br>ESLEVDTNPLLGAGKFAIDPAVTLAHELIHAGHRLYGIAINPNRVFKVN<br>TNAYYEMSGLEVSFEELRTFGGHDAKFIDSLQENEFRLYYYNKFKEVA<br>SILNKAKSIIGTTASLQYMKNVFKEKYLLSEDTSGKFSVDKLRFDKLY<br>KMLTEIYTEDNFVKFFKVLNRKTYLNFDKAVFKMNIVPEVNYTIYDGF<br>NLRNTNLAANFNGQNTEINNMNFTKLKNFTGLFEFYKLLCVRGIITSK<br>TKSLDEGYNKALNDLCIKVNNWDLFFSPSEDNFTNDLNKGEEITSDTN<br>IEAAEENISSDLIQQYYLTFNFDNEPENISIENLSSDIIGQLELMPNIERFP<br>NGKKYELDKYTMFHYLRAQEFEYGNSRIVLINSVNEALLNPSSVYTFF<br>SSDYVKKANEATEAAMFLGWVEQLVYDFTDETSEVSTMDKIADITIIV<br>PYIGPALNIGNMVYKKKFEEALIFSGAVILLEFVPEIVLPILGTFALVSYT<br>SNKVLTVRTIDNALSKRNEKWEEVYKYIVTNWLAKVNTQINLIRKKM<br>KEALENQAEATKAIINYQYNQYTEEEKNNINFNIGDLSSKLNDSINKA |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | MININKFLDQCSVSYLMNSMIPQGVKQLKDFDTSLRDSLLKYIYDNRG<br>TLIGQVDRLKDKVNNTLSTDIPFQLSKYADNQRLLSTFTEYIKN |
| 45 | BoNT/A8 fragment (1-872) | MPFVNKQFNYKDTVNGIDIAYIKIPNAGQMQPVKAFKIHNKIWVIPER<br>DTFTNPKEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHDVLNLTRNGYGSTQYIRFSPDFTFGFE<br>ESLEVDTNPLLGAGKFATDPAVTLAHELIHAEHRLYGIAINPNRVFKV<br>NTNAYYEMSGLEVSFEELRTFGGHNAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPDENYTIKD<br>GFNLKNTNLAANFNGQNTEINSRNFTKLKNFTGLFEFYKLLCVRGIIPF<br>KTKSLDEGYNKALNDLCIKVNNWDLFFSPSEDNFTNDLDKVEEITSDT<br>NIEAAEENISLDLIQQYYLTFDFDNEPENISIENLSSDIIGQLEPMPNIERF<br>PNGKKYELDKYTMFHYLRAQEFEHSKSRIALTNSVNEALLNPSRVYTF<br>FSSDYVKKVNKATEAAMFLGWVEQLVYDFTDETSEVSTTDKIADITIII<br>PYIGPALNIGNMLYKDDFVGALIFSGAVILLEFIPEIAIPVLGTFALVSYI<br>ANKVLTVQTIDNALSKRNEKWDEVYKYIVTNWLAKVNTQIDLVRKK<br>MKEALENQAEATKAIINYQYNQYTEEEKNNINFNIDDLSSKLNESINSA<br>MTNINKFLDQCSVSYLMNSMIPYAVKRLKDFDASVREVLLKYIYDNR<br>GTLILQVDRLKDKVNNTLSADIPFQLSKYVDNKKLLSTFTEYIKN |
| 46 | BoNT/B1 E1191M/S1199Y/ I1248W/V1249W | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE<br>KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEWRV<br>YTYKYFKKEEMKLFLAPIYDSDEFYNTIQIKEYDEQPTYSCQLLFKKDE<br>ESTDEIGLIGIHRFYESGWWFEEYKDYFCISKWYLKEVKRKPYNLKLG<br>CNWQFIPKDEGWTE |
| 47 | BoNT/B1 E1191M/S1199W/ I1248W/V1249W | MPVTINNFNYNDPIDNNNIIMMEPPFARGTGRYYKAFKITDRIWIIPER<br>YTFGYKPEDFNKSSGIFNRDVCEYYDPDYLNTNDKKNILQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE<br>KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEWRV |

TABLE 1-continued

| SEQ ID NO | Description | Sequence |
|---|---|---|
| | | *Clostridial Botulinum* neurotoxin (BoNT) amino acid sequences<br>*amino acid positions where substitutions occur are underlined |
| | | YTYKYFKKEEMKLFLAPIWDSDEFYNTIQIKEYDEQPTYSCQLLFKKD<br>EESTDEIGLIGIHRFYESGWWFEEYKDYFCISKWYLKEVKRKPYNLKL<br>GCNWQFIPKDEGWTE |
| 48 | BoNT/B1 E1191M/W1178Q/ I1248W/V1249W | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE<br>KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEQRVY<br>TYKYFKKEEMKLFLAPISDSDEFYNTIQIKEYDEQPTYSCQLLFKKDEE<br>STDEIGLIGIHRFYESGWWFEEYKDYFCISKWYLKEVKRKPYNLKLGC<br>NWQFIPKDEGWTE |
| 49 | BoNT/B1 E1191V/S1199Y/ I1248W/V1249W | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE<br>KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEWRV<br>YTYKYFKKEEVKLFLAPIYDSDEFYNTIQIKEYDEQPTYSCQLLFKKDE<br>ESTDEIGLIGIHRFYESGWWFEEYKDYFCISKWYLKEVKRKPYNLKLG<br>CNWQFIPKDEGWTE |
| 50 | BoNT/B1 E1191V/S1199W/ I1248W/V1249W | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEWRV<br>YTYKYFKKEEVKLFLAPIWDSDEFYNTIQIKEYDEQPTYSCQLLFKKD<br>EESTDEIGLIGIHRFYESGWWFEEYKDYFCISKWYLKEVKRKPYNLKL<br>GCNWQFIPKDEGWTE |
| 51 | BoNT/B1<br>E1191V/S1178Q/<br>I1248W/V1249W | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE<br>KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEQRVY<br>TYKYFKKEEVKLFLAPISDSDEFYNTIQIKEYDEQPTYSCQLLFKKDEE<br>STDEIGLIGIHRFYESGWWFEEYKDYFCISKWYLKEVKRKPYNLKLGC<br>NWQFIPKDEGWTE |
| 52 | BoNT/B1<br>E1191Q/S1199Y/<br>I1248W/V1249W | MPVTINNFNYNDPIDNNNIIMMEPPFARGTGRYYKAFKITDRIWIIPER<br>YTFGYKPEDFNKSSGIFNRDVCEYYDPDYLNTNDKKNIFLQTMIKLFN<br>RIKSKPLGEKLLEMIINGIPYLGDRRVPLEEFNTNIASVTVNKLISNPGE<br>VERKKGIFANLIIFGPGPVLNENETIDIGIQNHFASREGFGGIMQMKFCP<br>EYVSVFNNVQENKGASIFNRRGYFSDPALILMHELIHVLHGLYGIKVD<br>DLPIVPNEKKFFMQSTDAIQAEELYTFGGQDPSIITPSTDKSIYDKVLQN<br>FRGIVDRLNKVLVCISDPNININIYKNKFKDKYKFVEDSEGKYSIDVESF<br>DKLYKSLMFGFTETNIAENYKIKTRASYFSDSLPPVKIKNLLDNEIYTIE<br>EGFNISDKDMEKEYRGQNKAINKQAYEEISKEHLAVYKIQMCKSVKA<br>PGICIDVDNEDLFFIADKNSFSDDLSKNERIEYNTQSNYIENDFPINELIL<br>DTDLISKIELPSENTESLTDFNVDVPVYEKQPAIKKIFTDENTIFQYLYS<br>QTFPLDIRDISLTSSFDDALLFSNKVYSFFSMDYIKTANKVVEAGLFAG<br>WVKQIVNDFVIEANKSNTMDKIADISLIVPYIGLALNVGNETAKGNFE<br>NAFEIAGASILLEFIPELLIPVVGAFLLESYIDNKNKIIKTIDNALTKRNE<br>KWSDMYGLIVAQWLSTVNTQFYTIKEGMYKALNYQAQALEEIIKYRY<br>NIYSEKEKSNINIDFNDINSKLNEGINQAIDNINNFINGCSVSYLMKKMI<br>PLAVEKLLDFDNTLKKNLLNYIDENKLYLIGSAEYEKSKVNKYLKTIM<br>PFDLSIYTNDTILIEMFNKYNSEILNNIILNLRYKDNNLIDLSGYGAKVE<br>VYDGVELNDKNQFKLTSSANSKIRVTQNQNIIFNSVFLDFSVSFWIRIP<br>KYKNDGIQNYIHNEYTIINCMKNNSGWKISIRGNRIIWTLIDINGKTKS<br>VFFEYNIREDISEYINRWFFVTITNNLNNAKIYINGKLESNTDIKDIREVI<br>ANGEIIFKLDGDIDRTQFIWMKYFSIFNTELSQSNIEERYKIQSYSEYLK<br>DFWGNPLMYNKEYYMFNAGNKNSYIKLKKDSPVGEILTRSKYNQNS<br>KYINYRDLYIGEKFIIRRKSNSQSINDDIVRKEDYIYLDFFNLNQEWRV<br>YTYKYFKKEEQKLFLAPIYDSDEFYNTIQIKEYDEQPTYSCQLLFKKDE<br>ESTDEIGLIGIHRFYESGWWFEEYKDYFCISKWYLKEVKRKPYNLKLG<br>CNWQFIPKDEGWTE |
| 53 | BoNT/B1 receptor<br>binding domain<br>E332M/S340Y/<br>I389W/V390W | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEWRVYTYKYFKKEEMKLFLAPIYDSDEF<br>YNTIQIKEYDEQPTYSCQLLFKKDEESTDEIGLIGIHRFYESGWWFEEY<br>KDYFCISKWYLKEVKRKPYNLKLGCNWQFIPKDEGWTE |
| 54 | BoNT/B1 receptor binding domain E332M/S340W/ I389W/V390W | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY<br>FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEWRVYTYKYFKKEEMKLFLAPIWDSDE<br>FYNTIQIKEYDEQPTYSCQLLFKKDEESTDEIGLIGIHRFYESGWWFEE<br>YKDYFCISKWYLKEVKRKPYNLKLGCNWQFIPKDEGWTE |
| 55 | BoNT/B1 receptor binding domain E332M/W318Q/ I389W/V390W | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY<br>FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEQRVYTYKYFKKEEMKLFLAPISDSDEF<br>YNTIQIKEYDEQPTYSCQLLFKKDEESTDEIGLIGIHRFYESGWWFEEY<br>KDYFCISKWYLKEVKRKPYNLKLGCNWQFIPKDEGWTE |
| 56 | BoNT/B1 receptor binding domain E332V/W318Q/ I389W/V390W | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY<br>FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEQRVYTYKYFKKEEVKLFLAPISDSDEF<br>YNTIQIKEYDEQPTYSCQLLFKKDEESTDEIGLIGIHRFYESGWWFEEY<br>KDYFCISKWYLKEVKRKPYNLKLGCNWQFIPKDEGWTE |
| 57 | BoNT/B1 receptor binding domain E332V/S340Y/ I389W/V390W | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY<br>FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEWRVYTYKYFKKEEVKLFLAPIYDSDEF<br>YNTIQIKEYDEQPTYSCQLLFKKDEESTDEIGLIGIHRFYESGWWFEEY<br>KDYFCISKWYLKEVKRKPYNLKLGCNWQFIPKDEGWTE |
| 58 | BoNT/B1 receptor binding domain E332V/S340W/ I389W/V390W | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY<br>FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEWRVYTYKYFKKEEVKLFLAPIWDSDEF<br>YNTIQIKEYDEQPTYSCQLLFKKDEESTDEIGLIGIHRFYESGWWFEEY<br>KDYFCISKWYLKEVKRKPYNLKLGCNWQFIPKDEGWTE |
| 59 | BoNT/B1 receptor binding domain E332Q/S340Y/ I389W/V390W | ILNNIILNLRYKDNNLIDLSGYGAKVEVYDGVELNDKNQFKLTSSANS<br>KIRVTQNQNIIFNSVFLDFSVSFWIRIPKYKNDGIQNYIHNEYTIINCMK<br>NNSGWKISIRGNRIIWTLIDINGKTKSVFFEYNIREDISEYINRWFFVTIT<br>NNLNNAKIYINGKLESNTDIKDIREVIANGEIIFKLDGDIDRTQFIWMKY<br>FSIFNTELSQSNIEERYKIQSYSEYLKDFWGNPLMYNKEYYMFNAGNK<br>NSYIKLKKDSPVGEILTRSKYNQNSKYINYRDLYIGEKFIIRRKSNSQSI<br>NDDIVRKEDYIYLDFFNLNQEWRVYTYKYFKKEEQKLFLAPIYDSDEF<br>YNTIQIKEYDEQPTYSCQLLFKKDEESTDEIGLIGIHRFYESGWWFEEY<br>KDYFCISKWYLKEVKRKPYNLKLGCNWQFIPKDEGWTE |
| 60 | Chimeric toxin BoNT/A1-B1 E1204M/S1212Y/ I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEWRVYTYKYFKKEEMKLFLAPIYDSDEFYNTI<br>QIKEYDEQPTYSCQLLFKKDEESTDEIGLIGIHRFYESGWWFEEYKDYF<br>CISKWYLKEVKRKPYNLKLGCNWQFIPKDEGWTE |
| 61 | Chimeric toxin<br>BoNT/A1-B1<br>E1204M/S1212W/<br>I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEWRVYTYKYFKKEEMKLFLAPIWDSDEFYNT<br>IQIKEYDEQPTYSCQLLFKKDEESTDEIGLIGIHRFYESGWWFEEYKDY<br>FCISKWYLKEVKRKPYNLKLGCNWQFIPKDEGWTE |
| 62 | Chimeric toxin<br>BoNT/A1-B1<br>E1204M/W1191Q/<br>I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | IKLKKDSPVGEILTRSKYNQNSKYINYRDLYIGEKFIIRRKSNSQSINDDI<br>VRKEDYIYLDFFNLNQEQRVYTYKYFKKEEMKLFLAPISDSDEFYNTI<br>QIKEYDEQPTYSCQLLFKKDEESTDEIGLIGIHRFYESGWWFEEYKDYF<br>CISKWYLKEVKRKPYNLKLGCNWQFIPKDEGWTE |
| 63 | Chimeric toxin BoNT/A1-B1 E1204V/S1212Y/ I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEWRVYTYKYFKKEEVKLFLAPIYDSDEFYNTI<br>QIKEYDEQPTYSCQLLFKKDEESTDEIGLIGIHRFYESGWWFEEYKDYF<br>CISKWYLKEVKRKPYNLKLGCNWQFIPKDEGWTE |
| 64 | Chimeric toxin BoNT/A1-B1 E1204V/S1212W/ I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEWRVYTYKYFKKEEVKLFLAPIWDSDEFYNTI<br>QIKEYDEQPTYSCQLLFKKDEESTDEIGLIGIHRFYESGWWFEEYKDYF<br>CISKWYLKEVKRKPYNLKLGCNWQFIPKDEGWTE |
| 65 | Chimeric toxin BoNT/A1-B1 E1204V/W1191Q/ I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT |

TABLE 1-continued

*Clostridial Botulinum* neurotoxin (BoNT) amino acid sequences
*amino acid positions where substitutions occur are underlined

| SEQ ID NO | Description | Sequence |
|---|---|---|
| | | IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKLKKDSPVGEILTRSKYNQNSKYINYRDLYIGEKFIIRRKSNSQSINDDI<br>VRKEDYIYLDFFNLNQEQRVYTYKYFKKEEVKLFLAPISDSDEFYNTIQ<br>IKEYDEQPTYSCQLLFKKDEESTDEIGLIGIHRFYESGWWFEEYKDYFC<br>ISKWYLKEVKRKPYNLKLGCNWQFIPKDEGWTE |
| 66 | Chimeric toxin BoNT/A1-B1 E1204Q/S1212Y/ I1261W/V1262W | MPFVNKQFNYKDPVNGVDIAYIKIPNAGQMQPVKAFKIHNKIWVIPER<br>DTFTNPEEGDLNPPPEAKQVPVSYYDSTYLSTDNEKDNYLKGVTKLFE<br>RIYSTDLGRMLLTSIVRGIPFWGGSTIDTELKVIDTNCINVIQPDGSYRS<br>EELNLVIIGPSADIIQFECKSFGHEVLNLTRNGYGSTQYIRFSPDFTFGFE<br>ESLEVDTNPLLGAGKFATDPAVTLAHELIHAGHRLYGIAINPNRVFKV<br>NTNAYYEMSGLEVSFEELRTFGGHDAKFIDSLQENEFRLYYYNKFKDI<br>ASTLNKAKSIVGTTASLQYMKNVFKEKYLLSEDTSGKFSVDKLKFDK<br>LYKMLTEIYTEDNFVKFFKVLNRKTYLNFDKAVFKINIVPKVNYTIYD<br>GFNLRNTNLAANFNGQNTEINNMNFTKLKNFTGLFEFYKLLCVRGIIT<br>SKTKSLDKGYNKALNDLCIKVNNWDLFFSPSEDNFTNDLNKGEEITSD<br>TNIEAAEENISLDLIQQYYLTFNFDNEPENISIENLSSDIIGQLELMPNIER<br>FPNGKKYELDKYTMFHYLRAQEFEHGKSRIALTNSVNEALLNPSRVY<br>TFFSSDYVKKVNKATEAAMFLGWVEQLVYDFTDETSEVSTTDKIADIT<br>IIIPYIGPALNIGNMLYKDDFVGALIFSGAVILLEFIPEIAIPVLGTFALVS<br>YIANKVLTVQTIDNALSKRNEKWDEVYKYIVTNWLAKVNTQIDLIRK<br>KMKEALENQAEATKAIINYQYNQYTEEEKNNINFNIDDLSSKLNESIN<br>KAMININKFLNQCSVSYLMNSMIPYGVKRLEDFDASLKDALLKYIYDN<br>RGTLIGQVDRLKDKVNNTLSTDIPFQLSKYVDNQRLLSTFTEYIKNILN<br>NIILNLRYKDNNLIDLSGYGAKVEVYDGVELNDKNQFKLTSSANSKIR<br>VTQNQNIIFNSVFLDFSVSFWIRIPKYKNDGIQNYIHNEYTIINCMKNNS<br>GWKISIRGNRIIWTLIDINGKTKSVFFEYNIREDISEYINRWFFVTITNNL<br>NNAKIYINGKLESNTDIKDIREVIANGEIIFKLDGDIDRTQFIWMKYFSIF<br>NTELSQSNIEERYKIQSYSEYLKDFWGNPLMYNKEYYMFNAGNKNSY<br>IKEKKDSPVGEILTRSKYNQNSKYINYRDLYIGEKFIIRRKSNSQSINDDI<br>VRKEDYIYLDFFNENQEWRVYTYKYFKKEEQKLFLAPIYDSDEFYNTI<br>QIKEYDEQPTYSCQLLFKKDEESTDEIGLIGIHRFYESGWWFEEYKDYF<br>CISKWYLKEVKRKPYNLKLGCNWQFIPKDEGWTE |

REFERENCES

1. Schiavo, G., Matteoli, M. & Montecucco, C. Neurotoxins affecting neuroexocytosis. *Physiol Rev* 80, 717-766 (2000).
2. Johnson, E. A. Clostridial toxins as therapeutic agents: benefits of nature's most toxic proteins. *Annu Rev Microbiol* 53, 551-575 (1999).
3. Aoki, K. R. Botulinum toxin: a successful therapeutic protein. *Curr Med Chem* 11, 3085-3092 (2004).
4. Montecucco, C. & Molgo, J. Botulinal neurotoxins: revival of an old killer. *Curr Opin Pharmacol* 5, 274-279 (2005).
5. Lange, O., et al. Neutralizing antibodies and secondary therapy failure after treatment with botulinum toxin type A: much ado about nothing? *Clin Neuropharmacol* 32, 213-218 (2009).
6. Chapman, M. A., Barron, R., Tanis, D. C., Gill, C. E. & Charles, P. D. Comparison of botulinum neurotoxin preparations for the treatment of cervical dystonia. *Clin Ther* 29, 1325-1337 (2007).
7. Cote, T. R., Mohan, A. K., Polder, J. A., Walton, M. K. & Braun, M. M. Botulinum toxin type A injections: adverse events reported to the US Food and Drug Administration in therapeutic and cosmetic cases. *J Am Acad Dermatol* 53, 407-415 (2005).
8. Dong, M., Tepp, W. H., Liu, H., Johnson, E. A. & Chapman, E. R. Mechanism of botulinum neurotoxin B and G entry into hippocampal neurons. *J Cell Biol* 179, 1511-1522 (2007).
9. Peng, L., Tepp, W. H., Johnson, E. A. & Dong, M. Botulinum neurotoxin D uses synaptic vesicle protein SV2 and gangliosides as receptors. *PLoS Pathog* 7, e1002008 (2011).
10. Dong, M., et al. Synaptotagmins I and II mediate entry of botulinum neurotoxin B into cells. *J Cell Biol* 162, 1293-1303 (2003).
11. Nishiki, T., et al. Identification of protein receptor for *Clostridium botulinum* type B neurotoxin in rat brain synaptosomes. *J Biol Chem* 269, 10498-10503 (1994).
12. Rummel, A., Karnath, T., Henke, T., Bigalke, H. & Binz, T. Synaptotagmins I and II act as nerve cell receptors for botulinum neurotoxin G. *J Biol Chem* 279, 30865-30870 (2004).
13. Peng, L., et al. Botulinum neurotoxin D-C uses synaptotagmin I/II as receptors and human synaptotagmin II is not an effective receptor for type B, D-C, and G toxins. *J Cell Sci* (2012).

14. Jin, R., Rummel, A., Binz, T. & Brunger, A. T. Botulinum neurotoxin B recognizes its protein receptor with high affinity and specificity. *Nature* 444, 1092-1095 (2006).
15. Chai, Q., et al. Structural basis of cell surface receptor recognition by botulinum neurotoxin B. *Nature* 444, 1096-1100 (2006).
16. Benoit, R. M., et al. Structural basis for recognition of synaptic vesicle protein 2C by botulinum neurotoxin A. *Nature* 505, 108-111 (2014).
17. Dong, M., et al. Glycosylated SV2A and SV2B mediate the entry of botulinum neurotoxin E into neurons. *Mol Biol Cell* 19, 5226-5237 (2008).
18. Dong, M., et al. SV2 is the protein receptor for botulinum neurotoxin A. *Science* 312, 592-596 (2006).
19. Mahrhold, S., Rummel, A., Bigalke, H., Davletov, B. & Binz, T. The synaptic vesicle protein 2C mediates the uptake of botulinum neurotoxin A into phrenic nerves. *FEBS Lett* 580, 2011-2014 (2006).
20. Rummel, A., et al. Botulinum neurotoxins C, E and F bind gangliosides via a conserved binding site prior to stimulation-dependent uptake with botulinum neurotoxin F utilising the three isoforms of SV2 as second receptor. *J Neurochem* 110, 1942-1954 (2009).
21. Fu, Z., Chen, C., Barbieri, J. T., Kim, J. J. & Baldwin, M. R. Glycosylated SV2 and gangliosides as dual receptors for botulinum neurotoxin serotype F. *Biochemistry* 48, 5631-5641 (2009).
22. Montecucco, C. How do tetanus and botulinum toxins bind to neuronal membranes?*TIBS,* 314-317 (1986).
23. Strotmeier, J., Willjes, G., Binz, T. & Rummel, A. Human synaptotagmin-II is not a high affinity receptor for botulinum neurotoxin B and G: increased therapeutic dosage and immunogenicity. *FEBS Lett* 586, 310-313 (2012).
24. Nishiki, T., et al. The high-affinity binding of *Clostridium botulinum* type B neurotoxin to synaptotagmin II associated with gangliosides GT1b/GD1a. *FEBS Lett* 378, 253-257 (1996).
25. Pang, Z. P., et al. Synaptotagmin-2 is essential for survival and contributes to Ca2+ triggering of neurotransmitter release in central and neuromuscular synapses. *J Neurosci* 26, 13493-13504 (2006).
26. Brin, M. F., et al. Safety and efficacy of NeuroBloc (botulinum toxin type B) in type A-resistant cervical dystonia. *Neurology* 53, 1431-1438 (1999).
27. Pappert, E. J. & Germanson, T. Botulinum toxin type B vs. type A in toxin-naive patients with cervical dystonia: Randomized, double-blind, noninferiority trial. *Mov Disord* 23, 510-517 (2008).
28. Brodsky, M. A., Swope, D. M. & Grimes, D. Diffusion of botulinum toxins. *Tremor Other Hyperkinet Mov* (*N Y*) 2(2012).
29. Wang, J., et al. Longer-acting and highly potent chimaeric inhibitors of excessive exocytosis created with domains from botulinum neurotoxin A and B. *Biochem J* 444, 59-67 (2012).
30. Rummel, A., Mahrhold, S., Bigalke, H. & Binz, T. Exchange of the H(CC) domain mediating double receptor recognition improves the pharmacodynamic properties of botulinum neurotoxin. *FEBS J* 278, 4506-4515 (2011).
31. Nuemket, N., et al. Structural and mutational analyses of the receptor binding domain of botulinum D/C mosaic neurotoxin: Insight into the ganglioside binding mechanism. *Biochem Biophys Res Commun* 411, 433-439 (2011).
32. Berntsson, R. P., Peng, L., Svensson, L. M., Dong, M. & Stenmark, P. Crystal structures of botulinum neurotoxin DC in complex with its protein receptors synaptotagmin I and II. *Structure* 21, 1602-1611 (2013).
33. Kroken, A. R., et al. Unique ganglioside binding by botulinum neurotoxins C and D-SA. *FEBS J* (2011).
34. Strotmeier, J., et al. The biological activity of botulinum neurotoxin type C is dependent upon novel types of ganglioside binding sites. *Mol Microbiol* 81, 143-156 (2011).
35. Arnon, S. S., et al. Botulinum toxin as a biological weapon: medical and public health management. *Jama* 285, 1059-1070 (2001).

All publications, patents and sequence database entries mentioned in the specification herein are hereby incorporated by reference in their entirety as if each individual publication or patent was specifically and individually indicated to be incorporated by reference. In case of conflict, the present application, including any definitions herein, will control.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A modified *Clostridium botulinum* neurotoxin (BoNT) polypeptide comprising a modified receptor binding domain of *Clostridium botulinum* serotype B (BoNT/B), comprising:

(i) a substitution mutation at a position corresponding to 1248 in BoNT serotype B, strain 1 (BoNT/B1) comprising the amino acid sequence of SEQ ID NO: 1, wherein the substitution does not introduce a phenylalanine (F) at the position;

(ii) a substitution mutation at a position corresponding to 1249 in BoNT/B1 comprising the amino acid sequence of SEQ ID NO: 1; or (iii) substitution mutations at positions corresponding to 1248 and 1249 in BoNT/B1 comprising the amino acid sequence of SEQ ID NO: 1.

2. The modified BoNT polypeptide of claim 1, comprising the amino acid sequence of SEQ ID NO: 1 having substitution mutations at positions 1248 and 1249.

3. The modified BoNT polypeptide of claim 2, wherein the substitution mutation introduces any one of tryptophan (W), phenylalanine (F), tyrosine (Y), or histidine (H) at positions 1248 and 1249 of SEC) ID NO: 1.

4. The modified BoNT polypeptide of claim 1, comprising the amino acid sequence of SEQ ID NO: 9 having substitution mutations at positions 389 and 390.

5. The modified BoNT polypeptide of claim 4, wherein the substitution mutation introduces any one of tryptophan (W), phenylalanine (F), tyrosine (Y), or histidine (H) at positions 389 and 390 of SE Q ID NO: 9.

6. The modified BoNT polypeptide of claim 1, comprising the amino acid sequence of SEQ ID NO: 17 having substitution mutations at positions 1261 and 1262.

7. The modified BoNT polypeptide of claim 6, wherein the substitution mutation introduces any one of tryptophan (W), phenylalanine (F), tyrosine (Y), or histidine (H) at positions 1261 and 1262 of SEQ ID NO:17.

8. A modified BoNT polypeptide, comprising the amino acid sequence of a polypeptide corresponding to a fragment between amino acid 1245 and amino acid 1252 of serotype B, strain 1 (BoNT/B1), comprising:

(i) a substitution mutation at a position corresponding to 1248 in BoNT serotype B, strain 1 (BoNT/B1) comprising the amino acid sequence of SEQ ID NO: 1, wherein the substitution does not introduce a phenylalanine (F) at the position;

(ii) a substitution mutation at a position corresponding to 1249 in BoNT/B1 comprising the amino acid sequence of SEQ ID NO: 1; or (iii) substitution mutations at positions corresponding to 1248 and 1249 in BoNT/B1 comprising the amino acid sequence of SEQ ID NO: 1.

9. The modified BoNT polypeptide of claim 8, comprising the amino acid sequence of SEQ ID NO: 25 having substitution mutations at positions 4 and 5.

10. The modified BoNT polypeptide of claim 9, wherein the substitution mutation introduces any one of tryptophan (W), phenylalanine (F), tyrosine (Y), or histidine (H) at positions 4 and 5 of SEQ ID NO: 25.

11. The modified BoNT polypeptide of claim 1, wherein the substitution mutation creates a loop in the receptor binding domain that penetrates a lipid membrane.

12. The modified BoNT polypeptide of claim 1, further comprising one or more substitution mutations at positions corresponding to 1178, 1191, or 1199 in BoNT/B1 comprising the amino acid sequence of SEQ ID NO: 1.

13. The modified BoNT polypeptide of claim 12, wherein the substitution mutations correspond to E1191M/51199Y, E1191M/51199W, E1191M/W1178Q, E1191V/S1199Y, E1191V/S1199W, E1199V/W1178Q, or E1199Q/S1199Y in BoNT/B1 comprising the amino acid sequence of SEQ ID NO: 1.

14. A modified *Clostridium botulinum* neurotoxin (BoNT) polypeptide comprising:

a protease domain;

b) a protease cleavage site;

c) a translocation domain; and d) a modified receptor binding domain of *Clostridium botulinum* serotype B, comprising:

(i) a substitution mutation at a position corresponding to 1248 in BoNT serotype B, strain 1 (BoNT/B1) comprising the amino acid sequence of SEQ ID NO: 1, wherein the substitution does not introduce a phenylalanine (F) at the position;

(ii) a substitution mutation at a position corresponding to 1249 in BoNT/B1 comprising the amino acid sequence of SEQ ID NO: 1; or (iii) substitution mutations at positions corresponding to 1248 and 1249 in BoNT/B1 comprising the amino acid sequence of SEQ ID NO: 1.

15. The modified BoNT polypeptide of claim 14, wherein the protease domain, translocation domain, and protease cleavage site are from serotype selected from the group consisting of A, B, C, D, E, F, G, and combinations thereof.

16. A chimeric molecule comprising a first portion linked to a second portion, wherein the first portion is a modified BoNT polypeptide of claim 1.

17. A method of treating a condition associated with unwanted neuronal activity, the method comprising administering a therapeutically effective amount of the modified BoNT polypeptide of claim 1 to a subject to thereby treat the condition.

18. The modified BoNT polypeptide of claim 1, comprising the amino acid sequence of SEQ ID NO: 1 having a substitution mutation at position 1248, wherein the substitution mutation introduces any one of tryptophan (W), tyrosine (Y), or histidine (H) at position 1248 of SEQ ID NO: 1.

19. The modified BoNT polypeptide of claim 1, comprising the amino acid sequence of SEQ ID NO: 1 having a substitution mutation at position 1249, wherein the substitution mutation introduces any one of tryptophan (W), phenylalanine (F), tyrosine (Y), or histidine (H) at position 1249 of SEQ ID NO: 1.

20. The modified BoNT polypeptide of claim 1, comprising the amino acid sequence of SEQ ID NO: 9 having a substitution mutation at position 389, wherein the substitution mutation introduces any one of tryptophan (W), tyrosine (Y), or histidine (H) at position 389 of SEQ ID NO: 9.

21. The modified BoNT polypeptide of claim 1, comprising the amino acid sequence of SEQ ID NO: 9 having a substitution mutation at position 390, wherein the substitution mutation introduces any one of tryptophan (W), phenylalanine (F), tyrosine (Y), or histidine (H) at position 390 of SEQ ID NO: 9.

22. The modified BoNT polypeptide of claim 1, comprising the amino acid sequence of SEQ ID NO: 17 having a substitution mutation at position 1261, wherein the substitution mutation introduces any one of tryptophan (W), tyrosine (Y), or histidine (H) at position 1261 of SEQ ID NO: 17.

23. The modified BoNT polypeptide of claim 1, comprising the amino acid sequence of SEQ ID NO: 17 having a substitution mutation at position 1262, wherein the substitution mutation introduces any one of tryptophan (W), phenylalanine (F), tyrosine (Y), or histidine (H) at position 1262 of SEQ ID NO: 17.

24. The modified BoNT polypeptide of claim 1, wherein the modified BoNT polypeptide comprises the amino acid sequence of any one of SEQ ID NOs: 33-36.

25. The modified BoNT polypeptide of claim 13, wherein the modified BoNT polypeptide comprises the amino acid sequence of any one of SEQ ID NOs: 46-66.

26. A method of making a modified *Clostridial botulinum* neurotoxin (BoNT) of claim 1, the method comprising making one or more substitution mutations at a position corresponding to 1248 and 1249 in serotype B, strain 1 (BoNT/B1) comprising the amino acid sequence of SEQ ID NO: 1.

* * * * *

UNITED STATES PATENT AND TRADEMARK OFFICE
CERTIFICATE OF CORRECTION

PATENT NO. : 11,104,891 B2
APPLICATION NO. : 16/308146
DATED : August 31, 2021
INVENTOR(S) : Min Dong et al.

Page 1 of 1

It is certified that error appears in the above-identified patent and that said Letters Patent is hereby corrected as shown below:

In the Claims

At Column 373, Claim 3, Line 62, "positions 1248 and 1249 of SEC) ID NO: 1." should read --positions 1248 and 1249 of SEQ ID NO: 1.--

At Column 374, Claim 5, Line 40, "positions 389 and 390 of SE Q ID NO: 9." should read --positions 389 and 390 of SEQ ID NO: 9.--

At Column 374, Claim 7, Line 47, "positions 1261 and 1262 of SEQ ID NO:17." should read --positions 1261 and 1262 of SEQ ID NO: 17.--

At Column 375, Claim 13, Lines 11 and 12, "the substitution mutations correspond to E1191M/51199Y, E1191M/51199W, E1191M/W1178Q, E1191V/S1199Y" should read --the substitution mutations correspond to E1191M/S1199Y, E1191M/S1199W, E1191M/W1178Q, E1191V/S1199Y--

Signed and Sealed this
Fourth Day of January, 2022

Drew Hirshfeld
*Performing the Functions and Duties of the
Under Secretary of Commerce for Intellectual Property and
Director of the United States Patent and Trademark Office*